US009750798B2

United States Patent
Kortekaas et al.

(10) Patent No.: US 9,750,798 B2
(45) Date of Patent: Sep. 5, 2017

(54) BUNYAVIRUSES WITH SEGMENTED GLYCOPROTEIN PRECURSOR GENES AND METHODS FOR GENERATING THESE VIRUSES

(71) Applicant: Stichting Wageningen Research, Wageningen (NL)

(72) Inventors: Jeroen Alexander Kortekaas, Zwolle (NL); Paulus-Jozef Wichgers Schreur, Oldebroek (NL); Nadia Dimitrova Oreshkova, Swifterbant (NL); Robertus Jacobus Maria Moormann, Dronten (NL)

(73) Assignee: STICHTING WAGENINGEN RESEARCH, Wageningan (NL)

( * ) Notice: Subject to any disclaimer, the term of this patent is extended or adjusted under 35 U.S.C. 154(b) by 0 days.

(21) Appl. No.: 14/892,746

(22) PCT Filed: May 21, 2014

(86) PCT No.: PCT/NL2014/050321
§ 371 (c)(1),
(2) Date: Nov. 20, 2015

(87) PCT Pub. No.: WO2014/189372
PCT Pub. Date: Nov. 27, 2014

(65) Prior Publication Data
US 2016/0271241 A1 Sep. 22, 2016

(30) Foreign Application Priority Data

May 21, 2013 (EP) .................................... 13168608
Jan. 10, 2014 (EP) .................................... 14150826

(51) Int. Cl.
*A61K 39/12* (2006.01)
*C12N 7/00* (2006.01)
*A61K 39/00* (2006.01)

(52) U.S. Cl.
CPC ............... *A61K 39/12* (2013.01); *C12N 7/00* (2013.01); *A61K 2039/525* (2013.01); *C12N 2760/12034* (2013.01); *C12N 2760/12221* (2013.01); *C12N 2760/12234* (2013.01); *C12N 2760/12243* (2013.01); *C12N 2760/12262* (2013.01)

(58) Field of Classification Search
CPC .... A61K 39/12; A61K 39/17; A61K 2300/00; A61K 2039/5254; A61K 2039/54; A61K 48/0075; C12N 7/00; C12N 2510/02; C12N 2760/12022; C12N 2760/12034; C12N 2760/12043; C12N 2760/12051; C12N 15/86; C12N 2760/18134; C12N 2760/18143; C07K 14/00
See application file for complete search history.

(56) References Cited

U.S. PATENT DOCUMENTS

| 6,673,572 B2 | 1/2004 | Parks et al. |
| 7,384,774 B2 | 6/2008 | Palese et al. |
| 9,109,199 B2 | 8/2015 | Kortekaas et al. |
| 2010/0047277 A1 | 2/2010 | Compans et al. |
| 2011/0110976 A1 | 5/2011 | Weber et al. |
| 2013/0236493 A1 | 9/2013 | Kortekaas et al. |
| 2016/0002608 A1 | 1/2016 | Kortekaas et al. |

FOREIGN PATENT DOCUMENTS

| WO | 2009150146 A1 | 12/2009 |
| WO | 2011095760 A1 | 8/2011 |
| WO | WO2011/095760 | 8/2011 |
| WO | 2012039607 A1 | 3/2012 |
| WO | WO2012/039607 | 3/2012 |
| WO | 2014189372 A1 | 11/2014 |

OTHER PUBLICATIONS

Ikegami T, Won S, Peters CJ, Makino S. Rescue of infectious rift valley fever virus entirely from cDNA, analysis of virus lacking the NSs gene, and expression of a foreign gene. J Virol. Mar. 2006;80(6):2933-40.*
Bowie Ju, et. al. Science. Mar. 16, 1990;247(4948):1306-10.*
International Search Report dated Sep. 18, 2014 from corresponding PCT Application No. PCT/NL2014/050321.
Oreshkova et al., "A Single Vaccination with an Improved Nonspreading Rift Valley Fever Virus Vaccine Provides Sterile Immunity in Lambs," PLOS ONE, 8:1-10 (2013).
www.wikipedia.org/wiki/Virus_quantification, downloaded from the World Wide Web on Jan. 19, 2017.
Oreshkova, et al. "A Single Vaccination with an Improved Nonspreading Rift Valley Fever Virus Vaccine Provides Sterile Immunity in Lambs." PLOS ONE, Oct. 22, 2013, p. e77461, vol. 8, No. 10, Netherlands.
Bouloy et al., "Reverse Genetics Technology for Rift Valley Fever Virus: Current and Future Applications for the Development of Therapeutics and Vaccines," Antiviral Research, 84 (2):101-118 (2009).
Habjan et al., "T7 RNA Polymerase-Dependent and -Independent Systems for cDNA-Based Rescue of Rift Valley Fever Virus," Journal of General Virology, 89 Pt(9):2157-2166 (2008).
Billecocq et al., "RNA Polymerase I-Mediated Expression of Viral RNA for the Rescue of Infectious Virulent and Avirulent Rift Valley Fever Viruses," Virology, 378(2):377-384 (2008).

(Continued)

*Primary Examiner* — Rachel B Gill
(74) *Attorney, Agent, or Firm* — McDermott Will & Emery LLP

(57) ABSTRACT

The invention relates to a bunyavirus, in which separated (NSm)Gn and Gc coding regions are functionally present on two different genome segments, preferably a bunyavirus that comprises a total of at least 4 genome segments. The invention further relates to methods for producing said bunyavirus, and to a composition comprising said bunyavirus and a suitable excipient.

18 Claims, 36 Drawing Sheets

(56) References Cited

OTHER PUBLICATIONS

Figure 2B:
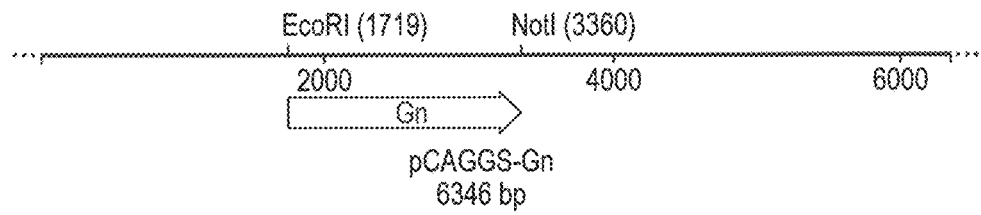

Kortekaas et al., "Rift Valley Fever Virus Immunity Provided by a Paramyxovirus Vaccine Vector," Vaccine, 28 (27):4394-4401 (2010).
Overby et al., "Generation and Analysis of Infectious Virus-Like Particles of Uukuniemi Virus (Bunyaviridae): a Useful System for Studying Bunyaviral Packaging and Budding", J. Virol. 80(21):10428-10435 (2006).
Wichgers Schreur et al., "Creation of Rift Valley Fever Viruses with Four-Segmented Genomes Reveals Flexibility in Bunyavirus Genome Packaging", J. Virol. 88(18): 10883-10893 (2014).
Britton et al., "Expression of bacteriophage T7 RNA polymerase in avian and mammalian cells by a recombinant fowlpox virus", J Gen Virol. 77 ( Pt 5):963-967 (1996).
Shi et al., "Functional analysis of the Bunyamwera orthobunyavirus Gc glycoprotein", J Gen Virol. 90 (Pt 10): 2483-2492 (2009).
Habjan et al., "Efficient production of Rift Valley fever virus-like particles: The antiviral protein MxA can inhibit primary transcription of bunyaviruses", Virology. 385(2):400-408 (2009).
Ikegami et al., "Rift valley fever virus nonstructural protein NSs promotes viral RNA replication and transcription in a minigenome system", J Virol. 79(9): 5606-5615 (2005).
Shi et al., "Role of the Cytoplasmic Tail Domains of Bunyamwera Orthobunyavirus Glycoproteins Gn and Gc in Virus Assembly and Morphogenesis", J Virol. 81(18): 10151-10160 (2007).
Kortekaas et al., "Creation of a Nonspreading Rift Valley Fever Virus", J. Virol. 85(23): 12622-12630 (2011).
Murakami et al., "Development of a Novel, Single-Cycle Replicable Rift Valley Fever Vaccine", PLos Neglected Tropical Diseases, 8(3) p. e2746 (2014).
de Boer et al., "Acid-Activated Structural Reorganization of the Rift Valley Fever Virus Gc Fusion Protein", Journal of Virology, 86(24): 13642-13652 (2012).
International Search Report dated Nov. 29, 2011 from PCT Application No. PCT/NL2011/050631.

\* cited by examiner

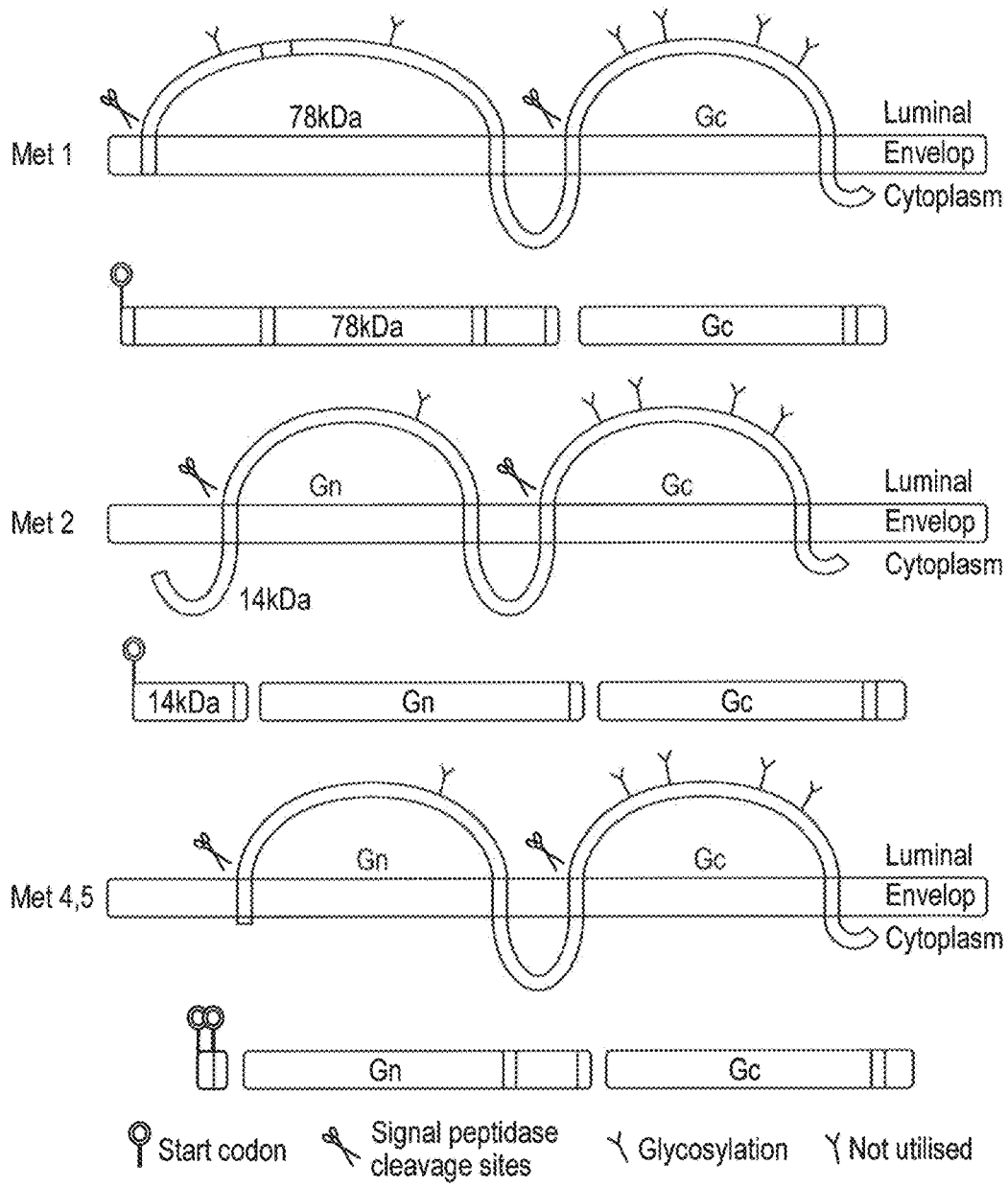

Fig. 2A pCAGGS-NSmGn

EcoRI (1719)   NotI (3753)

2000 pCAGGS-Gn pCAGGS-Gn
6346 bp

GAATTCATGGCAGGGATTGCA

Fig. 2C pCAGGS-Gc

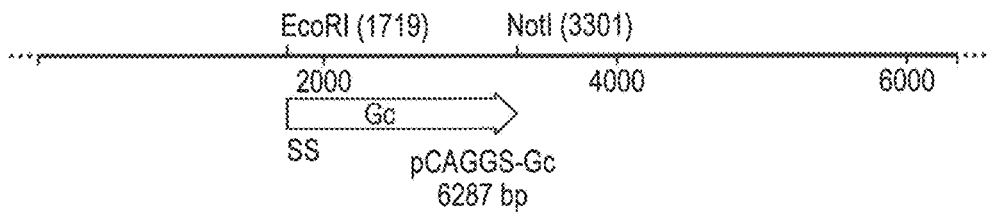

GAATTCATGTATAGCACATACCTAATGCTACTATTGATTGTCTCATATGCATCAGCATGTTCA
GAACTGATTCAGGCAAGCTCCAGAATCACCACTTGCTCCACAGAAGGTGTCAACACCAAGTG
TAGGCTGTCTGGCACAGCATTAATCAGGGCAGGGTCAGTTGGGGCAGAGGCTTGTTTGATGT
TAAAGGGGGTCAAGGAAGACCAAACCAAGTTTTTGAAGATAAAAACTGTCTCAAGTGAGCTA
TCGTGCAGGGAGGGCCAGAGCTATTGGACTGGGTCCTTTAGCCCTAAATGTCTGAGCTCAAG
GAGATGCCATCTTGTCGGGGAATGTCATGTGAATAGGTGTCTGTCTTGGAGAGACAATGAAA
CCTCAGCAGAATTTTCATTTGTTGGGGAAAGCACGACCATGCGGGAGAACAAGTGTTTTGAG
CAGTGTGGAGGATGGGGATGTGGGTGTTTCAATGTGAACCCATCTTGCTTATTTGTGCACAC
GTATCTGCAGTCAGTCAGAAAAGAGGCCCTTAGAGTTTTCAACTGTATCGATTGGGTGCATA
AACTCACTCTAGAGATTACTGACTTTGATGGCTCTGTTTCAACAATAGACCTGGGAGCATCAT
CTAGCCGTTTCACAAACTGGGGTTCAGTTAGCCTCTCACTGGACGCAGAGGGCATTTCAGGC
TCAAACAGCTTTTCCTTCATTGAGAGCCCAGGCAAAGGGTATGCAATTGTTGATGAGCCATTC
TCAGAAATTCCTCGGCAAGGGTTCTTGGGGGAGATCAGGTGCAATTCAGAATCTTCAGTCCT
GAGTGCTCATGAATCATGCCTTAGGGCACCAAATCTTATTTCATACAAGCCCATGATAGATCA
GTTGGAGTGCACAACAAATCTGATTGATCCCTTTGTTGTCTTTGAGAGGGGCTCTCTGCCACA
GACAAGGAATGACAAAACCTTTGCAGCTTCAAAAGGAAATAGGGGTGTTCAAGCTTTCTCTA
AGGGCTCTGTACAGGCTGATCTAACACTGATGTTTGACAATTTTGAGGTGGACTTTGTGGGA
GCAGCCGTGTCTTGTGATGCCGCCTTCTTAAATTTGACAGGTTGCTATTCCTGCAATGCAGGG
GCCAGAGTCTGCCTGTCTATCACATCCACAGGAACTGGAACTCTCTCTGCCCACAATAAAGAT
GGATCTCTGCATATAGTTCTTCCATCAGAGAATGGAACAAAAGATCAGTGTCAGATACTACAC
TTCACTGTACCTGAGGTAGAGGAGGAGTTTATGTACTCTTGTGATGGAGATGAGCGGCCTCT
GTTGGTGAAGGGAACCCTGATAGCTATTGATCCATTTGATGATAGGCGAGAAGCAGGGGGGG
AATCAACAGTTGTGAATCCAAAATCTGGATCTTGGAATTTCTTTGACTGGTTTTCTGGACTCA
TGAGTTGGTTTGGAGGGCCTCTTAAGACTATACTCCTCATTTGCCTGTATGTAGCATTATCAA
TTGGGCTCTTTTTCCTTCTTATATATCTTGGAAGAACAGGCCTCTCTAAAATGTGGCTTGCTG
CCACCAAGAAAGCCTCATAGGCGGCCGC (SEQ ID NO: 6)

Fig. 2D pUC57-S-NSmGn

```
         XbaI (1312)              SpeI (3347)
...┼─────────┬─────────┬─────────┬─────────┬─────────┬...
        1000      2000      3000      4000      5000
  T7   ┌──┬─┐┌─┬───────────────────┐
promoter│ N │▷│◁│       NSmGn      │├ Ribozyme
       └──┴─┘└─┴───────────────────┘
       UTR   IGR                  UTR
              pUC57-S-NSmGn
                 5855 bp
```

ACACAAAGCTCCCTAGAGATACAAACACTATTACAATAATGGACAACTATCAAGAGCTTGCG
ATCCAGTTTGCTGCTCAAGCAGTGGACCGCAATGAGATTGAACAGTGGGTCCGAGAGTTTGC
TTATCAAGGATTTGATGCCCGTAGGGTTATCGAACTCTTAAAGCAGTATGGTGGGGCTGACT
GGGAGAAGGATGCCAAGAAAATGATTGTTCTGGCTCTGACTCGTGGCAACAAGCCCCGGAGG
ATGATGATGAAAATGTCGAAAGAAGGCAAAGCAACTGTGGAGGCTCTCATCAACAAGTATAA
GCTAAAGGAGGGGAATCCTTCCCGGGATGAGTTGACTCTATCACGAGTTGCTGCTGCCCTGG
CTGGCTGGACTTGCCAGGCTTTGGTCGTCTTGAGTGAGTGGCTTCCTGTCACTGGGACCACT
ATGGATGGCCTATCCCCTGCATACCCAAGGCATATGATGCACCCCAGCTTTGCTGGCATGGT
GGACCCTTCTCTACCAGAAGACTATCTAAGGGCAATATTGGATGCTCACTCTCTGTATCTGCT
GCAGTTCTCCCGGGTCATCAACCCAAACCTCCGAGGTAGAACAAAGGAGGAGGTTGCCGCAA
CGTTCACGCAGCCAATGAATGCAGCAGTGAATAGCAACTTTATAAGCCATGAGAAGAGGAGA
GAATTCTTGAAAGCTTTTGGGCTTGTGGATTCCAATGGGAAGCCGTCAGCAGCTGTCATGGC
AGCTGCTCAGGCGTACAAGACAGCAGCCTAAGTGGCTGCCCAGGGGTTTGGGGAAAAGGGC
GTGGTTGGGGTTACGGTCGGGATTGGGGGTGGGGGGTGGGGCAGCCTTAATCTTCTAGATT
ATCTCGGAATGGGGGCCGTGTCGAGGGATGGGGGCAGGGTTACCAAGTGCCAACTGGCCACC
TTCCATCCATCCTATCTCTCTGTTCACCTGGTTAATGTTATCTGCCACCCTTGCCACCATCTTC
TTATACACCCATCGGATGAACACCGTAATCCACATCAACGGGTCGAGGACCTTCCTAGGGGC
AATTTTCAGGCATTTGAGGACTTTGTACAGGATGGCCAGGCAAATGATTGCAACGGAAGAAA
ACACAAAAACCACGACAAAGGCGCTGAGTGCGGTGTGGCATTGGTAGTTAATCAATCCGTGG
GCGCACACAATGCAGCCGTGCACAAGGCAAGGGTCCTGCGGGGGCAGTGGGCAACAATCT
TTGAGCTCACGCTCTGGTCGTCGTGGGCCATATGGACGCCGATATCGCCTCCAGAGCTTTGG
CTGATGCCGGGATACTTCAAAGTGATTTCCGTTGAGGGACTCTGTGAGCCAGTGACACACAC
GCCACTTGCACAGGCGACTGCAGAGCTAATCTTAAATCCGGTAGACCTCACCACCAGACCGT
GTGGTTCACACTTTGTGATGCAGGTGGTGCATGGCTCCACACGCTGGATGGGCTTAGCGCTC
AACTCCCGCTTCACCACCACGCGTTCATAGCCCACACACAACGGCTTCTTCCAGACGCCGGA
CACCTGAATCTGCACCACGCCAGAACCGTTGGCGTGAGAGCAATAAGCGTTGGCATATTGGG
CAGTGCATTCGTAGGCGCTACAGAAGGCGGCGTCGCCGGTGCATTTCTTGCTTCCGTGTCCT
CCGATCTTGGGCACTGGGAAATGTCGAAGGATTTCAGCTCGCGTTTGGTCTGACCGGAGTC
CATGGTACCCTTGTACTGGCCTTTGTGCTCGAAGCACACGAAACTATCAGGAAGCAGGTTTT
CTTCAGTTTTCAGATCCAGTTTGTCGAGGTACACCTTCTTGCTATTCTTAAAAACAGCAAAAG
GGACCACTTCGTGGGCGGTGGAGAGCTGGCCGTCGCACTTTTTAAGGGCTTGCACACCCACC

Fig. 2D (Cont.)

TCGCACACGCCCTTCATTTTAGTTTTGAGCTTGCTGCCGTCGTCCTCTGAGGACTGACAAAAC
AGGTCCTGCAGAGGGTAACTACCCTTCTTAAGACTTGCGCCCGTCATCTGGCGGCAAAAGTT
ACAATCCTCGGTCAGTTCGTACTTTGGTGGGCATTTCACGGAAGCCATCTTGCCGTCATTGTT
GAGATAGTGTGCAGACTGGTAGTCATTCGGGCAATGTGTTTTCATCACCAGTTTCTCTTTCAT
GCACGGGTTGCCATGGGCGCTCTGCAGGTCGCAGCTAGGGGGATCGGCCTTTGCGATAATTG
TGTCGTGGACGGCCTCCAGCAGGGTGCGGTGATGAGCATAGGACTGAAACAGTGGGAATTTT
CCCTTTTCCAGGAGCACGTCGAAGCTAGAGCAGGCGCCAGCATATGTCACCGGCTTACATGT
AGCGTCTTCCTGGGTCATGCCGTCAATATAGTTGTGGCCCTTGCCAGGACGGTTGCGCAGGT
GCGGGTCTTCAGCAAACACCACGGGAGCCAAAGCAAACACGGCCAGTGCAGGCAACACTGT
CATGGCGATTCCGGCCATGGTTTCTCTTCCAATCTGTTTAGCATCTCTTCTTCTTTCACATCTC
ACGATCCCCACTCTTTTCTTATGAGGGGGGCCCTTGACCAGAGAAATCTTATCTTCGGGGTCC
TTCCCGTGGCATGTGATATTGTTCAGGCCGTCAGCGGCAATGATGGCCTTCAGTGCTCTATA
CAGCTCCTGGGAGCTGGTTTTCACTTCCCGAATCCCTGAGATACTACAAGACAGCTCTTCGG
GCATCTCTTCCTCCCTCAGGCTATCCCAAGCGCCCTCGATCATTTCTGGGTTGGTGTAGTCTC
CGAAGCATGTTTCTTCTCTTGTGGAACTCAGACTCACTCTAATGACAGCCTCGCAGACCAGGA
CGGTAATCAGGATAGTCAGCAGGACATA<u>CATGGTGACTAGT</u><u>GATATACTTGATAAGCACTAG</u>
<u>GGGTCTTGTGT</u> (SEQ ID NO: 8)

Fig. 2E pUC57-S-Gc

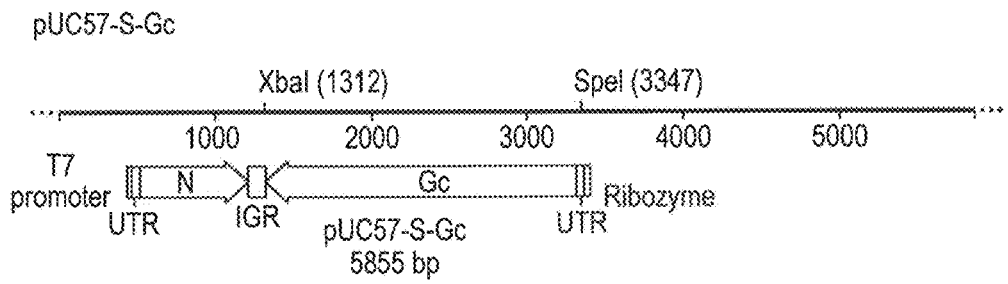

ACACAAAGCTCCCTAGAGATACAAACACTATTACAATAATGGACAACTATCAAGAGCTTGCG
ATCCAGTTTGCTGCTCAAGCAGTGGACCGCAATGAGATTGAACAGTGGGTCCGAGAGTTTGC
TTATCAAGGATTTGATGCCCGTAGGGTTATCGAACTCTTAAAGCAGTATGGTGGGGCTGACT
GGGAGAAGGATGCCAAGAAAATGATTGTTCTGGCTCTGACTCGTGGCAACAAGCCCCGGAGG
ATGATGATGAAAATGTCGAAAGAAGGCAAAGCAACTGTGGAGGCTCTCATCAACAAGTATAA
GCTAAAGGAGGGGAATCCTTCCCGGGATGAGTTGACTCTATCACGAGTTGCTGCTGCCCTGG
CTGGCTGGACTTGCCAGGCTTTGGTCGTCTTGAGTGAGTGGCTTCCTGTCACTGGACCACT
ATGGATGGCCTATCCCCTGCATACCCAAGGCATATGATGCACCCAGCTTTGCTGGCATGGT
GGACCCTTCTCTACCAGAAGACTATCTAAGGGCAATATTGGATGCTCACTCTCTGTATCTGCT
GCAGTTCTCCCGGGTCATCAACCCAAACCTCCGAGGTAGAACAAAGGAGGAGGTTGCCGCAA
CGTTCACGCAGCCAATGAATGCAGCAGTGAATAGCAACTTTATAAGCCATGAGAAGAGGAGA
GAATTCTTGAAAGCTTTTGGGCTTGTGGATTCCAATGGGAAGCCGTCAGCAGCTGTCATGGC
AGCTGCTCAGGCGTACAAGACAGCAGCCTAAGTGGCTGCCCAGGGGTTTGGGGAAAAGGGG
GTGGTTGGGGTTACGGTCGGGATTGGGGGTGGGGGTGGGGCAGCCTTAATCTTCTAGATT
ATCTCGGAATGGGGGCGTGTCGAGGGATGGGGGCAGGGTTACCAAGTGCCAACTGGCCACC
TTCCATCCATCCTATCTCTCTGTTCACCTGGTTAATGTTATCTGCCACCCTTGCCACCATCTTC
TTATACACCCATCGGATGAACACCGTAATCCACATCAACGGGTCGAGGACCTTCCTAGGGGC
AATTTTCAGGCATTTGAGGACTTTGTACAGGATGGCCAGGCAAATGATTGCAACGGAAGAAA
ACACAAAAACCACGACAAAGGCGCTGAGTGCGGTGTGGCATTGGTAGTTAATCAATCCGTGG
GCGCACACAATGCAGCCGTGCACAAGGCAAGGGTCCTGCGGGGGGCAGTGGGCAACAATCT
TTGAGCTCACGCTCTGGTCGTCGTGGGCCATATGGACGCCGATATCGCCTCCAGAGCTTTGG
CTGATGCCGGGATACTTCAAAGTGATTTCCGTTGAGGGACTCTGTGAGCCAGTGACACACAC
GCCACTTGCACAGGCGACTGCAGAGCTAATCTTAAATCCGGTAGACCTCACCACCAGACCGT
GTGGTTCACACTTTGTGATGCAGGTGGTGCATGGCTCCACACGCTGGATGGGCTTAGCGCTC
AACTCCCGCTTCACCACCACGCGTTCATAGCCCACACACAACGGCTTCTTCCAGACGCCGGA
CACCTGAATCTGCACCACGCCAGAACCGTTGGCGTGAGAGCAATAAGCGTTGGCATATTGGG
CAGTGCATTCGTAGGCGCTACAGAAGGCGGCGTCGCCGGTGCATTCTTGCTTCCGTGTCCT
CCGATCTTGGGGCACTGGGAAATGTCGAAGGATTTCAGCTCGCGTTTGGTCTGACCGGAGTC

Fig. 2E (Cont.)

CATGGTACCCTTGTACTGGCCTTTGTGCTCGAAGCACACGAAACTATCAGGAAGCAGGTTTT
CTTCAGTTTTCAGATCCAGTTTGTCGAGGTACACCTTCTTGCTATTCTTAAAAACAGCAAAAG
GGACCACTTCGTGGGCGGTGGAGAGCTGGCCGTCGCACTTTTTAAGGGCTTGCACACCCACC
TCGCACACGCCCTTCATTTTAGTTTTTGAGCTTGCTGCCGTCGTCCTCTGAGGACTGACAAAAC
AGGTCCTGCAGAGGGTAACTACCCTTCTTAAGACTTGCGCCCGTCATCTGGCGGCAAAAGTT
ACAATCCTCGGTCAGTTCGTACTTTGGTGGGCATTTCACGGAAGCCATCTTGCCGTCATTGTT
GAGATAGTGTGCAGACTGGTAGTCATTCGGGCAATGTGTTTCATCACCAGTTTCTCTTTCAT
GCACGGGTTGCCATGGGCGCTCTGCAGGTCGCAGCTAGGGGGATCGGCCTTTGCGATAATTG
TGTCGTGGACGGCCTCCAGCAGGGTGCGGTGATGAGCATAGGACTGAAACAGTGGGAATTTT
CCCTTTTCCAGGAGCACGTCGAAGCTAGAGCAGGCGCCAGCATATGTCACCGGCTTACATGT
AGCGTCTTCCTGGGTCATGCCGTCAATATAGTTGTGGCCCTTGCCAGGACGGTTGCGCAGGT
GCGGGTCTTCAGCAAACACCACGGGAGCCAAAGCAAACACGGCCAGTGCAGGCAACACTGT
CATGGCGATTCCGGCCATGGTTTCTCTTCCAATCTGTTTAGCATCTCTTCTTCTTTCACATCTC
ACGATCCCCACTCTTTTCTTATGAGGGGGGCCCTTGACCAGAGAAATCTTATCTTCGGGGTCC
TTCCCGTGGCATGTGATATTGTTCAGGCCGTCAGCGGCAATGATGGCCTTCAGTGCTCTATA
CAGCTCCTGGGAGCTGGTTTTCACTTCCCGAATCCCTGAGATACTACAAGACAGCTCTTCGG
GCATCTCTTCCTCCCTCAGGCTATCCCAAGCGCCCTCGATCATTTCTGGGTTGGTGTAGTCTC
CGAAGCATGTTTCTTCTCTTGTGGAACTCAGACTCACTCTAATGACAGCCTCGCAGACCAGGA
CGGTAATCAGGATAGTCAGCAGGACATACAT GGTGACTAGT GATATACTTGATAAGCACTAG GGGGTCTTTGTGT (SEQ ID NO: 11)

Fig. 2F

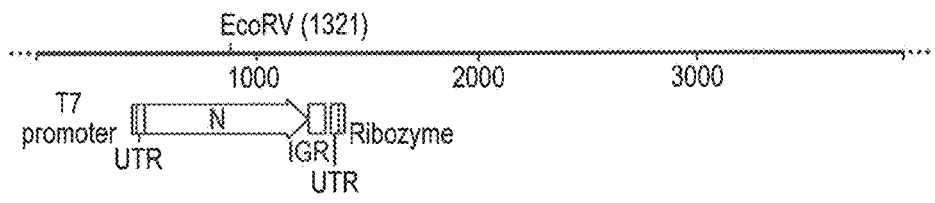

pUC57-S-delNSs
3916 bp

ACACAAAGCTCCCTAGAGATACAAACACTATTACAATAATGGACAACTATCAAGAGCTTGCG
ATCCAGTTTGCTGCTCAAGCAGTGGACCGCAATGAGATTGAACAGTGGGTCCGAGAGTTTGC
TTATCAAGGATTTGATGCCCGTAGGGTTATCGAACTCTTAAAGCAGTATGGTGGGGCTGACT
GGGAGAAGGATGCCAAGAAAATGATTGTTCTGGCTCTGACTCGTGGCAACAAGCCCCGGAGG
ATGATGATGAAAATGTCGAAAGAAGGCAAAGCAACTGTGGAGGCTCTCATCAACAAGTATAA
GCTAAAGGAGGGGAATCCTTCCCGGGATGAGTTGACTCTATCACGAGTTGCTGCTGCCCTGG
CTGGCTGGACTTGCCAGGCTTTGGTCGTCTTGAGTGAGTGGCTTCCTGTCACTGGGACCACC
ATGGATGGCCTATCCCCTGCATACCCAAGGCATATGATGCACCCCAGCTTTGCTGGCATGGT
GGACCCTTCTCTACCAGAAGACTATCTAAGGGCAATATTGGATGCTCACTCTCTGTATCTGCT
GCAGTTCTCCCGGGTCATCAACCCAAACCTCCGAGGTAGAACAAAGGAGGAGGTTGCCGCAA
CGTTCACGCAGCCAATGAATGCAGCAGTGAATAGCAACTTTATAAGCCATGAGAAGAGGAGA
GAATTCTTGAAAGCTTTTGGGCTTGTGGATTCCAATGGGAAGCCGTCAGCAGCTGTCATGGC
AGCTGCTCAGGCGTACAAGACAGCAGCCTAAGTGGCTGCCCAGGGGTTTGGGGAAAAGGCG
GTGGTTGGGGTTACGGTCGGGATTGGGGCTGGGGGGTGGGGCAGCCTTAATCTTCAACAGA
TATCACAGGAAAGTAATCCATGATATACTTGATAAGCACTAGGGGGTCTTTGTGT (SEQ ID NO: 14)

Fig. 2H pUC57-M-Gc

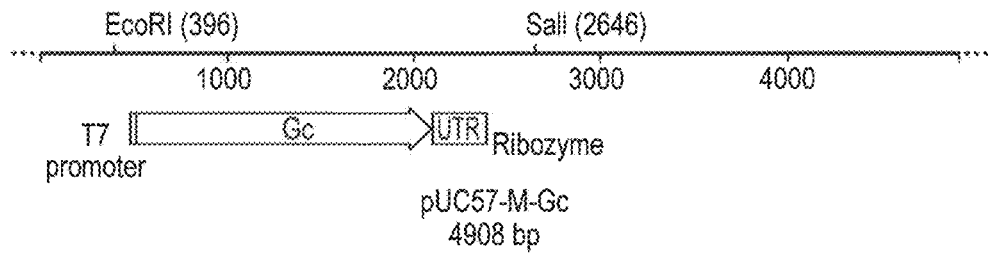

pUC57-M-Gc
4908 bp

ACACAAAGACGGTGCATTAAACCATGTATAGCACATACCTAATGCTACTATTGATTGTCTCAT
ATGCATCAGCATGTTCAGAACTGATTCAGGCAAGCTCCAGAATCACCACTTGCTCCACAGAA
GGTGTCAACACCAAGTGTAGGCTGTCTGGCACAGCATTAATCAGGGCAGGGTCAGTTGGGGC
AGAGGCTTGTTTGATGTTAAAGGGGGTCAAGGAAGACCAAACCAAGTTTTTGAAGATAAAAA
CTGTCTCAAGTGAGCTATCGTGCAGGGAGGGCCAGAGCTATTGGACTGGGTCCTTTAGCCCT
AAATGTCTGAGCTCAAGGAGATGCCATCTTGTCGGGGAATGTCATGTGAATAGGTGTCTGTC
TTGGAGAGACAATGAAACCTCAGCAGAATTTTCATTTGTTGGGGAAAGCACGACCATGCGGG
AGAACAAGTGTTTTGAGCAGTGTGGAGGATGGGGATGTGGGTGTTTCAATGTGAACCCATCT
TGCTTATTTGTGCACACGTATCTGCAGTCAGTCAGAAAAGAGGCCCTTAGAGTTTTCAACTGT
ATCGATTGGGTGCATAAACTCACTCTAGAGATTACTGACTTTGATGGCTCTGTTTCAACAATA
GACCTGGGAGCATCATCTAGCCGTTTCACAAACTGGGGTTCAGTTAGCCTCTCACTGGACGC
AGAGGGCATTTCAGGCTCAAACAGCTTTTCCTTCATTGAGAGCCCAGGCAAAGGGTATGCAA
TTGTTGATGAGCCATTCTCAGAAATTCCTCGGCAAGGGTTCTTGGGGGAGATCAGGTGCAAT
TCAGAATCTTCAGTCCTGAGTGCTCATGAATCATGCCTTAGGGCACCAAATCTTATTTCATAC
AAGCCCATGATAGATCAGTTGGAGTGCACAACAAATCTGATTGATCCCTTTGTTGTCTTTGAG
AGGGGCTCTCTGCCACAGACAAGGAATGACAAAACCTTTGCAGCTTCAAAAGGAAATAGGGG
TGTTCAAGCTTTCTCTAAGGGCTCTGTACAGGCTGATCTAACACTGATGTTTGACAATTTTGA
GGTGGACTTTGTGGGAGCAGCCGTGTCTTGTGATGCCGCCTTCTTAAATTTGACAGGTTGCT
ATTCCTGCAATGCAGGGGCCAGAGTCTGCCTGTCTATCACATCCACAGGAACTGGAACTCTC
TCTGCCCACAATAAAGATGGATCTCTGCATATAGTTCTTCCATCAGAGAATGGAACAAAAGAT
CAGTGTCAGATACTACACTTCACTGTACCTGAGGTAGAGGAGGAGTTTATGTACTCTTGTGAT
GGAGATGAGCGGCCTCTGTTGGTGAAGGGAACCCTGATAGCTATTGATCCATTTGATGATAG
GCGAGAAGCAGGGGGGGAATCAACAGTTGTGAATCCAAAATCTGGATCTTGGAATTTCTTTG
ACTGGTTTTCTGGACTCATGAGTTGGTTTGGAGGGCCTCTTAAGACTATACTCCTCATTTGCC
TGTATGTAGCATTATCAATTGGGCTCTTTTTCCTTCTTATATATCTTGGAAGAACAGGCCTCT
CTAAAATGTGGCTTGCTGCCACCAAGAAAGCCTCATACATCAGTACGTGTAGAAGCAATATA
TAGAAATAAGTAAACATAAGCAAATCTAATTATGTAAATATTGTACAGATGGGTCAAACTATT
GGGATATCCAAGTTTAGAATCTTGTACAATAGTACTTTAGATGTAAGCTTAGTTGTAATTTGG
GGTGGTGGGGTGAGGCAGCAGTAGTCTCAAGTACATGTGGATATTCTAGTTAATGTGAATGT
CTTTTGCCAGATTAGCTGGGAATTAAACTAACTCTTTGAAGTTGCACCGGTCTTTGTGT (SEQ ID NO: 18)

Fig. 2I pUC57-S-CCHFV-N

Start (0) ——————————————————————— End (2357)
| 500 | 1000 | 1500 | 2000 |

[ RVFV N >  < CCHFV N ]
Feature 1      IGR                            Feature 5 pUC57-S-CCHFV-N
2357 bp

ACACAAAGCTCCCTAGAGATACAAACACTATTACAATAATGGACAACTATCAAGAGCTTG
CGATCCAGTTTGCTGCTCAAGCAGTGGACCGCAATGAGATTGAACAGTGGGTCCGAGAGT
TTGCTTATCAAGGATTTGATGCCCGTAGGGTTATCGAACTCTTAAAGCAGTATGGTGGGG
CTGACTGGGAGAAGGATGCCAAGAAAATGATTGTTCTGGCTCTGACTCGTGGCAACAAGC
CCCGGAGGATGATGATGAAAATGTCGAAAGAAGGCAAAGCAACTGTGGAGGCTCTCATCA
ACAAGTATAAGCTAAAGGAGGGGAATCCTTCCCGGGATGAGTTGACTCTATCACGAGTTG
CTGCTGCCCTGGCTGGCTGGACTTGCCAGGCTTTGGTCGTCTTGAGTGAGTGGCTTCCTG
TCACTGGGACCACTATGGATGGCTATCCCCTGCATACCCAAGGCATATGATGCACCCCA
GCTTTGCTGGCATGGTGGACCCTTCTCTACCAGAAGACTATCTAAGGGCAATATTGGATG
CTCACTCTCTGTATCTGCTGCAGTTCTCCCGGGTCATCAACCCAAACCTCCGAGGTAGAA
CAAAGGAGGAGGTTGCCCGCAACGTTCACGCAGCCAATGAATGCAGCAGTGAATAGCAACT
TTATAAGCCATGAGAAGAGGAGAGAATTCTTGAAAGCTTTTGGGCTTGTGGATTCCAATG
GGAAGCCGTCAGCAGCTGTCATGGCAGCTGCTCAGGCGTACAAGACAGCAGCCTAAGTGG
CTGCCCAGGGGTTTGGGAAAAGGGGGTGGTTGGGGTTACGGTCGGGATTGGGGGTGGGG
GGTGGGGCAGCCTTAATCTTCTAGATTAGATGATGTTGGCACTGGTGGCGTTGCCCTTCA
CGTTTGTAGGCGTTCTGGAATGGGGACTGCTTTCCCACCAGGGACTGATGCAGCAGGTGCT
CGCTGGCCACAATGTCCATATCCTGGATGTTAAAGCCCGTCTTCTGCACCTCGAACAGCT
TCACGATGGTCTTGGCGCACGGATTGTTTGTCTCCGTATTGGTGCGCAGGTTCAGAATGG
ACTTGGTATGTCCGCTTCCCTGGGCGGCGTCATCTGGATTGGCCACTGGAATGGTTCCGA
AGCACACGCCCATCTCGCTGATGCGTCCGGCTGTCAGCACGGCTGGGTGCATATAGATGC
GGTTCTGCTGAAAGGAGTCATCGGCGAACAGCTCGTACAGCTTCTTGCCCCACTTCATGG
GTGTGCTCAGCAGGGCCTTCTTCATCTTCTTCGTTCCGCGTGGCTGCTTGCCCAGCTCAA
ACAGGAACTGGCTCACTGTTGGGAAGGTCTCTGGGGTCACTCCGGCCTTATACAGCCAAT

Fig. 2I (Cont.)

AGTAGGAGCTGAAGGCGGTATCAATCTGGGCCGACTGGGCGCGCAGGGCACTGCTGTTCT
TGTACAGCTCCTGGGCCTTGGCAATATGCTTCAGCAGGTTCGTGATCATACTGTCGGCCG
AGGCGCGGTCCACCTCATCCTTGTGCTTATCCAGATATCCATTCAGGGCCTCCACGGTCT
TCTTGGCCTCGTCGAAGATTCCCTTGCCCTCCGTCTCGGCCAGCTTGGCCAGGCCGGTGG
CCACCAGGGCAATTCCGCTGCGGCCGGACTTATTGATATCTCCCCACGGGGGGTTAAAGG
CCATAATGTACTTGCCCTTCACGAACTCGCGGCACCAGTCCACATGCTCGTGCGACACGG
GTCCGCGTGGATTCTCATCTCCTCCGCGATTCAGAATCAGGTTGCGGCGACGGATCATGT
CACTCAGCATCTCCTTCACCGACATCACGATCTCGCCCGGCACCTTGTACTCGGCCAGCA
CCTTGTTGGACAGGGCGGCCGTATTGGCGTTCACGCGGAATCCGATATCCTTGCGCCACT
TCAGGGCGGCCTGCTGATAGCCGGTCAGCTGCTCAATCTTGGGCACGTCCACCTTCAGCT
CGGTGTAACTCTCATCCCACGACTTGATTGTGCCGGCGTTCTTCTCAAACCACTCCAGTC
CCTTCTTCACAATGCCTGTGGAGCTCACCCAGGCGCACTCATAGATTGGGCGCAGAACT
TCGTGGCCTCCACCAGGGCGGAGGCGTAGATGCTGTCCTTCTGGGCGTCATCCGTGGCAC
TGGCCATCTGAAACACGAAGCGATCCAGATTCGGCACCGACTCGCAAAAACTGTACGAGT
TTGTGAACGTATCCACCAGTCCATTTCCCTTCTTAAACTCCTCAAACCAGCGGTTCATCT
CATCCTTGTTGTTCACCTCAATCTTGTTCTCCATGGTACTAGTGATATACTTGATAAGCA
CTAGGGGGTCTTTGTGT (SEQ ID NO: 20)

Fig. 2J pUC57-S-NSmGn (non-optimized NSmGn sequence)

```
        1000      2000      3000      4000      5000
         ├──N──┤►┤◄─────NSm-Gn─────┤    │
        T7    IGR                5'UTR T7 terminator
                  pUC57-S-NSmGm
                     5857 bp
```

ACACAAAGCTCCCTAGAGATACAAACACTATTACAATAATGGACAACTATCAAGAGCTTGCG
ATCCAGTTTGCTGCTCAAGCAGTGGACCGCAATGAGATTGAACAGTGGGTCCGAGAGTTTGC
TTATCAAGGATTTGATGCCCGTAGGGTTATCGAACTCTTAAAGCAGTATGGTGGGGCTGACT
GGGAGAAGGATGCCAAGAAAATGATTGTTCTGGCTCTGACTCGTGGCAACAAGCCCCGGAGG
ATGATGATGAAAATGTCGAAAGAAGGCAAAGCAACTGTGGAGGCTCTCATCAACAAGTATAA
GCTAAAGGAGGGGAATCCTTCCCGGGATGAGTTGACTCTATCACGAGTTGCTGCTGCCCTGG
CTGGCTGGACTTGCCAGGCTTTGGTCGTCTTGAGTGAGTGGCTTCCTGTCACTGGGACCACT
ATGGATGGCCTATCCCCTGCATACCCAAGGCATATGATGCACCCCAGCTTTGCTGGCATGGT
GGACCCTTCTCTACCAGAAGACTATCTAAGGGCAATATTGGATGCTCACTCTCTGTATCTGCT
GCAGTTCTCCCGGGTCATCAACCCAAACCTCCGAGGTAGAACAAAGGAGGAGGTTGCCGCAA
CGTTCACGCAGCCAATGAATGCAGCAGTGAATAGCAACTTTATAAGCCATGAGAAGAGGAGA
GAATTCTTGAAAGCTTTTGGGCTTGTGGATTCCAATGGGAAGCCGTCAGCAGCTGTCATGGC
AGCTGCTCAGGCGTACAAGACAGCAGCCTAAGTGGCTGCCCAGGGCGTTTGGGGAAAAGGGG
GTGGTTGGGGTTACGGTCGGGATTGGGGGTGGGGGGTGGGGCAGCCTTAATCTTCTAGACT
ACTAACGTGGAATTGGAGCATGACGAGGAATAGGGGCAGGGTTCCCTAGAGCCAGCTGGCC
TCCTTCCATCCATCCTATTTCCCTGTTCACCTGATTGATATTGTCTGCTACTCTGGCAACCATC
TTCTTATACACCCATCTGATGAAAACAGTAATCCACATTAGTGGATCCAGAACTTTCCTTGGG
GCAATCTTTAGGCACTTGAGAACTTTATAAAGAATGGCCAAACAAATTATTGCGACAGAGCTA
AATACGAACACAACAACAAAGGCACTGAGAGCAGTGTGACACTGGTAATTTATCAGGCCATG
AGCACACACTATGCAGCCATGCACTAGGCATGGATCCTGGGGAGGGCAGTGAGCTACTATTT
TGGAGCTAACTGACTGATCATCATGTGCCATGTGAACCCCTATGTCCCCCCAGAGGACTGG
GATATCCCTGGATACTTGAGTGTAATCTCGGTAGAAGGGCTCTGCGATCCTGTAACGCAAAC
TCCGCTAGCACAAGCAACTGCAGATGATATCTTGAAACCTGTTGATCGGACAACCAATCCGT
GAGGCTCACATTTGGTTATACAAGTTGTGCAAGGCTCAACTCTCTGGATGGGCTTAGCAGAG
AGTTCTCTCTTCACAACCACCCTCTCATACCCGACACACAAAGGCTTCTTCCAGACCCCGGAT
ACTTGTATCTGTACAACTCCTGACCCATTAGCATGTGAACAATAAGCATTGGCGTATTGAGCA
GTGCACTCATAAGCAGAGCAAAAAGCTGCGTCCCCAGTGCACTTCTTGCTACCATGTCCTCC
AATCTTGGGGCACTGAGAGATATCAAAGCTTTTGAGCTCCCTCTTGGTCTGACCAGAGTCCAT
TGTTCCTTTATACTGTCCCTTATGCTCGAAGCAGACAAATGAGTCTGGCAACAGATTTTCCTC
AGTCTTGAGGTCAAGCTTATCAAGATAAACCTTCTTTGAGTTCTTAAATACTGCAAAGGGCAC
AACCTCATGTGCAGTGCTGAGTTGGCCATCACACTTTTTGAGTGCTTGAACCCCCACTTCGCA

Fig. 2J (Cont.)

GACCCCTTTCATTTTTGTTTTTAATTTTGATCCATCATCCTCACTTGACTGACAAAATAAGTCC
TGAAGAGGATAAGACCCCTTCTTCAAGCTAGCACCTGTCATCTGCCTGCAAAAATTGCAGTCC
TCAGTGAGCTCATATTTAGGAGGGCACTTGACTGAAGCCATTTTCCCGTCATTGTTGAGGTAA
TGAGCTGACTGGTAGTCATTTGGACAGTGTGTCTTCATCACGAGTTTCTCCTTCATGCAGGGA
TTCCCATGAGCACTCTGAAGGTCACAGCTAGGTGGATCAGCCTTTGCAATGATGGTGTCGTG
AACTGCTTCTAGTAGGGTTCTGTGATGGGCATACGACTGGAAGAGGGGGAATTTTCCCTTTT
CGAGCAAGACATCAAAACTGCTACAAGCCCCAGCATATGTCACAGGTTTGCATGTGGCGTCC
TCCTGAGTCATCCCGTCAATGTAGTTGTGCCCCTTCCCTGGTCTGTTTCTGAGATGAGGGTCT
TCAGCAAAAACAACAGGTGCCAAAGCAAAAACTGCTAAGGCTGGAAGGACTGTCATTGCAAT
CCCTGCCATGGTTTCTCTTCCTATTTGCTTAGCGTCTCTTCGTCTCTCACACCGAACTATCCC
CACCCGCTTTTTGTGAGGAGGACCCTTTACGAGAGAAATCTTATCCTCAGGATCCTTACCATG
GCAGGTGATGTTGTTCAAGCCATCAGCAGCAATGATGGCTTTTAATGCCCTATACAATTCCTG
GCTTGAGGTTTTGACCTCCCTTATGCCTGATATGGAACAGGAGAGCTCCTCTGGCATCTCCTC
CTCTCTGAGTGAATCCCAAGCTCCTTCAATCATCTCTGGGTTGGTGTAGTCACCAAAGCAGGT
CTCTTCTCTTGTGGAACTTAGAGACACTCTAATAACCGCCTCACACACCAGAACCGTGATCAG
AATTGTTAGTAAAACATACATGGTACTACTGATATACTTGATAAGCACTAGGGGGTCTTTGTG
(SEQ ID NO: 24)

Fig. 2K pUC57-S-Gc (non-optimized Gc sequence)

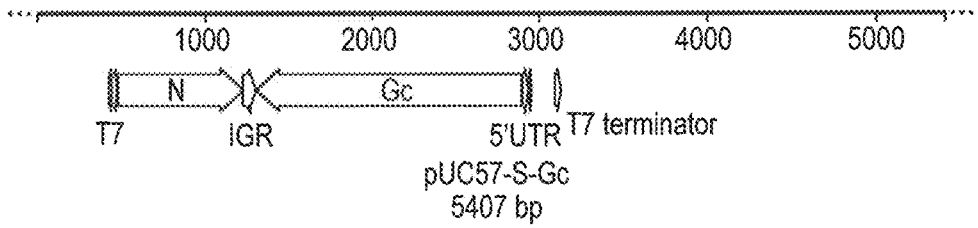

pUC57-S-Gc
5407 bp

ACACAAAGCTCCCTAGAGATACAAACACTATTACAATAATGGACAACTATCAAGAGCTTGCG
ATCCAGTTTGCTGCTCAAGCAGTGGACGCAATGAGATTGAACAGTGGGTCCGAGAGTTTGC
TTATCAAGGATTTGATGCCCGTAGGGTTATCGAACTCTTAAAGCAGTATGGTGGGGCTGACT
GGGAGAAGGATGCCAAGAAAATGATTGTTCTGGCTCTGACTCGTGGCAACAAGCCCCGGAGG
ATGATGATGAAAATGTCGAAAGAAGGCAAAGCAACTGTGGAGGCTCTCATCAACAAGTATAA
GCTAAAGGAGGGGAATCCTTCCCGGGATGAGTTGACTCTATCACGAGTTGCTGCTGCCCTGG
CTGGCTGGACTTGCCAGGCTTTGGTCGTCTTGAGTGAGTGGCTTCCTGTCACTGGGACCACT
ATGGATGGCCTATCCCCTGCATACCCAAGGCATATGATGCACCCCAGCTTTGCTGGCATGGT
GGACCCTTCTCTACCAGAAGACTATCTAAGGGCAATATTGGATGCTCACTCTCTGTATCTGCT
GCAGTTCTCCCGGGTCATCAACCCAAACCTCCGAGGTAGAACAAAGGAGGAGGTTGCCGCAA
CGTTCACGCAGCCAATGAATGCAGCAGTGAATAGCAACTTTATAAGCCATGAGAAGAGGAGA
GAATTCTTGAAAGCTTTTGGGCTTGTGGATTCCAATGGGAAGCCGTCAGCAGCTGTCATGGC
AGCTGCTCAGGCGTACAAGACAGCAGCCTAAGTGGCTGCCCAGGGGTTTGGGGAAAAGGGC
GTGGTTGGGGTTACGGTCGGGATTGGGGGTGGGGGGTGGGGCAGCCTTAATCTTCTAGCGA
TCTATGAGGCTTTCTTGGTGGCAGCAAGCCACATTTTAGAGAGGCCTGTTCTTCCAAGATAT
ATAAGAAGGAAAAAGAGCCCAATTGATAATGCTACATACAGGCAAATGAGGAGTATAGTCTT
AAGAGGCCCTCCAAACCAACTCATGAGTCCAGAAAACCAGTCAAAGAAATTCCAAGATCCAG
ATTTTGGATTCACAACTGTTGATTCCCCCCCTGCTTCTCGCCTATCATCAAATGGATCAATAG
CTATCAGGGTTCCCTTCACCAACAGAGGCCGCTCATCTCCATCACAAGAGTACATAAACTCCT
CCTCTACCTCAGGTACAGTGAAGTGTAGTATCTGACACTGATCTTTTGTTCCATTCTCTGATG
GAAGAACTATATGCAGAGATCCATCTTTATTGTGGGCAGAGAGAGTTCCAGTTCCTGTGGAT
GTGATAGACAGGCAGACTCTGGCCCCTGCATTGCAGGAATAGCAACCTGTCAAATTTAAGAA
GGCGGCATCACAAGACACGGCTGCTCCCACAAAGTCCACCTCAAAATTGTCAAACATCAGTG
TTAGATCAGCCTGTACAGAGCCCTTAGAGAAAGCTTGAACACCCCTATTTCCTTTTGAAGCTG
CAAAGGTTTTGTCATTCCTTGTCTGTGGCAGAGAGCCCCTCTCAAAGACAACAAAGGGATCA
ATCAGATTTGTTGTGCACTCCAACTGATCTATCATGGGCTTGTATGAAATAAGATTTGGTGCC
CTAAGGCATGATTCATGAGCACTCAGGACTGAAGATTCTGAATTGCACCTGATCTCCCCCAA
GAACCCTTGCCGAGGAATTTCTGAGAATGGCTCATCAACAATTGCATACCCTTTGCCTGGGCT
CTCAATGAAGGAAAAGCTGTTTGAGCCTGAAATGCCCTCTGCGTCCAGTGAGAGGCTAACTG
AACCCCAGTTTGTGAAACGGCTAGATGATGCTCCCAGGTCTATTGTTGAAACAGAGCCATCA
AAGTCAGTAATCTCTAGAGTGAGTTTATGCACCCAATCGATACAGTTGAAAACTCTAAGGGCC
TCTTTTCTGACTGACTGCAGATACGTGTGCACAAATAAGCAAGATGGGTTCACATTGAAACAC

Fig. 2K (Cont.)

CCACATCCCCATCCTCCACACTGCTCAAAACACTTGTTCTCCCGCATGGTCGTGCTTTCCCCA
ACAAATGAAAATTCTGCTGAGGTTTCATTGTCTCTCCAAGACAGACACCTATTCACATGACAT
TCCCCGACAAGATGGCATCTCCTTGAGCTCAGACATTTAGGGCTAAAGGACCCAGTCCAATA
GCTCTGGCCCTCCCTGCACGATAGCTCACTTGAGACAGTTTTTATCTTCAAAAACTTGGTTTG
GTCTTCCTTGACCCCCTTTAACATCAAACAAGCCTCTGCCCCAACTGACCCTGCCCTGATTAA
TGCTGTGCCAGACAGCCTACACTTGGTGTTGACACCTTCTGTGGAGCAAGTGGTGATTCTGG
AGCTTGCCTGAATCAGTTCTGAACATGCTGATGCATATGAGACAATCAATAGTAGCATTAGGT
ATGTGCTATACATGGTACTAG[TGATATACTTGATAAGCACTAGGGGGTCTTTGTGT] (SEQ ID NO: 27)

Fig. 3

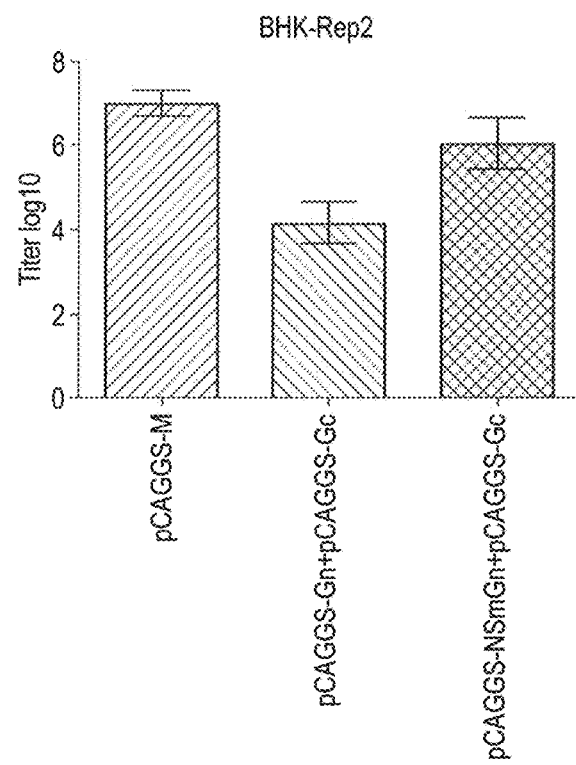

| | Gn | Gc |
|---|---|---|
| RVFV$_{SMML-NSS}$ | | |
| RVFV$_{SMML-delNSS}$ | | |
| RVFV$_{SMML-eGFP}$ | | |

Fig. 6

BSR-T7

▽ RVFV-eGFP
■ RVFV-SMML-eGFP

C6/36

▽ RVFV-eGFP
■ RVFV-SMML-eGFP

Fig. 7

Neutralization Titer

Fig. 8A

AUG
1 2  4,5           <<<PRHAPIPR | YSTYLMLL>>>  (SEQ ID NO: 44)

| NSm | Gn | Gc |

78kDa lumen intravirion

[] Transmembrane region   <<<PRHAPIPR | YSTYLMLL>>> (SEQ ID NO: 44)

Fig. 8B

BHK-Rep2 cells → Transfection (pCAGGS) → Supernatant (NSR) → Titration

Fig. 8C pCAGGS-(NSm)Gn + pCAGGS-Gc : (NSm)Gn + Gc
pCAGGS-Gn + pCAGGS-Gc : Gn + Gc
pCAGGS-(NSm)GnGc : (NSm)GnGc $10^2$  $10^3$  $10^4$  $10^5$  $10^6$  $10^7$  $10^8$
TCID50/ml

Fig. 9A

RVFV (WT)

- 5' — L — Polymerase >> — L — 3'
- 5' — M — NSmGn >> — Gc >> — M — 3'
- 5' — S — N >> — << NSs — S — 3'

RVFV-LMS-split

- 5' — L — Polymerase >> — L — 3'
- 5' — M — NSmGn >> — M — 3'
- 5' — S — N >> — <<Gc — S — 3'

RVFV-LLS

- 5' — L — Polymerase >> — L — 3'
- 5' — S — N >> — <<NSmGn — S — 3'
- 5' — S — N >> — <<Gc — S — 3'

Fig. 9B

RVFV (WT)

RVFV-LMS-split

RVFV-LSS

Fig. 9C

RVFV (WT)
RVFV-LMS-split
RVFV-LSS

Pol.
Gc
Gn
N
NSs

Fig. 9D

Fig. 10A

RVFV (WT)

- 5' [L | Polymerase >> | L] 3'
- 5' [M | NSmGn >> | Gc >> | M] 3'
- 5' [S | N >> | <<sSN | S] 3'

RVFV-LMMS$_{NSs}$

- 5' [L | Polymerase >> | L] 3'
- 5' [M | NSmGn >> | M] 3'
- 5' [M | Gc >> | M] 3'
- 5' [S | N >> | <<sSN | S] 3'

RVFV-LMMS$_{eGFP}$

- 5' [L | Polymerase >> | L] 3'
- 5' [M | NSmGn >> | M] 3'
- 5' [M | Gc >> | M] 3'
- 5' [S | N >> | <<eGFP | S] 3'

Fig. 10A (Cont.)

RVFV-LMMS<sub>delNSs</sub>

```
5'                                                          3'
  | L |         Polymerase >>                        | L |
5'                              3'
  | M |   NSmGn >>      | M |
5'                              3'
  | M |     Gc >>       | M |
5'                      3'
  | S |   N >>     | S |
```

RVFV-LMMM

```
5'                                                          3'
  | L |         Polymerase >>                        | L |
5'                              3'
  | M |   NSmGn >>      | M |
5'                              3'
  | M |     Gc >>       | M |
5'                      3'
  | M |   N >>      | M |
```

Fig. 10B

RVFV (WT)

RVFV-LMMS$_{NSs}$

RVFV-LMMS$_{eGFP}$

RVFV-LMMS$_{delNSs}$

RVFV-LMMM

Fig. 10C

Pol.
Gn
Gc
N
NSs

Fig. 10D

····∇···· RVFV
——▲—— RVFV-LMMS-NSs
– –■– – RVFV-LMMS-eGFP
···◇··· RVFV-LMMS-delNSs
– ·○· – RVFV-LMMM

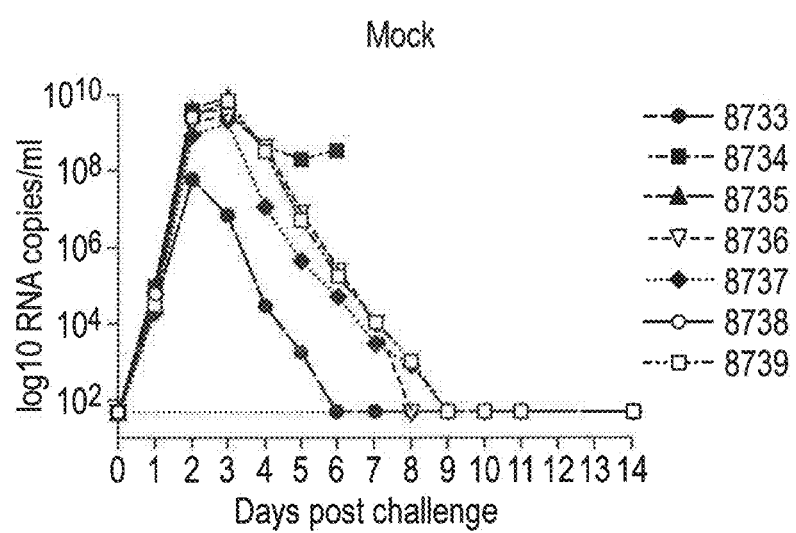

SEQUENCE LISTING

<160> NUMBER OF SEQ ID NOS: 44

<210> SEQ ID NO 1
<211> LENGTH: 18
<212> TYPE: DNA
<213> ORGANISM: Artificial Sequence
<220> FEATURE:
<223> OTHER INFORMATION: promoter T7 polymerase

<400> SEQUENCE: 1
taatacgact cactatag                                                   18

<210> SEQ ID NO 2
<211> LENGTH: 2040
<212> TYPE: DNA
<213> ORGANISM: Artificial Sequence
<220> FEATURE:
<223> OTHER INFORMATION: pCAGGS-NSmGn
<220> FEATURE:
<221> NAME/KEY: CDS
<222> LOCATION: (10)..(2034)

<400> SEQUENCE: 2 gaattcacc atg tat gtt tta cta aca att ctg atc acg gtt ctg gtg tgt 51
Met Tyr Val Leu Leu Thr Ile Leu Ile Thr Val Leu Val Cys
1 5 10 gag gcg gtt att aga gtg tct cta agt tcc aca aga gaa gag acc tgc 99
Glu Ala Val Ile Arg Val Ser Leu Ser Ser Thr Arg Glu Glu Thr Cys
15 20 25 30 ttt ggt gac tac acc aac cca gag atg att gaa gga gct tgg gat tca 147
Phe Gly Asp Tyr Thr Asn Pro Glu Met Ile Glu Gly Ala Trp Asp Ser
35 40 45 ctc aga gag gag gag atg cca gag gag ctc tcc tgt tcc ata tca ggc 195
Leu Arg Glu Glu Glu Met Pro Glu Glu Leu Ser Cys Ser Ile Ser Gly
50 55 60 ata agg gag gtc aaa acc tca agc cag gaa ttg tat agg gca tta aaa 243
Ile Arg Glu Val Lys Thr Ser Ser Gln Glu Leu Tyr Arg Ala Leu Lys
65 70 75 gcc atc att gct gct gat ggc ttg aac aac atc acc tgc cat ggt aag 291
Ala Ile Ile Ala Ala Asp Gly Leu Asn Asn Ile Thr Cys His Gly Lys
80 85 90 gat cct gag gat aag att tct ctc gta aag ggt cct cct cac aaa aag 339
Asp Pro Glu Asp Lys Ile Ser Leu Val Lys Gly Pro Pro His Lys Lys
95 100 105 110 cgg gtg ggg ata gtt cgg tgt gag aga cga aga gac gct aag caa ata 387
Arg Val Gly Ile Val Arg Cys Glu Arg Arg Arg Asp Ala Lys Gln Ile
115 120 125 gga aga gaa acc atg gca ggg att gca atg aca gtc ctt cca gcc tta 435
Gly Arg Glu Thr Met Ala Gly Ile Ala Met Thr Val Leu Pro Ala Leu
130 135 140 gca gtt ttt gct ttg gca cct gtt gtt ttt gct gaa gac cct cat ctc 483
Ala Val Phe Ala Leu Ala Pro Val Val Phe Ala Glu Asp Pro His Leu
145 150 155 aga aac aga cca ggg aag ggg cac aac tac att gac ggg atg act cag 531
Arg Asn Arg Pro Gly Lys Gly His Asn Tyr Ile Asp Gly Met Thr Gln
160 165 170 gag gac gcc aca tgc aaa cct gtg aca tat gct ggg gct tgt agc agt 579
Glu Asp Ala Thr Cys Lys Pro Val Thr Tyr Ala Gly Ala Cys Ser Ser
175 180 185 190 ttt gat gtc ttg ctc gaa aag gga aaa ttc ccc ctc ttc cag tcg tat 627
Phe Asp Val Leu Leu Glu Lys Gly Lys Phe Pro Leu Phe Gln Ser Tyr
195 200 205

```
                                           -continued gcc cat cac aga acc cta cta gaa gca gtt cac gac acc atc att gca    675
Ala His His Arg Thr Leu Leu Glu Ala Val His Asp Thr Ile Ile Ala
            210                 215                 220 aag gct gat cca cct agc tgt gac ctt cag agt gct cat ggg aat ccc    723
Lys Ala Asp Pro Pro Ser Cys Asp Leu Gln Ser Ala His Gly Asn Pro
                225                 230                 235 tgc atg aag gag aaa ctc gtg atg aag aca cac tgt cca aat gac tac    771
Cys Met Lys Glu Lys Leu Val Met Lys Thr His Cys Pro Asn Asp Tyr
        240                 245                 250 cag tca gct cat tac ctc aac aat gac ggg aaa atg gct tca gtc aag    819
Gln Ser Ala His Tyr Leu Asn Asn Asp Gly Lys Met Ala Ser Val Lys
255                 260                 265                 270 tgc cct cct aaa tat gag ctc act gag gac tgc aat ttt tgc agg cag    867
Cys Pro Pro Lys Tyr Glu Leu Thr Glu Asp Cys Asn Phe Cys Arg Gln
                275                 280                 285 atg aca ggt gct agc ttg aag aag ggg tct tat cct ctt cag gac tta    915
Met Thr Gly Ala Ser Leu Lys Lys Gly Ser Tyr Pro Leu Gln Asp Leu
            290                 295                 300 ttt tgt cag tca agt gag gat gat gga tca aaa tta aaa aca aaa atg    963
Phe Cys Gln Ser Ser Glu Asp Asp Gly Ser Lys Leu Lys Thr Lys Met
                305                 310                 315 aaa ggg gtc tgc gaa gtg ggg gtt caa gca ctc aaa aag tgt gat ggc   1011
Lys Gly Val Cys Glu Val Gly Val Gln Ala Leu Lys Lys Cys Asp Gly
320                 325                 330 caa ctc agc act gca cat gag gtt gtg ccc ttt gca gta ttt aag aac   1059
Gln Leu Ser Thr Ala His Glu Val Val Pro Phe Ala Val Phe Lys Asn
335                 340                 345                 350 tca aag aag gtt tat ctt gat aag ctt gac ctc aag act gag gaa aat   1107
Ser Lys Lys Val Tyr Leu Asp Lys Leu Asp Leu Lys Thr Glu Glu Asn
            355                 360                 365 ctg ttg cca gac tca ttt gtc tgc ttc gag cat aag gga cag tat aaa   1155
Leu Leu Pro Asp Ser Phe Val Cys Phe Glu His Lys Gly Gln Tyr Lys
                370                 375                 380 gga aca atg gac tct ggt cag acc aag agg gag ctc aaa agc ttt gat   1203
Gly Thr Met Asp Ser Gly Gln Thr Lys Arg Glu Leu Lys Ser Phe Asp
            385                 390                 395 atc tct cag tgc ccc aag att gga gga cat ggt agc aag aag tgc act   1251
Ile Ser Gln Cys Pro Lys Ile Gly Gly His Gly Ser Lys Lys Cys Thr
        400                 405                 410 ggg gac gca gct ttt tgc tct gct tat gag tgc act gct caa tac gcc   1299
Gly Asp Ala Ala Phe Cys Ser Ala Tyr Glu Cys Thr Ala Gln Tyr Ala
415                 420                 425                 430 aat gct tat tgt tca cat gct aat ggg tca gga gtt gta cag ata caa   1347
Asn Ala Tyr Cys Ser His Ala Asn Gly Ser Gly Val Val Gln Ile Gln
                435                 440                 445 gta tcc ggg gtc tgg aag aag cct ttg tgt gtc ggg tat gag agg gtg   1395
Val Ser Gly Val Trp Lys Lys Pro Leu Cys Val Gly Tyr Glu Arg Val
            450                 455                 460 gtt gtg aag aga gaa ctc tct gct aag ccc atc cag aga gtt gag cct   1443
Val Val Lys Arg Glu Leu Ser Ala Lys Pro Ile Gln Arg Val Glu Pro
        465                 470                 475 tgc aca act tgt ata acc aaa tgt gag cct cac gga ttg gtt gtc cga   1491
Cys Thr Thr Cys Ile Thr Lys Cys Glu Pro His Gly Leu Val Val Arg
480                 485                 490 tca aca ggt ttc aag ata tca tct gca gtt gct tgt gct agc gga gtt   1539
Ser Thr Gly Phe Lys Ile Ser Ser Ala Val Ala Cys Ala Ser Gly Val
495                 500                 505                 510 tgc gtt aca gga tcg cag agc cct tct acc gag att aca ctc aag tat   1587
Cys Val Thr Gly Ser Gln Ser Pro Ser Thr Glu Ile Thr Leu Lys Tyr
            515                 520                 525
```

```
cca ggg ata tcc cag tcc tct ggg ggg gac ata ggg gtt cac atg gca    1635
Pro Gly Ile Ser Gln Ser Ser Gly Gly Asp Ile Gly Val His Met Ala
            530                 535                 540 cat gat gat cag tca gtt agc tcc aaa ata gta gct cac tgc cct ccc    1683
His Asp Asp Gln Ser Val Ser Ser Lys Ile Val Ala His Cys Pro Pro
            545                 550                 555 cag gat cca tgc cta gtg cat ggc tgc ata gtg tgt gct cat ggc ctg    1731
Gln Asp Pro Cys Leu Val His Gly Cys Ile Val Cys Ala His Gly Leu
560                 565                 570 ata aat tac cag tgt cac act gct ctc agt gcc ttt gtt gtt gtg ttc    1779
Ile Asn Tyr Gln Cys His Thr Ala Leu Ser Ala Phe Val Val Val Phe
575                 580                 585                 590 gta ttt agc tct gtc gca ata att tgt ttg gcc att ctt tat aaa gtt    1827
Val Phe Ser Ser Val Ala Ile Ile Cys Leu Ala Ile Leu Tyr Lys Val
                595                 600                 605 ctc aag tgc cta aag att gcc cca agg aaa gtt ctg gat cca cta atg    1875
Leu Lys Cys Leu Lys Ile Ala Pro Arg Lys Val Leu Asp Pro Leu Met
            610                 615                 620 tgg att act gtt ttc atc aga tgg gtg tat aag aag atg gtt gcc aga    1923
Trp Ile Thr Val Phe Ile Arg Trp Val Tyr Lys Lys Met Val Ala Arg
            625                 630                 635 gta gca gac aat atc aat cag gtg aac agg gaa ata gga tgg atg gaa    1971
Val Ala Asp Asn Ile Asn Gln Val Asn Arg Glu Ile Gly Trp Met Glu
640                 645                 650 gga ggc cag ctg gct cta ggg aac cct gcc cct att cct cgt cat gct    2019
Gly Gly Gln Leu Ala Leu Gly Asn Pro Ala Pro Ile Pro Arg His Ala
655                 660                 665                 670 cca att cca cgt tag cggccg                                         2040
Pro Ile Pro Arg <210> SEQ ID NO 3
<211> LENGTH: 674
<212> TYPE: PRT
<213> ORGANISM: Artificial Sequence
<220> FEATURE:
<223> OTHER INFORMATION: Synthetic Construct

<400> SEQUENCE: 3

Met Tyr Val Leu Leu Thr Ile Leu Ile Thr Val Leu Val Cys Glu Ala
1               5                   10                  15

Val Ile Arg Val Ser Leu Ser Ser Thr Arg Glu Glu Thr Cys Phe Gly
            20                  25                  30

Asp Tyr Thr Asn Pro Glu Met Ile Glu Gly Ala Trp Asp Ser Leu Arg
        35                  40                  45

Glu Glu Glu Met Pro Glu Glu Leu Ser Cys Ser Ile Ser Gly Ile Arg
    50                  55                  60

Glu Val Lys Thr Ser Ser Gln Glu Leu Tyr Arg Ala Leu Lys Ala Ile
65                  70                  75                  80

Ile Ala Ala Asp Gly Leu Asn Asn Ile Thr Cys His Gly Lys Asp Pro
                85                  90                  95

Glu Asp Lys Ile Ser Leu Val Lys Gly Pro Pro His Lys Lys Arg Val
            100                 105                 110

Gly Ile Val Arg Cys Glu Arg Arg Asp Ala Lys Gln Ile Gly Arg
        115                 120                 125

Glu Thr Met Ala Gly Ile Ala Met Thr Val Leu Pro Ala Leu Ala Val
    130                 135                 140

Phe Ala Leu Ala Pro Val Val Phe Ala Glu Asp Pro His Leu Arg Asn
145                 150                 155                 160
```

-continued

```
Arg Pro Gly Lys Gly His Asn Tyr Ile Asp Gly Met Thr Gln Glu Asp
            165                 170                 175

Ala Thr Cys Lys Pro Val Thr Tyr Ala Gly Ala Cys Ser Ser Phe Asp
            180                 185                 190

Val Leu Leu Glu Lys Gly Lys Phe Pro Leu Phe Gln Ser Tyr Ala His
            195                 200                 205

His Arg Thr Leu Leu Glu Ala Val His Asp Thr Ile Ile Ala Lys Ala
            210                 215                 220

Asp Pro Pro Ser Cys Asp Leu Gln Ser Ala His Gly Asn Pro Cys Met
225                 230                 235                 240

Lys Glu Lys Leu Val Met Lys Thr His Cys Pro Asn Asp Tyr Gln Ser
            245                 250                 255

Ala His Tyr Leu Asn Asn Asp Gly Lys Met Ala Ser Val Lys Cys Pro
            260                 265                 270

Pro Lys Tyr Glu Leu Thr Glu Asp Cys Asn Phe Cys Arg Gln Met Thr
            275                 280                 285

Gly Ala Ser Leu Lys Lys Gly Ser Tyr Pro Leu Gln Asp Leu Phe Cys
            290                 295                 300

Gln Ser Ser Glu Asp Asp Gly Ser Lys Leu Lys Thr Lys Met Lys Gly
305                 310                 315                 320

Val Cys Glu Val Gly Val Gln Ala Leu Lys Lys Cys Asp Gly Gln Leu
            325                 330                 335

Ser Thr Ala His Glu Val Val Pro Phe Ala Val Phe Lys Asn Ser Lys
            340                 345                 350

Lys Val Tyr Leu Asp Lys Leu Asp Leu Lys Thr Glu Glu Asn Leu Leu
            355                 360                 365

Pro Asp Ser Phe Val Cys Phe Glu His Lys Gly Gln Tyr Lys Gly Thr
            370                 375                 380

Met Asp Ser Gly Gln Thr Lys Arg Glu Leu Lys Ser Phe Asp Ile Ser
385                 390                 395                 400

Gln Cys Pro Lys Ile Gly Gly His Gly Ser Lys Lys Cys Thr Gly Asp
            405                 410                 415

Ala Ala Phe Cys Ser Ala Tyr Glu Cys Thr Ala Gln Tyr Ala Asn Ala
            420                 425                 430

Tyr Cys Ser His Ala Asn Gly Ser Gly Val Val Gln Ile Gln Val Ser
            435                 440                 445

Gly Val Trp Lys Lys Pro Leu Cys Val Gly Tyr Glu Arg Val Val Val
            450                 455                 460

Lys Arg Glu Leu Ser Ala Lys Pro Ile Gln Arg Val Glu Pro Cys Thr
465                 470                 475                 480

Thr Cys Ile Thr Lys Cys Glu Pro His Gly Leu Val Val Arg Ser Thr
            485                 490                 495

Gly Phe Lys Ile Ser Ser Ala Val Ala Cys Ala Ser Gly Val Cys Val
            500                 505                 510

Thr Gly Ser Gln Ser Pro Ser Thr Glu Ile Thr Leu Lys Tyr Pro Gly
            515                 520                 525

Ile Ser Gln Ser Ser Gly Gly Asp Ile Gly Val His Met Ala His Asp
            530                 535                 540

Asp Gln Ser Val Ser Ser Lys Ile Val Ala His Cys Pro Pro Gln Asp
545                 550                 555                 560

Pro Cys Leu Val His Gly Cys Ile Val Cys Ala His Gly Leu Ile Asn
            565                 570                 575
```

-continued

```
Tyr Gln Cys His Thr Ala Leu Ser Ala Phe Val Val Phe Val Phe
            580                 585                 590

Ser Ser Val Ala Ile Ile Cys Leu Ala Ile Leu Tyr Lys Val Leu Lys
        595                 600                 605

Cys Leu Lys Ile Ala Pro Arg Lys Val Leu Asp Pro Leu Met Trp Ile
    610                 615                 620

Thr Val Phe Ile Arg Trp Val Tyr Lys Lys Met Val Ala Arg Val Ala
625                 630                 635                 640

Asp Asn Ile Asn Gln Val Asn Arg Glu Ile Gly Trp Met Glu Gly Gly
                645                 650                 655

Gln Leu Ala Leu Gly Asn Pro Ala Pro Ile Pro Arg His Ala Pro Ile
            660                 665                 670

Pro Arg

<210> SEQ ID NO 4
<211> LENGTH: 1647
<212> TYPE: DNA
<213> ORGANISM: Artificial Sequence
<220> FEATURE:
<223> OTHER INFORMATION: pCAGGS-Gn
<220> FEATURE:
<221> NAME/KEY: CDS
<222> LOCATION: (7)..(1641)

<400> SEQUENCE: 4 gaattc atg gca ggg att gca atg aca gtc ctt cca gcc tta gca gtt      48
       Met Ala Gly Ile Ala Met Thr Val Leu Pro Ala Leu Ala Val
         1               5                  10 ttt gct ttg gca cct gtt gtt ttt gct gaa gac cct cat ctc aga aac     96
Phe Ala Leu Ala Pro Val Val Phe Ala Glu Asp Pro His Leu Arg Asn
 15                  20                  25                  30 aga cca ggg aag ggg cac aac tac att gac ggg atg act cag gag gac    144
Arg Pro Gly Lys Gly His Asn Tyr Ile Asp Gly Met Thr Gln Glu Asp
                 35                  40                  45 gcc aca tgc aaa cct gtg aca tat gct ggg gct tgt agc agt ttt gat    192
Ala Thr Cys Lys Pro Val Thr Tyr Ala Gly Ala Cys Ser Ser Phe Asp
             50                  55                  60 gtc ttg ctc gaa aag gga aaa ttc ccc ctc ttc cag tcg tat gcc cat    240
Val Leu Leu Glu Lys Gly Lys Phe Pro Leu Phe Gln Ser Tyr Ala His
         65                  70                  75 cac aga acc cta cta gaa gca gtt cac gac acc atc att gca aag gct    288
His Arg Thr Leu Leu Glu Ala Val His Asp Thr Ile Ile Ala Lys Ala
     80                  85                  90 gat cca cct agc tgt gac ctt cag agt gct cat ggg aat ccc tgc atg    336
Asp Pro Pro Ser Cys Asp Leu Gln Ser Ala His Gly Asn Pro Cys Met
 95                 100                 105                 110 aag gag aaa ctc gtg atg aag aca cac tgt cca aat gac tac cag tca    384
Lys Glu Lys Leu Val Met Lys Thr His Cys Pro Asn Asp Tyr Gln Ser
                115                 120                 125 gct cat tac ctc aac aat gac ggg aaa atg gct tca gtc aag tgc cct    432
Ala His Tyr Leu Asn Asn Asp Gly Lys Met Ala Ser Val Lys Cys Pro
            130                 135                 140 cct aaa tat gag ctc act gag gac tgc aat ttt tgc agg cag atg aca    480
Pro Lys Tyr Glu Leu Thr Glu Asp Cys Asn Phe Cys Arg Gln Met Thr
        145                 150                 155 ggt gct agc ttg aag aag ggg tct tat cct ctt cag gac tta ttt tgt    528
Gly Ala Ser Leu Lys Lys Gly Ser Tyr Pro Leu Gln Asp Leu Phe Cys
    160                 165                 170 cag tca agt gag gat gat gga tca aaa tta aaa aca aaa atg aaa ggg    576
Gln Ser Ser Glu Asp Asp Gly Ser Lys Leu Lys Thr Lys Met Lys Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 175 |     |     |     | 180 |     |     |     | 185 |     |     |     | 190 |     |     |      |
| gtc | tgc | gaa | gtg | ggg | gtt | caa | gca | ctc | aaa | aag | tgt | gat | ggc | caa | ctc | 624  |
| Val | Cys | Glu | Val | Gly | Val | Gln | Ala | Leu | Lys | Lys | Cys | Asp | Gly | Gln | Leu |      |
|     |     |     |     | 195 |     |     |     |     | 200 |     |     |     |     | 205 |     |      |
| agc | act | gca | cat | gag | gtt | gtg | ccc | ttt | gca | gta | ttt | aag | aac | tca | aag | 672  |
| Ser | Thr | Ala | His | Glu | Val | Val | Pro | Phe | Ala | Val | Phe | Lys | Asn | Ser | Lys |      |
|     |     |     | 210 |     |     |     |     | 215 |     |     |     |     | 220 |     |     |      |
| aag | gtt | tat | ctt | gat | aag | ctt | gac | ctc | aag | act | gag | gaa | aat | ctg | ttg | 720  |
| Lys | Val | Tyr | Leu | Asp | Lys | Leu | Asp | Leu | Lys | Thr | Glu | Glu | Asn | Leu | Leu |      |
|     |     | 225 |     |     |     |     | 230 |     |     |     |     | 235 |     |     |     |      |
| cca | gac | tca | ttt | gtc | tgc | ttc | gag | cat | aag | gga | cag | tat | aaa | gga | aca | 768  |
| Pro | Asp | Ser | Phe | Val | Cys | Phe | Glu | His | Lys | Gly | Gln | Tyr | Lys | Gly | Thr |      |
|     | 240 |     |     |     |     | 245 |     |     |     |     | 250 |     |     |     |     |      |
| atg | gac | tct | ggt | cag | acc | aag | agg | gag | ctc | aaa | agc | ttt | gat | atc | tct | 816  |
| Met | Asp | Ser | Gly | Gln | Thr | Lys | Arg | Glu | Leu | Lys | Ser | Phe | Asp | Ile | Ser |      |
| 255 |     |     |     |     | 260 |     |     |     |     | 265 |     |     |     |     | 270 |      |
| cag | tgc | ccc | aag | att | gga | gga | cat | ggt | agc | aag | aag | tgc | act | ggg | gac | 864  |
| Gln | Cys | Pro | Lys | Ile | Gly | Gly | His | Gly | Ser | Lys | Lys | Cys | Thr | Gly | Asp |      |
|     |     |     |     | 275 |     |     |     |     | 280 |     |     |     |     | 285 |     |      |
| gca | gct | ttt | tgc | tct | gct | tat | gag | tgc | act | gct | caa | tac | gcc | aat | gct | 912  |
| Ala | Ala | Phe | Cys | Ser | Ala | Tyr | Glu | Cys | Thr | Ala | Gln | Tyr | Ala | Asn | Ala |      |
|     |     |     | 290 |     |     |     |     | 295 |     |     |     |     | 300 |     |     |      |
| tat | tgt | tca | cat | gct | aat | ggg | tca | gga | gtt | gta | cag | ata | caa | gta | tcc | 960  |
| Tyr | Cys | Ser | His | Ala | Asn | Gly | Ser | Gly | Val | Val | Gln | Ile | Gln | Val | Ser |      |
|     |     | 305 |     |     |     |     | 310 |     |     |     |     | 315 |     |     |     |      |
| ggg | gtc | tgg | aag | aag | cct | ttg | tgt | gtc | ggg | tat | gag | agg | gtg | gtt | gtg | 1008 |
| Gly | Val | Trp | Lys | Lys | Pro | Leu | Cys | Val | Gly | Tyr | Glu | Arg | Val | Val | Val |      |
|     | 320 |     |     |     |     | 325 |     |     |     |     | 330 |     |     |     |     |      |
| aag | aga | gaa | ctc | tct | gct | aag | ccc | atc | cag | aga | gtt | gag | cct | tgc | aca | 1056 |
| Lys | Arg | Glu | Leu | Ser | Ala | Lys | Pro | Ile | Gln | Arg | Val | Glu | Pro | Cys | Thr |      |
| 335 |     |     |     |     | 340 |     |     |     |     | 345 |     |     |     |     | 350 |      |
| act | tgt | ata | acc | aaa | tgt | gag | cct | cac | gga | ttg | gtt | gtc | cga | tca | aca | 1104 |
| Thr | Cys | Ile | Thr | Lys | Cys | Glu | Pro | His | Gly | Leu | Val | Val | Arg | Ser | Thr |      |
|     |     |     |     | 355 |     |     |     |     | 360 |     |     |     |     | 365 |     |      |
| ggt | ttc | aag | ata | tca | tct | gca | gtt | gct | tgt | gct | agc | gga | gtt | tgc | gtt | 1152 |
| Gly | Phe | Lys | Ile | Ser | Ser | Ala | Val | Ala | Cys | Ala | Ser | Gly | Val | Cys | Val |      |
|     |     |     | 370 |     |     |     |     | 375 |     |     |     |     | 380 |     |     |      |
| aca | gga | tcg | cag | agc | cct | tct | acc | gag | att | aca | ctc | aag | tat | cca | ggg | 1200 |
| Thr | Gly | Ser | Gln | Ser | Pro | Ser | Thr | Glu | Ile | Thr | Leu | Lys | Tyr | Pro | Gly |      |
|     |     | 385 |     |     |     |     | 390 |     |     |     |     | 395 |     |     |     |      |
| ata | tcc | cag | tcc | tct | ggg | ggg | gac | ata | ggg | gtt | cac | atg | gca | cat | gat | 1248 |
| Ile | Ser | Gln | Ser | Ser | Gly | Gly | Asp | Ile | Gly | Val | His | Met | Ala | His | Asp |      |
|     | 400 |     |     |     |     | 405 |     |     |     |     | 410 |     |     |     |     |      |
| gat | cag | tca | gtt | agc | tcc | aaa | ata | gta | gct | cac | tgc | cct | ccc | cag | gat | 1296 |
| Asp | Gln | Ser | Val | Ser | Ser | Lys | Ile | Val | Ala | His | Cys | Pro | Pro | Gln | Asp |      |
| 415 |     |     |     |     | 420 |     |     |     |     | 425 |     |     |     |     | 430 |      |
| cca | tgc | cta | gtg | cat | ggc | tgc | ata | gtg | tgt | gct | cat | ggc | ctg | ata | aat | 1344 |
| Pro | Cys | Leu | Val | His | Gly | Cys | Ile | Val | Cys | Ala | His | Gly | Leu | Ile | Asn |      |
|     |     |     |     | 435 |     |     |     |     | 440 |     |     |     |     | 445 |     |      |
| tac | cag | tgt | cac | act | gct | ctc | agt | gcc | ttt | gtt | gtt | gtg | ttc | gta | ttt | 1392 |
| Tyr | Gln | Cys | His | Thr | Ala | Leu | Ser | Ala | Phe | Val | Val | Val | Phe | Val | Phe |      |
|     |     |     | 450 |     |     |     |     | 455 |     |     |     |     | 460 |     |     |      |
| agc | tct | gtc | gca | ata | att | tgt | ttg | gcc | att | ctt | tat | aaa | gtt | ctc | aag | 1440 |
| Ser | Ser | Val | Ala | Ile | Ile | Cys | Leu | Ala | Ile | Leu | Tyr | Lys | Val | Leu | Lys |      |
|     |     | 465 |     |     |     |     | 470 |     |     |     |     | 475 |     |     |     |      |
| tgc | cta | aag | att | gcc | cca | agg | aaa | gtt | ctg | gat | cca | cta | atg | tgg | att | 1488 |
| Cys | Leu | Lys | Ile | Ala | Pro | Arg | Lys | Val | Leu | Asp | Pro | Leu | Met | Trp | Ile |      |
|     | 480 |     |     |     |     | 485 |     |     |     |     | 490 |     |     |     |     |      |
| act | gtt | ttc | atc | aga | tgg | gtg | tat | aag | aag | atg | gtt | gcc | aga | gta | gca | 1536 |

```
Thr Val Phe Ile Arg Trp Val Tyr Lys Lys Met Val Ala Arg Val Ala
495                 500                 505                 510 gac aat atc aat cag gtg aac agg gaa ata gga tgg atg gaa gga ggc       1584
Asp Asn Ile Asn Gln Val Asn Arg Glu Ile Gly Trp Met Glu Gly Gly
                    515                 520                 525 cag ctg gct cta ggg aac cct gcc cct att cct cgt cat gct cca att       1632
Gln Leu Ala Leu Gly Asn Pro Ala Pro Ile Pro Arg His Ala Pro Ile
                530                 535                 540 cca cgt tag cggccg                                                    1647
Pro Arg <210> SEQ ID NO 5
<211> LENGTH: 544
<212> TYPE: PRT
<213> ORGANISM: Artificial Sequence
<220> FEATURE:
<223> OTHER INFORMATION: Synthetic Construct

<400> SEQUENCE: 5

Met Ala Gly Ile Ala Met Thr Val Leu Pro Leu Ala Val Phe Ala
1               5                   10                  15

Leu Ala Pro Val Val Phe Ala Glu Asp Pro His Leu Arg Asn Arg Pro
                20                  25                  30

Gly Lys Gly His Asn Tyr Ile Asp Gly Met Thr Gln Glu Asp Ala Thr
            35                  40                  45

Cys Lys Pro Val Thr Tyr Ala Gly Ala Cys Ser Ser Phe Asp Val Leu
        50                  55                  60

Leu Glu Lys Gly Lys Phe Pro Leu Phe Gln Ser Tyr Ala His His Arg
65                  70                  75                  80

Thr Leu Leu Glu Ala Val His Asp Thr Ile Ile Ala Lys Ala Asp Pro
                85                  90                  95

Pro Ser Cys Asp Leu Gln Ser Ala His Gly Asn Pro Cys Met Lys Glu
            100                 105                 110

Lys Leu Val Met Lys Thr His Cys Pro Asn Asp Tyr Gln Ser Ala His
        115                 120                 125

Tyr Leu Asn Asn Asp Gly Lys Met Ala Ser Val Lys Cys Pro Pro Lys
130                 135                 140

Tyr Glu Leu Thr Glu Asp Cys Asn Phe Cys Arg Gln Met Thr Gly Ala
145                 150                 155                 160

Ser Leu Lys Lys Gly Ser Tyr Pro Leu Gln Asp Leu Phe Cys Gln Ser
                165                 170                 175

Ser Glu Asp Asp Gly Ser Lys Leu Lys Thr Lys Met Lys Gly Val Cys
            180                 185                 190

Glu Val Gly Val Gln Ala Leu Lys Lys Cys Asp Gly Gln Leu Ser Thr
        195                 200                 205

Ala His Glu Val Val Pro Phe Ala Val Phe Lys Asn Ser Lys Lys Val
210                 215                 220

Tyr Leu Asp Lys Leu Asp Leu Lys Thr Glu Glu Asn Leu Leu Pro Asp
225                 230                 235                 240

Ser Phe Val Cys Phe Glu His Lys Gly Gln Tyr Lys Gly Thr Met Asp
                245                 250                 255

Ser Gly Gln Thr Lys Arg Glu Leu Lys Ser Phe Asp Ile Ser Gln Cys
            260                 265                 270

Pro Lys Ile Gly Gly His Gly Ser Lys Lys Cys Thr Gly Asp Ala Ala
        275                 280                 285

Phe Cys Ser Ala Tyr Glu Cys Thr Ala Gln Tyr Ala Asn Ala Tyr Cys
```

-continued

```
                290                 295                 300
Ser His Ala Asn Gly Ser Gly Val Val Gln Ile Gln Val Ser Gly Val
305                 310                 315                 320

Trp Lys Lys Pro Leu Cys Val Gly Tyr Glu Arg Val Val Lys Arg
                325                 330                 335

Glu Leu Ser Ala Lys Pro Ile Gln Arg Val Glu Pro Cys Thr Thr Cys
                340                 345                 350

Ile Thr Lys Cys Glu Pro His Gly Leu Val Val Arg Ser Thr Gly Phe
                355                 360                 365

Lys Ile Ser Ser Ala Val Ala Cys Ala Ser Gly Val Cys Val Thr Gly
                370                 375                 380

Ser Gln Ser Pro Ser Thr Glu Ile Thr Leu Lys Tyr Pro Gly Ile Ser
385                 390                 395                 400

Gln Ser Ser Gly Gly Asp Ile Gly Val His Met Ala His Asp Asp Gln
                405                 410                 415

Ser Val Ser Ser Lys Ile Val Ala His Cys Pro Pro Gln Asp Pro Cys
                420                 425                 430

Leu Val His Gly Cys Ile Val Cys Ala His Gly Leu Ile Asn Tyr Gln
                435                 440                 445

Cys His Thr Ala Leu Ser Ala Phe Val Val Val Phe Val Phe Ser Ser
                450                 455                 460

Val Ala Ile Ile Cys Leu Ala Ile Leu Tyr Lys Val Leu Lys Cys Leu
465                 470                 475                 480

Lys Ile Ala Pro Arg Lys Val Leu Asp Pro Leu Met Trp Ile Thr Val
                485                 490                 495

Phe Ile Arg Trp Val Tyr Lys Lys Met Val Ala Arg Val Ala Asp Asn
                500                 505                 510

Ile Asn Gln Val Asn Arg Glu Ile Gly Trp Met Glu Gly Gly Gln Leu
                515                 520                 525

Ala Leu Gly Asn Pro Ala Pro Ile Pro Arg His Ala Pro Ile Pro Arg
530                 535                 540

<210> SEQ ID NO 6
<211> LENGTH: 1589
<212> TYPE: DNA
<213> ORGANISM: Artificial Sequence
<220> FEATURE:
<223> OTHER INFORMATION: pCAGGS-Gc
<220> FEATURE:
<221> NAME/KEY: CDS
<222> LOCATION: (7)..(1581)

<400> SEQUENCE: 6 gaattc atg tat agc aca tac cta atg cta cta ttg att gtc tca tat       48
       Met Tyr Ser Thr Tyr Leu Met Leu Leu Leu Ile Val Ser Tyr
        1               5                  10 gca tca gca tgt tca gaa ctg att cag gca agc tcc aga atc acc act      96
Ala Ser Ala Cys Ser Glu Leu Ile Gln Ala Ser Ser Arg Ile Thr Thr
15                  20                  25                  30 tgc tcc aca gaa ggt gtc aac acc aag tgt agg ctg tct ggc aca gca     144
Cys Ser Thr Glu Gly Val Asn Thr Lys Cys Arg Leu Ser Gly Thr Ala
                35                  40                  45 tta atc agg gca ggg tca gtt ggg gca gag gct tgt ttg atg tta aag     192
Leu Ile Arg Ala Gly Ser Val Gly Ala Glu Ala Cys Leu Met Leu Lys
            50                  55                  60 ggg gtc aag gaa gac caa acc aag ttt ttg aag ata aaa act gtc tca     240
Gly Val Lys Glu Asp Gln Thr Lys Phe Leu Lys Ile Lys Thr Val Ser
        65                  70                  75
```

```
agt gag cta tcg tgc agg gag ggc cag agc tat tgg act ggg tcc ttt      288
Ser Glu Leu Ser Cys Arg Glu Gly Gln Ser Tyr Trp Thr Gly Ser Phe
    80              85                  90 agc cct aaa tgt ctg agc tca agg aga tgc cat ctt gtc ggg gaa tgt      336
Ser Pro Lys Cys Leu Ser Ser Arg Arg Cys His Leu Val Gly Glu Cys
95              100                 105                 110 cat gtg aat agg tgt ctg tct tgg aga gac aat gaa acc tca gca gaa      384
His Val Asn Arg Cys Leu Ser Trp Arg Asp Asn Glu Thr Ser Ala Glu
                115                 120                 125 ttt tca ttt gtt ggg gaa agc acg acc atg cgg gag aac aag tgt ttt      432
Phe Ser Phe Val Gly Glu Ser Thr Thr Met Arg Glu Asn Lys Cys Phe
            130                 135                 140 gag cag tgt gga gga tgg gga tgt ggg tgt ttc aat gtg aac cca tct      480
Glu Gln Cys Gly Gly Trp Gly Cys Gly Cys Phe Asn Val Asn Pro Ser
        145                 150                 155 tgc tta ttt gtg cac acg tat ctg cag tca gtc aga aaa gag gcc ctt      528
Cys Leu Phe Val His Thr Tyr Leu Gln Ser Val Arg Lys Glu Ala Leu
    160                 165                 170 aga gtt ttc aac tgt atc gat tgg gtg cat aaa ctc act cta gag att      576
Arg Val Phe Asn Cys Ile Asp Trp Val His Lys Leu Thr Leu Glu Ile
175                 180                 185                 190 act gac ttt gat ggc tct gtt tca aca ata gac ctg gga gca tca tct      624
Thr Asp Phe Asp Gly Ser Val Ser Thr Ile Asp Leu Gly Ala Ser Ser
                195                 200                 205 agc cgt ttc aca aac tgg ggt tca gtt agc ctc tca ctg gac gca gag      672
Ser Arg Phe Thr Asn Trp Gly Ser Val Ser Leu Ser Leu Asp Ala Glu
            210                 215                 220 ggc att tca ggc tca aac agc ttt tcc ttc att gag agc cca ggc aaa      720
Gly Ile Ser Gly Ser Asn Ser Phe Ser Phe Ile Glu Ser Pro Gly Lys
        225                 230                 235 ggg tat gca att gtt gat gag cca ttc tca gaa att cct cgg caa ggg      768
Gly Tyr Ala Ile Val Asp Glu Pro Phe Ser Glu Ile Pro Arg Gln Gly
    240                 245                 250 ttc ttg ggg gag atc agg tgc aat tca gaa tct tca gtc ctg agt gct      816
Phe Leu Gly Glu Ile Arg Cys Asn Ser Glu Ser Ser Val Leu Ser Ala
255                 260                 265                 270 cat gaa tca tgc ctt agg gca cca aat ctt att tca tac aag ccc atg      864
His Glu Ser Cys Leu Arg Ala Pro Asn Leu Ile Ser Tyr Lys Pro Met
                275                 280                 285 ata gat cag ttg gag tgc aca aca aat ctg att gat ccc ttt gtt gtc      912
Ile Asp Gln Leu Glu Cys Thr Thr Asn Leu Ile Asp Pro Phe Val Val
            290                 295                 300 ttt gag agg ggc tct ctg cca cag aca agg aat gac aaa acc ttt gca      960
Phe Glu Arg Gly Ser Leu Pro Gln Thr Arg Asn Asp Lys Thr Phe Ala
        305                 310                 315 gct tca aaa gga aat agg ggt gtt caa gct ttc tct aag ggc tct gta     1008
Ala Ser Lys Gly Asn Arg Gly Val Gln Ala Phe Ser Lys Gly Ser Val
    320                 325                 330 cag gct gat cta aca ctg atg ttt gac aat ttt gag gtg gac ttt gtg     1056
Gln Ala Asp Leu Thr Leu Met Phe Asp Asn Phe Glu Val Asp Phe Val
335                 340                 345                 350 gga gca gcc gtg tct tgt gat gcc gcc ttc tta aat ttg aca ggt tgc     1104
Gly Ala Ala Val Ser Cys Asp Ala Ala Phe Leu Asn Leu Thr Gly Cys
                355                 360                 365 tat tcc tgc aat gca ggg gcc aga gtc tgc ctg tct atc aca tcc aca     1152
Tyr Ser Cys Asn Ala Gly Ala Arg Val Cys Leu Ser Ile Thr Ser Thr
            370                 375                 380 gga act gga act ctc tct gcc cac aat aaa gat gga tct ctg cat ata     1200
Gly Thr Gly Thr Leu Ser Ala His Asn Lys Asp Gly Ser Leu His Ile
```

```
                    385                 390                 395
gtt ctt cca tca gag aat gga aca aaa gat cag tgt cag ata cta cac    1248
Val Leu Pro Ser Glu Asn Gly Thr Lys Asp Gln Cys Gln Ile Leu His
    400                 405                 410 ttc act gta cct gag gta gag gag gag ttt atg tac tct tgt gat gga    1296
Phe Thr Val Pro Glu Val Glu Glu Glu Phe Met Tyr Ser Cys Asp Gly
415                 420                 425                 430 gat gag cgg cct ctg ttg gtg aag gga acc ctg ata gct att gat cca    1344
Asp Glu Arg Pro Leu Leu Val Lys Gly Thr Leu Ile Ala Ile Asp Pro
        435                 440                 445 ttt gat gat agg cga gaa gca ggg ggg gaa tca aca gtt gtg aat cca    1392
Phe Asp Asp Arg Arg Glu Ala Gly Gly Glu Ser Thr Val Val Asn Pro
            450                 455                 460 aaa tct gga tct tgg aat ttc ttt gac tgg ttt tct gga ctc atg agt    1440
Lys Ser Gly Ser Trp Asn Phe Phe Asp Trp Phe Ser Gly Leu Met Ser
                465                 470                 475 tgg ttt gga ggg cct ctt aag act ata ctc ctc att tgc ctg tat gta    1488
Trp Phe Gly Gly Pro Leu Lys Thr Ile Leu Leu Ile Cys Leu Tyr Val
480                 485                 490 gca tta tca att ggg ctc ttt ttc ctt ctt ata tat ctt gga aga aca    1536
Ala Leu Ser Ile Gly Leu Phe Phe Leu Leu Ile Tyr Leu Gly Arg Thr
495                 500                 505                 510 ggc ctc tct aaa atg tgg ctt gct gcc acc aag aaa gcc tca tag        1581
Gly Leu Ser Lys Met Trp Leu Ala Ala Thr Lys Lys Ala Ser
            515                 520 gcggccgc                                                           1589

<210> SEQ ID NO 7
<211> LENGTH: 524
<212> TYPE: PRT
<213> ORGANISM: Artificial Sequence
<220> FEATURE:
<223> OTHER INFORMATION: Synthetic Construct

<400> SEQUENCE: 7

Met Tyr Ser Thr Tyr Leu Met Leu Leu Leu Ile Val Ser Tyr Ala Ser
1               5                   10                  15

Ala Cys Ser Glu Leu Ile Gln Ala Ser Ser Arg Ile Thr Thr Cys Ser
                20                  25                  30

Thr Glu Gly Val Asn Thr Lys Cys Arg Leu Ser Gly Thr Ala Leu Ile
        35                  40                  45

Arg Ala Gly Ser Val Gly Ala Glu Ala Cys Leu Met Leu Lys Gly Val
    50                  55                  60

Lys Glu Asp Gln Thr Lys Phe Leu Lys Ile Lys Thr Val Ser Ser Glu
65                  70                  75                  80

Leu Ser Cys Arg Glu Gly Gln Ser Tyr Trp Thr Gly Ser Phe Ser Pro
                85                  90                  95

Lys Cys Leu Ser Ser Arg Arg Cys His Leu Val Gly Glu Cys His Val
                100                 105                 110

Asn Arg Cys Leu Ser Trp Arg Asp Asn Glu Thr Ser Ala Glu Phe Ser
            115                 120                 125

Phe Val Gly Glu Ser Thr Thr Met Arg Glu Asn Lys Cys Phe Glu Gln
        130                 135                 140

Cys Gly Gly Trp Gly Cys Gly Cys Phe Asn Val Asn Pro Ser Cys Leu
145                 150                 155                 160

Phe Val His Thr Tyr Leu Gln Ser Val Arg Lys Glu Ala Leu Arg Val
                165                 170                 175
```

```
Phe Asn Cys Ile Asp Trp Val His Lys Leu Thr Leu Glu Ile Thr Asp
                180                 185                 190

Phe Asp Gly Ser Val Ser Thr Ile Asp Leu Gly Ala Ser Ser Ser Arg
            195                 200                 205

Phe Thr Asn Trp Gly Ser Val Ser Leu Ser Leu Asp Ala Glu Gly Ile
        210                 215                 220

Ser Gly Ser Asn Ser Phe Ser Phe Ile Glu Ser Pro Gly Lys Gly Tyr
225                 230                 235                 240

Ala Ile Val Asp Glu Pro Phe Ser Glu Ile Pro Arg Gln Gly Phe Leu
                245                 250                 255

Gly Glu Ile Arg Cys Asn Ser Glu Ser Ser Val Leu Ser Ala His Glu
            260                 265                 270

Ser Cys Leu Arg Ala Pro Asn Leu Ile Ser Tyr Lys Pro Met Ile Asp
        275                 280                 285

Gln Leu Glu Cys Thr Thr Asn Leu Ile Asp Pro Phe Val Val Phe Glu
290                 295                 300

Arg Gly Ser Leu Pro Gln Thr Arg Asn Asp Lys Thr Phe Ala Ala Ser
305                 310                 315                 320

Lys Gly Asn Arg Gly Val Gln Ala Phe Ser Lys Gly Ser Val Gln Ala
                325                 330                 335

Asp Leu Thr Leu Met Phe Asp Asn Phe Glu Val Asp Phe Val Gly Ala
            340                 345                 350

Ala Val Ser Cys Asp Ala Ala Phe Leu Asn Leu Thr Gly Cys Tyr Ser
        355                 360                 365

Cys Asn Ala Gly Ala Arg Val Cys Leu Ser Ile Thr Ser Thr Gly Thr
370                 375                 380

Gly Thr Leu Ser Ala His Asn Lys Asp Gly Ser Leu His Ile Val Leu
385                 390                 395                 400

Pro Ser Glu Asn Gly Thr Lys Asp Gln Cys Gln Ile Leu His Phe Thr
                405                 410                 415

Val Pro Glu Val Glu Glu Phe Met Tyr Ser Cys Asp Gly Asp Glu
            420                 425                 430

Arg Pro Leu Leu Val Lys Gly Thr Leu Ile Ala Ile Asp Pro Phe Asp
        435                 440                 445

Asp Arg Arg Glu Ala Gly Gly Glu Ser Thr Val Val Asn Pro Lys Ser
450                 455                 460

Gly Ser Trp Asn Phe Phe Asp Trp Phe Ser Gly Leu Met Ser Trp Phe
465                 470                 475                 480

Gly Gly Pro Leu Lys Thr Ile Leu Leu Ile Cys Leu Tyr Val Ala Leu
                485                 490                 495

Ser Ile Gly Leu Phe Phe Leu Leu Ile Tyr Leu Gly Arg Thr Gly Leu
            500                 505                 510

Ser Lys Met Trp Leu Ala Ala Thr Lys Lys Ala Ser
        515                 520

<210> SEQ ID NO 8
<211> LENGTH: 2934
<212> TYPE: DNA
<213> ORGANISM: Artificial Sequence
<220> FEATURE:
<223> OTHER INFORMATION: pUC57-S-NSmGn
<220> FEATURE:
<221> NAME/KEY: CDS
<222> LOCATION: (39)..(776)

<400> SEQUENCE: 8
```

```
acacaaagct ccctagagat acaaacacta ttacaata atg gac aac tat caa gag        56
                                         Met Asp Asn Tyr Gln Glu
                                         1               5 ctt gcg atc cag ttt gct gct caa gca gtg gac cgc aat gag att gaa        104
Leu Ala Ile Gln Phe Ala Ala Gln Ala Val Asp Arg Asn Glu Ile Glu
            10                  15                  20 cag tgg gtc cga gag ttt gct tat caa gga ttt gat gcc cgt agg gtt        152
Gln Trp Val Arg Glu Phe Ala Tyr Gln Gly Phe Asp Ala Arg Arg Val
        25                  30                  35 atc gaa ctc tta aag cag tat ggt ggg gct gac tgg gag aag gat gcc        200
Ile Glu Leu Leu Lys Gln Tyr Gly Gly Ala Asp Trp Glu Lys Asp Ala
    40                  45                  50 aag aaa atg att gtt ctg gct ctg act cgt ggc aac aag ccc cgg agg        248
Lys Lys Met Ile Val Leu Ala Leu Thr Arg Gly Asn Lys Pro Arg Arg
55                  60                  65                  70 atg atg atg aaa atg tcg aaa gaa ggc aaa gca act gtg gag gct ctc        296
Met Met Met Lys Met Ser Lys Glu Gly Lys Ala Thr Val Glu Ala Leu
                75                  80                  85 atc aac aag tat aag cta aag gag ggg aat cct tcc cgg gat gag ttg        344
Ile Asn Lys Tyr Lys Leu Lys Glu Gly Asn Pro Ser Arg Asp Glu Leu
            90                  95                  100 act cta tca cga gtt gct gct gcc ctg gct ggc tgg act tgc cag gct        392
Thr Leu Ser Arg Val Ala Ala Ala Leu Ala Gly Trp Thr Cys Gln Ala
        105                 110                 115 ttg gtc gtc ttg agt gag tgg ctt cct gtc act ggg acc act atg gat        440
Leu Val Val Leu Ser Glu Trp Leu Pro Val Thr Gly Thr Thr Met Asp
    120                 125                 130 ggc cta tcc cct gca tac cca agg cat atg atg cac ccc agc ttt gct        488
Gly Leu Ser Pro Ala Tyr Pro Arg His Met Met His Pro Ser Phe Ala
135                 140                 145                 150 ggc atg gtg gac cct tct cta cca gaa gac tat cta agg gca ata ttg        536
Gly Met Val Asp Pro Ser Leu Pro Glu Asp Tyr Leu Arg Ala Ile Leu
                155                 160                 165 gat gct cac tct ctg tat ctg ctg cag ttc tcc cgg gtc atc aac cca        584
Asp Ala His Ser Leu Tyr Leu Leu Gln Phe Ser Arg Val Ile Asn Pro
            170                 175                 180 aac ctc cga ggt aga aca aag gag gag gtt gcc gca acg ttc acg cag        632
Asn Leu Arg Gly Arg Thr Lys Glu Glu Val Ala Ala Thr Phe Thr Gln
        185                 190                 195 cca atg aat gca gca gtg aat agc aac ttt ata agc cat gag aag agg        680
Pro Met Asn Ala Ala Val Asn Ser Asn Phe Ile Ser His Glu Lys Arg
    200                 205                 210 aga gaa ttc ttg aaa gct ttt ggg ctt gtg gat tcc aat ggg aag ccg        728
Arg Glu Phe Leu Lys Ala Phe Gly Leu Val Asp Ser Asn Gly Lys Pro
215                 220                 225                 230 tca gca gct gtc atg gca gct gct cag gcg tac aag aca gca gcc taa        776
Ser Ala Ala Val Met Ala Ala Ala Gln Ala Tyr Lys Thr Ala Ala
                235                 240                 245 gtggctgccc aggggtttgg ggaaaagggg gtggttgggg ttacggtcgg gattgggggt        836 gggggggtggg gcagccttaa tcttctagat tatctcggaa tggggcgtg tcgagggatg         896 ggggcagggt taccaagtgc caactggcca ccttccatcc atcctatctc tctgttcacc        956
tggttaatgt tatctgccac ccttgccacc atcttcttat acacccatcg gatgaacacc       1016
gtaatccaca tcaacgggtc gaggaccttc ctaggggcaa ttttcaggca tttgaggact       1076
ttgtacagga tggccaggca aatgattgca acggaagaaa acacaaaaac cacgacaaag       1136
gcgctgagtg cggtgtggca ttggtagtta atcaatccgt gggcgcacac aatgcagccg       1196
tgcacaaggc aagggtcctg cggggggcag tgggcaacaa tctttgagct cacgctctgg       1256
```

```
tcgtcgtggg ccatatggac gccgatatcg cctccagagc tttggctgat gccgggatac    1316
ttcaaagtga tttccgttga gggactctgt gagccagtga cacacacgcc acttgcacag    1376
gcgactgcag agctaatctt aaatccggta gacctcacca ccagaccgtg tggttcacac    1436
tttgtgatgc aggtggtgca tggctccaca cgctggatgg gcttagcgct caactcccgc    1496
ttcaccacca cgcgttcata gcccacacac aacggcttct tccagacgcc ggacacctga    1556
atctgcacca cgccagaacc gttggcgtga gagcaataag cgttggcata ttgggcagtg    1616
cattcgtagg cgctacagaa ggcggcgtcg ccggtgcatt tcttgcttcc gtgtcctccg    1676
atcttggggc actgggaaat gtcgaaggat ttcagctcgc gtttggtctg accggagtcc    1736
atggtaccct tgtactggcc tttgtgctcg aagcacacga actatcagg aagcaggttt     1796 tcttcagttt tcagatccag tttgtcgagg tacaccttct tgctattctt aaaaacagca    1856
aaagggacca cttcgtgggc ggtggagagc tggccgtcgc actttttaag ggcttgcaca    1916
cccacctcgc acacgccctt cattttagtt ttgagcttgc tgccgtcgtc ctctgaggac    1976
tgacaaaaca ggtcctgcag agggtaacta cccttcttaa gacttgcgcc cgtcatctgg    2036
cggcaaaagt tacaatcctc ggtcagttcg tactttggtg ggcatttcac ggaagccatc    2096
ttgccgtcat tgttgagata gtgtgcagac tggtagtcat tcgggcaatg tgttttcatc    2156
accagtttct ctttcatgca cgggttgcca tgggcgctct gcaggtcgca gctaggggga    2216
tcggcctttg cgataattgt gtcgtggacg gcctccagca gggtgcggtg atgagcatag    2276
gactgaaaca gtgggaattt tccctttttcc aggagcacgt cgaagctaga gcaggcgcca    2336
gcatatgtca ccggcttaca tgtagcgtct tcctgggtca tgccgtcaat atagttgtgg    2396
cccttgccag gacggttgcg caggtgcggg tcttcagcaa acaccacggg agccaaagca    2456
aacacggcca gtgcaggcaa cactgtcatg gcgattccgg ccatggtttc tcttccaatc    2516
tgtttagcat ctcttcttct ttcacatctc acgatcccca ctcttttctt atgaggggggg   2576 cccttgacca gagaaatctt atcttcgggg tccttcccgt ggcatgtgat attgttcagg    2636
ccgtcagcgg caatgatggc cttcagtgct ctatacagct cctgggagct ggttttcact    2696
tcccgaatcc ctgagatact acaagacagc tcttcgggca tctcttcctc cctcaggcta    2756
tcccaagcgc cctcgatcat ttctgggttg gtgtagtctc cgaagcatgt ttcttctctt    2816
gtggaactca gactcactct aatgacagcc tcgcagacca ggacggtaat caggatagtc    2876
agcaggacat acatggtgac tagtgatata cttgataagc actaggggggt ctttgtgt     2934
```

<210> SEQ ID NO 9
<211> LENGTH: 245
<212> TYPE: PRT
<213> ORGANISM: Artificial Sequence
<220> FEATURE:
<223> OTHER INFORMATION: Synthetic Construct

<400> SEQUENCE: 9

```
Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
            20                  25                  30

Phe Asp Ala Arg Arg Val Ile Glu Leu Leu Lys Gln Tyr Gly Gly Ala
        35                  40                  45

Asp Trp Glu Lys Asp Ala Lys Lys Met Ile Val Leu Ala Leu Thr Arg
    50                  55                  60
```

```
Gly Asn Lys Pro Arg Arg Met Met Met Lys Met Ser Lys Glu Gly Lys
65                  70                  75                  80

Ala Thr Val Glu Ala Leu Ile Asn Lys Tyr Lys Leu Lys Glu Gly Asn
                85                  90                  95

Pro Ser Arg Asp Glu Leu Thr Leu Ser Arg Val Ala Ala Ala Leu Ala
            100                 105                 110

Gly Trp Thr Cys Gln Ala Leu Val Val Leu Ser Glu Trp Leu Pro Val
        115                 120                 125

Thr Gly Thr Thr Met Asp Gly Leu Ser Pro Ala Tyr Pro Arg His Met
    130                 135                 140

Met His Pro Ser Phe Ala Gly Met Val Asp Pro Ser Leu Pro Glu Asp
145                 150                 155                 160

Tyr Leu Arg Ala Ile Leu Asp Ala His Ser Leu Tyr Leu Leu Gln Phe
                165                 170                 175

Ser Arg Val Ile Asn Pro Asn Leu Arg Gly Arg Thr Lys Glu Glu Val
            180                 185                 190

Ala Ala Thr Phe Thr Gln Pro Met Asn Ala Ala Val Asn Ser Asn Phe
        195                 200                 205

Ile Ser His Glu Lys Arg Arg Glu Phe Leu Lys Ala Phe Gly Leu Val
    210                 215                 220

Asp Ser Asn Gly Lys Pro Ser Ala Ala Val Met Ala Ala Ala Gln Ala
225                 230                 235                 240

Tyr Lys Thr Ala Ala
                245

<210> SEQ ID NO 10
<211> LENGTH: 674
<212> TYPE: PRT
<213> ORGANISM: Artificial Sequence
<220> FEATURE:
<223> OTHER INFORMATION: protein encoded by complementary strand of
      pUC57-S-NSmGn

<400> SEQUENCE: 10

Met Tyr Val Leu Leu Thr Ile Leu Ile Thr Val Leu Val Cys Glu Ala
1               5                   10                  15

Val Ile Arg Val Ser Leu Ser Ser Thr Arg Glu Glu Thr Cys Phe Gly
            20                  25                  30

Asp Tyr Thr Asn Pro Glu Met Ile Glu Gly Ala Trp Asp Ser Leu Arg
        35                  40                  45

Glu Glu Glu Met Pro Glu Glu Leu Ser Cys Ser Ile Ser Gly Ile Arg
    50                  55                  60

Glu Val Lys Thr Ser Ser Gln Glu Leu Tyr Arg Ala Leu Lys Ala Ile
65                  70                  75                  80

Ile Ala Ala Asp Gly Leu Asn Asn Ile Thr Cys His Gly Lys Asp Pro
                85                  90                  95

Glu Asp Lys Ile Ser Leu Val Lys Gly Pro Pro His Lys Lys Arg Val
            100                 105                 110

Gly Ile Val Arg Cys Glu Arg Arg Arg Asp Ala Lys Gln Ile Gly Arg
        115                 120                 125

Glu Thr Met Ala Gly Ile Ala Met Thr Val Leu Pro Ala Leu Ala Val
    130                 135                 140

Phe Ala Leu Ala Pro Val Val Phe Ala Glu Asp Pro His Leu Arg Asn
145                 150                 155                 160

Arg Pro Gly Lys Gly His Asn Tyr Ile Asp Gly Met Thr Gln Glu Asp
                165                 170                 175
```

```
Ala Thr Cys Lys Pro Val Thr Tyr Ala Gly Ala Cys Ser Ser Phe Asp
            180                 185                 190

Val Leu Leu Glu Lys Gly Lys Phe Pro Leu Phe Gln Ser Tyr Ala His
        195                 200                 205

His Arg Thr Leu Leu Glu Ala Val His Asp Thr Ile Ile Ala Lys Ala
    210                 215                 220

Asp Pro Pro Ser Cys Asp Leu Gln Ser Ala His Gly Asn Pro Cys Met
225                 230                 235                 240

Lys Glu Lys Leu Val Met Lys Thr His Cys Pro Asn Asp Tyr Gln Ser
                245                 250                 255

Ala His Tyr Leu Asn Asn Asp Gly Lys Met Ala Ser Val Lys Cys Pro
            260                 265                 270

Pro Lys Tyr Glu Leu Thr Glu Asp Cys Asn Phe Cys Arg Gln Met Thr
        275                 280                 285

Gly Ala Ser Leu Lys Lys Gly Ser Tyr Pro Leu Gln Asp Leu Phe Cys
    290                 295                 300

Gln Ser Ser Glu Asp Asp Gly Ser Lys Leu Lys Thr Lys Met Lys Gly
305                 310                 315                 320

Val Cys Glu Val Gly Val Gln Ala Leu Lys Lys Cys Asp Gly Gln Leu
                325                 330                 335

Ser Thr Ala His Glu Val Val Pro Phe Ala Val Phe Lys Asn Ser Lys
            340                 345                 350

Lys Val Tyr Leu Asp Lys Leu Asp Leu Lys Thr Glu Glu Asn Leu Leu
        355                 360                 365

Pro Asp Ser Phe Val Cys Phe Glu His Lys Gly Gln Tyr Lys Gly Thr
370                 375                 380

Met Asp Ser Gly Gln Thr Lys Arg Glu Leu Lys Ser Phe Asp Ile Ser
385                 390                 395                 400

Gln Cys Pro Lys Ile Gly Gly His Gly Ser Lys Lys Cys Thr Gly Asp
                405                 410                 415

Ala Ala Phe Cys Ser Ala Tyr Glu Cys Thr Ala Gln Tyr Ala Asn Ala
            420                 425                 430

Tyr Cys Ser His Ala Asn Gly Ser Gly Val Val Gln Ile Gln Val Ser
        435                 440                 445

Gly Val Trp Lys Lys Pro Leu Cys Val Gly Tyr Glu Arg Val Val Val
    450                 455                 460

Lys Arg Glu Leu Ser Ala Lys Pro Ile Gln Arg Val Glu Pro Cys Thr
465                 470                 475                 480

Thr Cys Ile Thr Lys Cys Glu Pro His Gly Leu Val Val Arg Ser Thr
                485                 490                 495

Gly Phe Lys Ile Ser Ser Ala Val Ala Cys Ala Ser Gly Val Cys Val
            500                 505                 510

Thr Gly Ser Gln Ser Pro Ser Thr Glu Ile Thr Leu Lys Tyr Pro Gly
        515                 520                 525

Ile Ser Gln Ser Ser Gly Gly Asp Ile Gly Val His Met Ala His Asp
    530                 535                 540

Asp Gln Ser Val Ser Ser Lys Ile Val Ala His Cys Pro Pro Gln Asp
545                 550                 555                 560

Pro Cys Leu Val His Gly Cys Ile Val Cys Ala His Gly Leu Ile Asn
                565                 570                 575

Tyr Gln Cys His Thr Ala Leu Ser Ala Phe Val Val Phe Val Phe
            580                 585                 590
```

```
Ser Ser Val Ala Ile Ile Cys Leu Ala Ile Leu Tyr Lys Val Leu Lys
        595                 600                 605

Cys Leu Lys Ile Ala Pro Arg Lys Val Leu Asp Pro Leu Met Trp Ile
610                 615                 620

Thr Val Phe Ile Arg Trp Val Tyr Lys Lys Met Val Ala Arg Val Ala
625                 630                 635                 640

Asp Asn Ile Asn Gln Val Asn Arg Glu Ile Gly Trp Met Glu Gly Gly
                645                 650                 655

Gln Leu Ala Leu Gly Asn Pro Ala Pro Ile Pro Arg His Ala Pro Ile
            660                 665                 670

Pro Arg

<210> SEQ ID NO 11
<211> LENGTH: 2934
<212> TYPE: DNA
<213> ORGANISM: Artificial Sequence
<220> FEATURE:
<223> OTHER INFORMATION: pUC57-S-Gc
<220> FEATURE:
<221> NAME/KEY: CDS
<222> LOCATION: (39)..(776)

<400> SEQUENCE: 11
acacaaagct ccctagagat acaaacacta ttacaata atg gac aac tat caa gag      56
                                          Met Asp Asn Tyr Gln Glu
                                            1               5 ctt gcg atc cag ttt gct gct caa gca gtg gac cgc aat gag att gaa      104
Leu Ala Ile Gln Phe Ala Ala Gln Ala Val Asp Arg Asn Glu Ile Glu
         10                  15                  20 cag tgg gtc cga gag ttt gct tat caa gga ttt gat gcc cgt agg gtt      152
Gln Trp Val Arg Glu Phe Ala Tyr Gln Gly Phe Asp Ala Arg Arg Val
     25                  30                  35 atc gaa ctc tta aag cag tat ggt ggg gct gac tgg gag aag gat gcc      200
Ile Glu Leu Leu Lys Gln Tyr Gly Gly Ala Asp Trp Glu Lys Asp Ala
 40                  45                  50 aag aaa atg att gtt ctg gct ctg act cgt ggc aac aag ccc cgg agg      248
Lys Lys Met Ile Val Leu Ala Leu Thr Arg Gly Asn Lys Pro Arg Arg
55                  60                  65                  70 atg atg atg aaa atg tcg aaa gaa ggc aaa gca act gtg gag gct ctc      296
Met Met Met Lys Met Ser Lys Glu Gly Lys Ala Thr Val Glu Ala Leu
                 75                  80                  85 atc aac aag tat aag cta aag gag ggg aat cct tcc cgg gat gag ttg      344
Ile Asn Lys Tyr Lys Leu Lys Glu Gly Asn Pro Ser Arg Asp Glu Leu
             90                  95                 100 act cta tca cga gtt gct gct gcc ctg gct ggc tgg act tgc cag gct      392
Thr Leu Ser Arg Val Ala Ala Ala Leu Ala Gly Trp Thr Cys Gln Ala
         105                 110                 115 ttg gtc gtc ttg agt gag tgg ctt cct gtc act ggg acc act atg gat      440
Leu Val Val Leu Ser Glu Trp Leu Pro Val Thr Gly Thr Thr Met Asp
     120                 125                 130 ggc cta tcc cct gca tac cca agg cat atg atg cac ccc agc ttt gct      488
Gly Leu Ser Pro Ala Tyr Pro Arg His Met Met His Pro Ser Phe Ala
 135                 140                 145                 150 ggc atg gtg gac cct tct cta cca gaa gac tat cta agg gca ata ttg      536
Gly Met Val Asp Pro Ser Leu Pro Glu Asp Tyr Leu Arg Ala Ile Leu
                 155                 160                 165 gat gct cac tct ctg tat ctg ctg cag ttc tcc cgg tca atc aac cca      584
Asp Ala His Ser Leu Tyr Leu Leu Gln Phe Ser Arg Val Ile Asn Pro
             170                 175                 180 aac ctc cga ggt aga aca aag gag gag gtt gcc gca acg ttc acg cag      632
```

```
Asn Leu Arg Gly Arg Thr Lys Glu Glu Val Ala Ala Thr Phe Thr Gln
            185                 190                 195 cca atg aat gca gca gtg aat agc aac ttt ata agc cat gag aag agg    680
Pro Met Asn Ala Ala Val Asn Ser Asn Phe Ile Ser His Glu Lys Arg
        200                 205                 210 aga gaa ttc ttg aaa gct ttt ggg ctt gtg gat tcc aat ggg aag ccg    728
Arg Glu Phe Leu Lys Ala Phe Gly Leu Val Asp Ser Asn Gly Lys Pro
215                 220                 225                 230 tca gca gct gtc atg gca gct gct cag gcg tac aag aca gca gcc taa   776
Ser Ala Ala Val Met Ala Ala Ala Gln Ala Tyr Lys Thr Ala Ala
                    235                 240                 245 gtggctgccc aggggtttgg ggaaaagggg gtggttgggg ttacggtcgg gattgggggt   836
gggggggtggg gcagccttaa tcttctagat tatctcggaa tggggggcgtg tcgagggatg   896
ggggcagggt taccaagtgc caactggcca ccttccatcc atcctatctc tctgttcacc    956
tggttaatgt tatctgccac ccttgccacc atcttcttat acacccatcg gatgaacacc  1016
gtaatccaca tcaacgggtc gaggaccttc ctaggggcaa ttttcaggca tttgaggact  1076
ttgtacagga tggccaggca aatgattgca acggaagaaa acacaaaaac cacgacaaag  1136
gcgctgagtg cggtgtggca ttggtagtta atcaatccgt gggcgcacac aatgcagccg  1196
tgcacaaggc aagggtcctg cgggggggcag tgggcaacaa tctttgagct cacgctctgg  1256
tcgtcgtggg ccatatggac gccgatatcg cctccagagc tttggctgat gccgggatac  1316
ttcaaagtga tttccgttga gggactctgt gagccagtga cacacacgcc acttgcacag  1376
gcgactgcag agctaatctt aaatccggta gacctcacca ccagaccgtg tggttcacac  1436
tttgtgatgc aggtggtgca tggctccaca cgctggatgg gcttagcgct caactcccgc  1496
ttcaccacca cgcgttcata gcccacacac aacggcttct tccagacgcc ggacacctga  1556
atctgcacca cgccagaacc gttggcgtga gagcaataag cgttggcata ttgggcagtg  1616
cattcgtagg cgctacagaa ggcggcgtcg ccggtgcatt tcttgcttcc gtgtcctccg  1676
atcttggggc actgggaaat gtcgaaggat ttcagctcgc gtttggtctg accggagtcc  1736
atggtaccct tgtactggcc tttgtgctcg aagcacacga aactatcagg aagcaggttt  1796
tcttcagttt tcagatccag tttgtcgagg tacaccttct tgctattctt aaaaacagca  1856
aaagggacca cttcgtgggc ggtggagagc tggccgtcgc acttttttaag ggcttgcaca  1916
cccacctcgc acacgccctt cattttagtt ttgagcttgc tgccgtcgtc ctctgaggac  1976
tgacaaaaca ggtcctgcag agggtaacta cccttcttaa gacttgcgcc cgtcatctgg  2036
cggcaaaagt tacaatcctc ggtcagttcg tactttggtg ggcatttcac ggaagccatc  2096
ttgccgtcat tgttgagata gtgtgcagac tggtagtcat tcgggcaatg tgttttcatc  2156
accagtttct ctttcatgca cggggttgcca tgggcgctct gcaggtcgca gctagggggga  2216
tcggcctttg cgataattgt gtcgtggacg gcctccagca gggtgcggtg atgagcatag  2276
gactgaaaca gtgggaattt tcccttttcc aggagcacgt cgaagctaga gcaggcgcca  2336
gcatatgtca ccggcttaca tgtagcgtct tcctgggtca tgccgtcaat atagttgtgg  2396
cccttgccag gacggttgcg caggtgcggg tcttcagcaa acaccacggg agccaaagca  2456
aacacggcca gtgcaggcaa cactgtcatg gcgattccgg ccatggtttc tcttccaatc  2516
tgtttagcat ctcttcttct ttcacatctc acgatcccca ctctttcttt atgagggggg  2576
cccttgacca gagaaatctt atcttcgggg tccttcccgt ggcatgtgat attgttcagg  2636
ccgtcagcgg caatgatggc cttcagtgct ctatacagct cctgggagct ggttttcact  2696
```

```
tcccgaatcc ctgagatact acaagacagc tcttcgggca tctcttcctc cctcaggcta    2756
tcccaagcgc cctcgatcat ttctggttg gtgtagtctc cgaagcatgt ttcttctctt    2816
gtggaactca gactcactct aatgacagcc tcgcagacca ggacggtaat caggatagtc    2876
agcaggacat acatggtgac tagtgatata cttgataagc actagggggt ctttgtgt     2934
```

```
<210> SEQ ID NO 12
<211> LENGTH: 245
<212> TYPE: PRT
<213> ORGANISM: Artificial Sequence
<220> FEATURE:
<223> OTHER INFORMATION: Synthetic Construct

<400> SEQUENCE: 12
```

Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
            20                  25                  30

Phe Asp Ala Arg Arg Val Ile Glu Leu Leu Lys Gln Tyr Gly Gly Ala
        35                  40                  45

Asp Trp Glu Lys Asp Ala Lys Lys Met Ile Val Leu Ala Leu Thr Arg
    50                  55                  60

Gly Asn Lys Pro Arg Arg Met Met Met Lys Met Ser Lys Glu Gly Lys
65                  70                  75                  80

Ala Thr Val Glu Ala Leu Ile Asn Lys Tyr Lys Leu Lys Glu Gly Asn
                85                  90                  95

Pro Ser Arg Asp Glu Leu Thr Leu Ser Arg Val Ala Ala Ala Leu Ala
            100                 105                 110

Gly Trp Thr Cys Gln Ala Leu Val Val Leu Ser Glu Trp Leu Pro Val
        115                 120                 125

Thr Gly Thr Thr Met Asp Gly Leu Ser Pro Ala Tyr Pro Arg His Met
    130                 135                 140

Met His Pro Ser Phe Ala Gly Met Val Asp Pro Ser Leu Pro Glu Asp
145                 150                 155                 160

Tyr Leu Arg Ala Ile Leu Asp Ala His Ser Leu Tyr Leu Leu Gln Phe
                165                 170                 175

Ser Arg Val Ile Asn Pro Asn Leu Arg Gly Arg Thr Lys Glu Glu Val
            180                 185                 190

Ala Ala Thr Phe Thr Gln Pro Met Asn Ala Ala Val Asn Ser Asn Phe
        195                 200                 205

Ile Ser His Glu Lys Arg Arg Glu Phe Leu Lys Ala Phe Gly Leu Val
    210                 215                 220

Asp Ser Asn Gly Lys Pro Ser Ala Ala Val Met Ala Ala Ala Gln Ala
225                 230                 235                 240

Tyr Lys Thr Ala Ala
                245

```
<210> SEQ ID NO 13
<211> LENGTH: 674
<212> TYPE: PRT
<213> ORGANISM: Artificial Sequence
<220> FEATURE:
<223> OTHER INFORMATION: protein encoded by complementary strand of
      pUC57-S-Gc

<400> SEQUENCE: 13
```

Met Tyr Val Leu Leu Thr Ile Leu Ile Thr Val Leu Val Cys Glu Ala
1               5                   10                  15

```
Val Ile Arg Val Ser Leu Ser Ser Thr Arg Glu Glu Thr Cys Phe Gly
            20                  25                  30

Asp Tyr Thr Asn Pro Glu Met Ile Glu Gly Ala Trp Asp Ser Leu Arg
            35                  40                  45

Glu Glu Glu Met Pro Glu Leu Ser Cys Ser Ile Ser Gly Ile Arg
 50                  55                  60

Glu Val Lys Thr Ser Ser Gln Glu Leu Tyr Arg Ala Leu Lys Ala Ile
 65                  70                  75                  80

Ile Ala Ala Asp Gly Leu Asn Asn Ile Thr Cys His Gly Lys Asp Pro
            85                  90                  95

Glu Asp Lys Ile Ser Leu Val Lys Gly Pro Pro His Lys Lys Arg Val
            100                 105                 110

Gly Ile Val Arg Cys Glu Arg Arg Asp Ala Lys Gln Ile Gly Arg
            115                 120                 125

Glu Thr Met Ala Gly Ile Ala Met Thr Val Leu Pro Ala Leu Ala Val
 130                 135                 140

Phe Ala Leu Ala Pro Val Val Phe Ala Glu Asp Pro His Leu Arg Asn
145                 150                 155                 160

Arg Pro Gly Lys Gly His Asn Tyr Ile Asp Gly Met Thr Gln Glu Asp
            165                 170                 175

Ala Thr Cys Lys Pro Val Thr Tyr Ala Gly Ala Cys Ser Ser Phe Asp
            180                 185                 190

Val Leu Leu Glu Lys Gly Lys Phe Pro Leu Phe Gln Ser Tyr Ala His
            195                 200                 205

His Arg Thr Leu Leu Glu Ala Val His Asp Thr Ile Ile Ala Lys Ala
            210                 215                 220

Asp Pro Pro Ser Cys Asp Leu Gln Ser Ala His Gly Asn Pro Cys Met
225                 230                 235                 240

Lys Glu Lys Leu Val Met Lys Thr His Cys Pro Asn Asp Tyr Gln Ser
            245                 250                 255

Ala His Tyr Leu Asn Asn Asp Gly Lys Met Ala Ser Val Lys Cys Pro
            260                 265                 270

Pro Lys Tyr Glu Leu Thr Glu Asp Cys Asn Phe Cys Arg Gln Met Thr
            275                 280                 285

Gly Ala Ser Leu Lys Lys Gly Ser Tyr Pro Leu Gln Asp Leu Phe Cys
            290                 295                 300

Gln Ser Ser Glu Asp Asp Gly Ser Lys Leu Lys Thr Lys Met Lys Gly
305                 310                 315                 320

Val Cys Glu Val Gly Val Gln Ala Leu Lys Lys Cys Asp Gly Gln Leu
            325                 330                 335

Ser Thr Ala His Glu Val Val Pro Phe Ala Val Phe Lys Asn Ser Lys
            340                 345                 350

Lys Val Tyr Leu Asp Lys Leu Asp Leu Lys Thr Glu Glu Asn Leu Leu
            355                 360                 365

Pro Asp Ser Phe Val Cys Phe Glu His Lys Gly Gln Tyr Lys Gly Thr
            370                 375                 380

Met Asp Ser Gly Gln Thr Lys Arg Glu Leu Lys Ser Phe Asp Ile Ser
385                 390                 395                 400

Gln Cys Pro Lys Ile Gly Gly His Gly Ser Lys Lys Cys Thr Gly Asp
            405                 410                 415

Ala Ala Phe Cys Ser Ala Tyr Glu Cys Thr Ala Gln Tyr Ala Asn Ala
            420                 425                 430
```

```
Tyr Cys Ser His Ala Asn Gly Ser Gly Val Val Gln Ile Gln Val Ser
            435                 440                 445

Gly Val Trp Lys Lys Pro Leu Cys Val Gly Tyr Glu Arg Val Val
    450                 455                 460

Lys Arg Glu Leu Ser Ala Lys Pro Ile Gln Arg Val Glu Pro Cys Thr
465                 470                 475                 480

Thr Cys Ile Thr Lys Cys Glu Pro His Gly Leu Val Val Arg Ser Thr
                485                 490                 495

Gly Phe Lys Ile Ser Ser Ala Val Ala Cys Ala Ser Gly Val Cys Val
                500                 505                 510

Thr Gly Ser Gln Ser Pro Ser Thr Glu Ile Thr Leu Lys Tyr Pro Gly
            515                 520                 525

Ile Ser Gln Ser Ser Gly Gly Asp Ile Gly Val His Met Ala His Asp
    530                 535                 540

Asp Gln Ser Val Ser Ser Lys Ile Val Ala His Cys Pro Pro Gln Asp
545                 550                 555                 560

Pro Cys Leu Val His Gly Cys Ile Val Cys Ala His Gly Leu Ile Asn
                565                 570                 575

Tyr Gln Cys His Thr Ala Leu Ser Ala Phe Val Val Phe Val Phe
                580                 585                 590

Ser Ser Val Ala Ile Ile Cys Leu Ala Ile Leu Tyr Lys Val Leu Lys
            595                 600                 605

Cys Leu Lys Ile Ala Pro Arg Lys Val Leu Asp Pro Leu Met Trp Ile
    610                 615                 620

Thr Val Phe Ile Arg Trp Val Tyr Lys Lys Met Val Ala Arg Val Ala
625                 630                 635                 640

Asp Asn Ile Asn Gln Val Asn Arg Glu Ile Gly Trp Met Glu Gly Gly
                645                 650                 655

Gln Leu Ala Leu Gly Asn Pro Ala Pro Ile Pro Arg His Ala Pro Ile
                660                 665                 670

Pro Arg

<210> SEQ ID NO 14
<211> LENGTH: 922
<212> TYPE: DNA
<213> ORGANISM: Artificial Sequence
<220> FEATURE:
<223> OTHER INFORMATION: pUC57-S-delNSs
<220> FEATURE:
<221> NAME/KEY: CDS
<222> LOCATION: (39)..(776)

<400> SEQUENCE: 14
acacaaagct ccctagagat acaaacacta ttacaata atg gac aac tat caa gag    56
                                          Met Asp Asn Tyr Gln Glu
                                            1               5 ctt gcg atc cag ttt gct gct caa gca gtg gac cgc aat gag att gaa    104
Leu Ala Ile Gln Phe Ala Ala Gln Ala Val Asp Arg Asn Glu Ile Glu
        10                  15                  20 cag tgg gtc cga gag ttt gct tat caa gga ttt gat gcc cgt agg gtt    152
Gln Trp Val Arg Glu Phe Ala Tyr Gln Gly Phe Asp Ala Arg Arg Val
    25                  30                  35 atc gaa ctc tta aag cag tat ggt ggg gct gac tgg gag aag gat gcc    200
Ile Glu Leu Leu Lys Gln Tyr Gly Gly Ala Asp Trp Glu Lys Asp Ala
40                  45                  50 aag aaa atg att gtt ctg gct ctg act cgt ggc aac aag ccc cgg agg    248
Lys Lys Met Ile Val Leu Ala Leu Thr Arg Gly Asn Lys Pro Arg Arg
55                  60                  65                  70
```

```
atg atg atg aaa atg tcg aaa gaa ggc aaa gca act gtg gag gct ctc         296
Met Met Met Lys Met Ser Lys Glu Gly Lys Ala Thr Val Glu Ala Leu
            75                  80                  85 atc aac aag tat aag cta aag gag ggg aat cct tcc cgg gat gag ttg         344
Ile Asn Lys Tyr Lys Leu Lys Glu Gly Asn Pro Ser Arg Asp Glu Leu
        90                  95                  100 act cta tca cga gtt gct gct gcc ctg gct ggc tgg act tgc cag gct         392
Thr Leu Ser Arg Val Ala Ala Ala Leu Ala Gly Trp Thr Cys Gln Ala
        105                 110                 115 ttg gtc gtc ttg agt gag tgg ctt cct gtc act ggg acc acc atg gat         440
Leu Val Val Leu Ser Glu Trp Leu Pro Val Thr Gly Thr Thr Met Asp
    120                 125                 130 ggc cta tcc cct gca tac cca agg cat atg atg cac ccc agc ttt gct         488
Gly Leu Ser Pro Ala Tyr Pro Arg His Met Met His Pro Ser Phe Ala
135                 140                 145                 150 ggc atg gtg gac cct tct cta cca gaa gac tat cta agg gca ata ttg         536
Gly Met Val Asp Pro Ser Leu Pro Glu Asp Tyr Leu Arg Ala Ile Leu
                155                 160                 165 gat gct cac tct ctg tat ctg ctg cag ttc tcc cgg gtc atc aac cca         584
Asp Ala His Ser Leu Tyr Leu Leu Gln Phe Ser Arg Val Ile Asn Pro
            170                 175                 180 aac ctc cga ggt aga aca aag gag gag gtt gcc gca acg ttc acg cag         632
Asn Leu Arg Gly Arg Thr Lys Glu Glu Val Ala Ala Thr Phe Thr Gln
        185                 190                 195 cca atg aat gca gca gtg aat agc aac ttt ata agc cat gag aag agg         680
Pro Met Asn Ala Ala Val Asn Ser Asn Phe Ile Ser His Glu Lys Arg
        200                 205                 210 aga gaa ttc ttg aaa gct ttt ggg ctt gtg gat tcc aat ggg aag ccg         728
Arg Glu Phe Leu Lys Ala Phe Gly Leu Val Asp Ser Asn Gly Lys Pro
215                 220                 225                 230 tca gca gct gtc atg gca gct gct cag gcg tac aag aca gca gcc taa         776
Ser Ala Ala Val Met Ala Ala Ala Gln Ala Tyr Lys Thr Ala Ala
                235                 240                 245 gtggctgccc aggggtttgg ggaaaagggg gtggttgggg ttacggtcgg gattgggggt      836 gggggggtggg gcagccttaa tcttcaacag atatcacagg aaagtaatcc atgatatact     896
tgataagcac taggggtct ttgtgt                                            922

<210> SEQ ID NO 15
<211> LENGTH: 245
<212> TYPE: PRT
<213> ORGANISM: Artificial Sequence
<220> FEATURE:
<223> OTHER INFORMATION: Synthetic Construct

<400> SEQUENCE: 15

Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
            20                  25                  30

Phe Asp Ala Arg Arg Val Ile Glu Leu Leu Lys Gln Tyr Gly Gly Ala
        35                  40                  45

Asp Trp Glu Lys Asp Ala Lys Lys Met Ile Val Leu Ala Leu Thr Arg
    50                  55                  60

Gly Asn Lys Pro Arg Arg Met Met Met Lys Met Ser Lys Glu Gly Lys
65                  70                  75                  80

Ala Thr Val Glu Ala Leu Ile Asn Lys Tyr Lys Leu Lys Glu Gly Asn
                85                  90                  95
```

```
Pro Ser Arg Asp Glu Leu Thr Leu Ser Arg Val Ala Ala Ala Leu Ala
            100                 105                 110

Gly Trp Thr Cys Gln Ala Leu Val Val Leu Ser Glu Trp Leu Pro Val
        115                 120                 125

Thr Gly Thr Thr Met Asp Gly Leu Ser Pro Ala Tyr Pro Arg His Met
    130                 135                 140

Met His Pro Ser Phe Ala Gly Met Val Asp Pro Ser Leu Pro Glu Asp
145                 150                 155                 160

Tyr Leu Arg Ala Ile Leu Asp Ala His Ser Leu Tyr Leu Leu Gln Phe
                165                 170                 175

Ser Arg Val Ile Asn Pro Asn Leu Arg Gly Arg Thr Lys Glu Glu Val
            180                 185                 190

Ala Ala Thr Phe Thr Gln Pro Met Asn Ala Ala Val Asn Ser Asn Phe
        195                 200                 205

Ile Ser His Glu Lys Arg Arg Glu Phe Leu Lys Ala Phe Gly Leu Val
    210                 215                 220

Asp Ser Asn Gly Lys Pro Ser Ala Ala Val Met Ala Ala Ala Gln Ala
225                 230                 235                 240

Tyr Lys Thr Ala Ala
            245
```

<210> SEQ ID NO 16
<211> LENGTH: 2319
<212> TYPE: DNA
<213> ORGANISM: Artificial Sequence
<220> FEATURE:
<223> OTHER INFORMATION: pUC57-M-NSmGn

<400> SEQUENCE: 16

```
acacaaagac ggtgcattaa atgtatgttt tactaacaat tctgatcacg gttctggtgt    60
gtgaggcggt tattagagtg tctctaagtt ccacaagaga agagacctgc tttggtgact   120
acaccaaccc agagatgatt gaaggagctt gggattcact cagagaggag agatgccag   180
aggagctctc ctgttccata tcaggcataa gggaggtcaa aacctcaagc caggaattgt   240
atagggcatt aaaagccatc attgctgctg atggcttgaa caacatcacc tgccatggta   300
aggatcctga ggataagatt tctctcgtaa agggtcctcc tcacaaaaag cgggtgggga   360
tagttcggtg tgagagacga agagacgcta agcaaatagg aagagaaacc atggcaggga   420
ttgcaatgac agtccttcca gccttagcag ttttgctttg gcacctgtt gtttttgctg   480
aagaccctca tctcagaaac agaccaggga aggggcacaa ctacattgac gggatgactc   540
aggaggacgc cacatgcaaa cctgtgacat atgctggggc ttgtagcagt tttgatgtct   600
tgctcgaaaa gggaaaattc cccctcttcc agtcgtatgc ccatcacaga acccta ctag   660
aagcagttca cgacaccatc attgcaaagg ctgatccacc tagctgtgac cttcagagtg   720
ctcatgggaa tccctgcatg aaggagaaac tcgtgatgaa gacacactgt ccaaatgact   780
accagtcagc tcattacctc aacaatgacg ggaaaatggc ttcagtcaag tgccctccta   840
aatatgagct cactgaggac tgcaattttt gcaggcagat gacaggtgct agcttgaaga   900
aggggtctta tcctcttcag gacttatttt gtcagtcaag tgaggatgat ggatcaaaat   960
taaaaacaaa aatgaaaggg gtctgcgaag tgggggttca agcactcaaa aagtgtgatg  1020
gccaactcag cactgcacat gaggttgtgc cctttgcagt atttaagaac tcaaagaagg  1080
tttatcttga taagcttgac ctcaagactg aggaaaatct gttgccagac tcatttgtct  1140
gcttcgagca taagggacag tataaaggaa caatggactc tggtcagacc aagagggagc  1200
```

-continued

```
tcaaaagctt tgatatctct cagtgcccca agattggagg acatggtagc aagaagtgca   1260
ctggggacgc agctttttgc tctgcttatg agtgcactgc tcaatacgcc aatgcttatt   1320
gttcacatgc taatgggtca ggagttgtac agatacaagt atccggggtc tggaagaagc   1380
ctttgtgtgt cgggtatgag agggtggttg tgaagagaga actctctgct aagcccatcc   1440
agagagttga gccttgcaca acttgtataa ccaaatgtga gcctcacgga ttggttgtcc   1500
gatcaacagg tttcaagata tcatctgcag ttgcttgtgc tagcggagtt tgcgttacag   1560
gatcgcagag cccttctacc gagattacac tcaagtatcc agggatatcc cagtcctctg   1620
ggggggacat aggggttcac atggcacatg atgatcagtc agttagctcc aaaatagtag   1680
ctcactgccc tccccaggat ccatgcctag tgcatggctg catagtgtgt gctcatggcc   1740
tgataaatta ccagtgtcac actgctctca gtgcctttgt tgttgtgttc gtatttagct   1800
ctgtcgcaat aatttgtttg gccattcttt ataaagttct caagtgccta aagattgccc   1860
caaggaaagt tctggatcca ctaatgtgga ttactgtttt catcagatgg gtgtataaga   1920
agatggttgc cagagtagca gacaatatca atcaggtgaa cagggaaata ggatggatgg   1980
aaggaggcca gctggctcta gggaaccctg cccctattcc tcgtcatgct ccaattccac   2040
gttagtagat cagtacgtgt agaagcaata tatagaaata agtaaacata agcaaatcta   2100
attatgtaaa tattgtacag atgggtcaaa ctattgggat atccaagttt agaatcttgt   2160
acaatagtac tttagatgta agcttagttg taatttgggg tggtggggtg aggcagcagt   2220
agtctcaagt acatgtggat attctagtta atgtgaatgt cttttgccag attagctggg   2280
aattaaacta actctttgaa gttgcaccgg tctttgtgt                          2319
```

```

<210> SEQ ID NO 17
<211> LENGTH: 674
<212> TYPE: PRT
<213> ORGANISM: Artificial Sequence
<220> FEATURE:
<223> OTHER INFORMATION: protein encoded by reverse strand of
      pUC57-M-NSmGn

<400> SEQUENCE: 17

Met Tyr Val Leu Leu Thr Ile Leu Ile Thr Val Leu Val Cys Glu Ala
1               5                   10                  15

Val Ile Arg Val Ser Leu Ser Ser Thr Arg Glu Glu Thr Cys Phe Gly
            20                  25                  30

Asp Tyr Thr Asn Pro Glu Met Ile Glu Gly Ala Trp Asp Ser Leu Arg
        35                  40                  45

Glu Glu Glu Met Pro Glu Glu Leu Ser Cys Ser Ile Ser Gly Ile Arg
    50                  55                  60

Glu Val Lys Thr Ser Ser Gln Glu Leu Tyr Arg Ala Leu Lys Ala Ile
65                  70                  75                  80

Ile Ala Ala Asp Gly Leu Asn Asn Ile Thr Cys His Gly Lys Asp Pro
                85                  90                  95

Glu Asp Lys Ile Ser Leu Val Lys Gly Pro Pro His Lys Lys Arg Val
            100                 105                 110

Gly Ile Val Arg Cys Glu Arg Arg Arg Asp Ala Lys Gln Ile Gly Arg
        115                 120                 125

Glu Thr Met Ala Gly Ile Ala Met Thr Val Leu Pro Ala Leu Ala Val
    130                 135                 140

Phe Ala Leu Ala Pro Val Val Phe Ala Glu Asp Pro His Leu Arg Asn
145                 150                 155                 160
```

-continued

Arg Pro Gly Lys Gly His Asn Tyr Ile Asp Gly Met Thr Gln Glu Asp
            165                 170                 175

Ala Thr Cys Lys Pro Val Thr Tyr Ala Gly Ala Cys Ser Ser Phe Asp
            180                 185                 190

Val Leu Leu Glu Lys Gly Lys Phe Pro Leu Phe Gln Ser Tyr Ala His
            195                 200                 205

His Arg Thr Leu Leu Glu Ala Val His Asp Thr Ile Ile Ala Lys Ala
            210                 215                 220

Asp Pro Pro Ser Cys Asp Leu Gln Ser Ala His Gly Asn Pro Cys Met
225                 230                 235                 240

Lys Glu Lys Leu Val Met Lys Thr His Cys Pro Asn Asp Tyr Gln Ser
            245                 250                 255

Ala His Tyr Leu Asn Asn Asp Gly Lys Met Ala Ser Val Lys Cys Pro
            260                 265                 270

Pro Lys Tyr Glu Leu Thr Glu Asp Cys Asn Phe Cys Arg Gln Met Thr
            275                 280                 285

Gly Ala Ser Leu Lys Lys Gly Ser Tyr Pro Leu Gln Asp Leu Phe Cys
            290                 295                 300

Gln Ser Ser Glu Asp Asp Gly Ser Lys Leu Lys Thr Lys Met Lys Gly
305                 310                 315                 320

Val Cys Glu Val Gly Val Gln Ala Leu Lys Lys Cys Asp Gly Gln Leu
            325                 330                 335

Ser Thr Ala His Glu Val Val Pro Phe Ala Val Phe Lys Asn Ser Lys
            340                 345                 350

Lys Val Tyr Leu Asp Lys Leu Asp Leu Lys Thr Glu Glu Asn Leu Leu
            355                 360                 365

Pro Asp Ser Phe Val Cys Phe Glu His Lys Gly Gln Tyr Lys Gly Thr
            370                 375                 380

Met Asp Ser Gly Gln Thr Lys Arg Glu Leu Lys Ser Phe Asp Ile Ser
385                 390                 395                 400

Gln Cys Pro Lys Ile Gly Gly His Gly Ser Lys Lys Cys Thr Gly Asp
            405                 410                 415

Ala Ala Phe Cys Ser Ala Tyr Glu Cys Thr Ala Gln Tyr Ala Asn Ala
            420                 425                 430

Tyr Cys Ser His Ala Asn Gly Ser Gly Val Val Gln Ile Gln Val Ser
            435                 440                 445

Gly Val Trp Lys Lys Pro Leu Cys Val Gly Tyr Glu Arg Val Val Val
            450                 455                 460

Lys Arg Glu Leu Ser Ala Lys Pro Ile Gln Arg Val Glu Pro Cys Thr
465                 470                 475                 480

Thr Cys Ile Thr Lys Cys Glu Pro His Gly Leu Val Val Arg Ser Thr
            485                 490                 495

Gly Phe Lys Ile Ser Ser Ala Val Ala Cys Ala Ser Gly Val Cys Val
            500                 505                 510

Thr Gly Ser Gln Ser Pro Ser Thr Glu Ile Thr Leu Lys Tyr Pro Gly
            515                 520                 525

Ile Ser Gln Ser Ser Gly Gly Asp Ile Gly Val His Met Ala His Asp
            530                 535                 540

Asp Gln Ser Val Ser Ser Lys Ile Val Ala His Cys Pro Pro Gln Asp
545                 550                 555                 560

Pro Cys Leu Val His Gly Cys Ile Val Cys Ala His Gly Leu Ile Asn
            565                 570                 575

```
Tyr Gln Cys His Thr Ala Leu Ser Ala Phe Val Val Phe Val Phe
            580                 585                 590

Ser Ser Val Ala Ile Ile Cys Leu Ala Ile Leu Tyr Lys Val Leu Lys
        595                 600                 605

Cys Leu Lys Ile Ala Pro Arg Lys Val Leu Asp Pro Leu Met Trp Ile
610                 615                 620

Thr Val Phe Ile Arg Trp Val Tyr Lys Lys Met Val Ala Arg Val Ala
625                 630                 635                 640

Asp Asn Ile Asn Gln Val Asn Arg Glu Ile Gly Trp Met Glu Gly Gly
                645                 650                 655

Gln Leu Ala Leu Gly Asn Pro Ala Pro Ile Pro Arg His Ala Pro Ile
            660                 665                 670

Pro Arg

<210> SEQ ID NO 18
<211> LENGTH: 1869
<212> TYPE: DNA
<213> ORGANISM: Artificial Sequence
<220> FEATURE:
<223> OTHER INFORMATION: pUC57-M-Gc
<220> FEATURE:
<221> NAME/KEY: CDS
<222> LOCATION: (24)..(1598)

<400> SEQUENCE: 18
acacaaagac ggtgcattaa acc atg tat agc aca tac cta atg cta cta ttg      53
                        Met Tyr Ser Thr Tyr Leu Met Leu Leu Leu
                          1               5                  10 att gtc tca tat gca tca gca tgt tca gaa ctg att cag gca agc tcc     101
Ile Val Ser Tyr Ala Ser Ala Cys Ser Glu Leu Ile Gln Ala Ser Ser
             15                  20                  25 aga atc acc act tgc tcc aca gaa ggt gtc aac acc aag tgt agg ctg     149
Arg Ile Thr Thr Cys Ser Thr Glu Gly Val Asn Thr Lys Cys Arg Leu
         30                  35                  40 tct ggc aca gca tta atc agg gca ggg tca gtt ggg gca gag gct tgt     197
Ser Gly Thr Ala Leu Ile Arg Ala Gly Ser Val Gly Ala Glu Ala Cys
     45                  50                  55 ttg atg tta aag ggg gtc aag gaa gac caa acc aag ttt ttg aag ata     245
Leu Met Leu Lys Gly Val Lys Glu Asp Gln Thr Lys Phe Leu Lys Ile
 60                  65                  70 aaa act gtc tca agt gag cta tcg tgc agg gag ggc cag agc tat tgg     293
Lys Thr Val Ser Ser Glu Leu Ser Cys Arg Glu Gly Gln Ser Tyr Trp
 75                  80                  85                  90 act ggg tcc ttt agc cct aaa tgt ctg agc tca agg aga tgc cat ctt     341
Thr Gly Ser Phe Ser Pro Lys Cys Leu Ser Ser Arg Arg Cys His Leu
                 95                 100                 105 gtc ggg gaa tgt cat gtg aat agg tgt ctg tct tgg aga gac aat gaa     389
Val Gly Glu Cys His Val Asn Arg Cys Leu Ser Trp Arg Asp Asn Glu
            110                 115                 120 acc tca gca gaa ttt tca ttt gtt ggg gaa agc acg acc atg cgg gag     437
Thr Ser Ala Glu Phe Ser Phe Val Gly Glu Ser Thr Thr Met Arg Glu
        125                 130                 135 aac aag tgt ttt gag cag tgt gga gga tgg gga tgt ggg tgt ttc aat     485
Asn Lys Cys Phe Glu Gln Cys Gly Gly Trp Gly Cys Gly Cys Phe Asn
    140                 145                 150 gtg aac cca tct tgc tta ttt gtg cac acg tat ctg cag tca gtc aga     533
Val Asn Pro Ser Cys Leu Phe Val His Thr Tyr Leu Gln Ser Val Arg
155                 160                 165                 170 aaa gag gcc ctt aga gtt ttc aac tgt atc gat tgg gtg cat aaa ctc     581
Lys Glu Ala Leu Arg Val Phe Asn Cys Ile Asp Trp Val His Lys Leu
```

```
                    175                 180                 185
act cta gag att act gac ttt gat ggc tct gtt tca aca ata gac ctg         629
Thr Leu Glu Ile Thr Asp Phe Asp Gly Ser Val Ser Thr Ile Asp Leu
            190                 195                 200 gga gca tca tct agc cgt ttc aca aac tgg ggt tca gtt agc ctc tca         677
Gly Ala Ser Ser Ser Arg Phe Thr Asn Trp Gly Ser Val Ser Leu Ser
        205                 210                 215 ctg gac gca gag ggc att tca ggc tca aac agc ttt tcc ttc att gag         725
Leu Asp Ala Glu Gly Ile Ser Gly Ser Asn Ser Phe Ser Phe Ile Glu
    220                 225                 230 agc cca ggc aaa ggg tat gca att gtt gat gag cca ttc tca gaa att         773
Ser Pro Gly Lys Gly Tyr Ala Ile Val Asp Glu Pro Phe Ser Glu Ile
235                 240                 245                 250 cct cgg caa ggg ttc ttg ggg gag atc agg tgc aat tca gaa tct tca         821
Pro Arg Gln Gly Phe Leu Gly Glu Ile Arg Cys Asn Ser Glu Ser Ser
                255                 260                 265 gtc ctg agt gct cat gaa tca tgc ctt agg gca cca aat ctt att tca         869
Val Leu Ser Ala His Glu Ser Cys Leu Arg Ala Pro Asn Leu Ile Ser
            270                 275                 280 tac aag ccc atg ata gat cag ttg gag tgc aca aca aat ctg att gat         917
Tyr Lys Pro Met Ile Asp Gln Leu Glu Cys Thr Thr Asn Leu Ile Asp
        285                 290                 295 ccc ttt gtt gtc ttt gag agg ggc tct ctg cca cag aca agg aat gac         965
Pro Phe Val Val Phe Glu Arg Gly Ser Leu Pro Gln Thr Arg Asn Asp
    300                 305                 310 aaa acc ttt gca gct tca aaa gga aat agg ggt gtt caa gct ttc tct        1013
Lys Thr Phe Ala Ala Ser Lys Gly Asn Arg Gly Val Gln Ala Phe Ser
315                 320                 325                 330 aag ggc tct gta cag gct gat cta aca ctg atg ttt gac aat ttt gag        1061
Lys Gly Ser Val Gln Ala Asp Leu Thr Leu Met Phe Asp Asn Phe Glu
                335                 340                 345 gtg gac ttt gtg gga gca gcc gtg tct tgt gat gcc gcc ttc tta aat        1109
Val Asp Phe Val Gly Ala Ala Val Ser Cys Asp Ala Ala Phe Leu Asn
            350                 355                 360 ttg aca ggt tgc tat tcc tgc aat gca ggg gcc aga gtc tgc ctg tct        1157
Leu Thr Gly Cys Tyr Ser Cys Asn Ala Gly Ala Arg Val Cys Leu Ser
        365                 370                 375 atc aca tcc aca gga act gga act ctc tct gcc cac aat aaa gat gga        1205
Ile Thr Ser Thr Gly Thr Gly Thr Leu Ser Ala His Asn Lys Asp Gly
    380                 385                 390 tct ctg cat ata gtt ctt cca tca gag aat gga aca aaa gat cag tgt        1253
Ser Leu His Ile Val Leu Pro Ser Glu Asn Gly Thr Lys Asp Gln Cys
395                 400                 405                 410 cag ata cta cac ttc act gta cct gag gta gag gag gag ttt atg tac        1301
Gln Ile Leu His Phe Thr Val Pro Glu Val Glu Glu Glu Phe Met Tyr
                415                 420                 425 tct tgt gat gga gat gag cgg cct ctg ttg gtg aag gga acc ctg ata        1349
Ser Cys Asp Gly Asp Glu Arg Pro Leu Leu Val Lys Gly Thr Leu Ile
            430                 435                 440 gct att gat cca ttt gat gat agg cga gaa gca ggg ggg gaa tca aca        1397
Ala Ile Asp Pro Phe Asp Asp Arg Arg Glu Ala Gly Gly Glu Ser Thr
        445                 450                 455 gtt gtg aat cca aaa tct gga tct tgg aat ttc ttt gac tgg ttt tct        1445
Val Val Asn Pro Lys Ser Gly Ser Trp Asn Phe Phe Asp Trp Phe Ser
    460                 465                 470 gga ctc atg agt tgg ttt gga ggg cct ctt aag act ata ctc ctc att        1493
Gly Leu Met Ser Trp Phe Gly Gly Pro Leu Lys Thr Ile Leu Leu Ile
475                 480                 485                 490 tgc ctg tat gta gca tta tca att ggg ctc ttt ttc ctt ctt ata tat        1541
```

```
Cys Leu Tyr Val Ala Leu Ser Ile Gly Leu Phe Phe Leu Leu Ile Tyr
                495                 500                 505 ctt gga aga aca ggc ctc tct aaa atg tgg ctt gct gcc acc aag aaa    1589
Leu Gly Arg Thr Gly Leu Ser Lys Met Trp Leu Ala Ala Thr Lys Lys
        510                 515                 520 gcc tca tag atcagtacgt gtagaagcaa tatatagaaa taagtaaaca             1638
Ala Ser taagcaaatc taattatgta aatattgtac agatgggtca aactattggg atatccaagt  1698
ttagaatctt gtacaatagt actttagatg taagcttagt tgtaatttgg ggtggtgggg  1758
tgaggcagca gtagtctcaa gtacatgtgg atattctagt taatgtgaat gtcttttgcc  1818
agattagctg ggaattaaac taactctttg aagttgcacc ggtctttgtg t            1869

<210> SEQ ID NO 19
<211> LENGTH: 524
<212> TYPE: PRT
<213> ORGANISM: Artificial Sequence
<220> FEATURE:
<223> OTHER INFORMATION: Synthetic Construct

<400> SEQUENCE: 19

Met Tyr Ser Thr Tyr Leu Met Leu Leu Ile Val Ser Tyr Ala Ser
1               5                   10                  15

Ala Cys Ser Glu Leu Ile Gln Ala Ser Ser Arg Ile Thr Thr Cys Ser
            20                  25                  30

Thr Glu Gly Val Asn Thr Lys Cys Arg Leu Ser Gly Thr Ala Leu Ile
        35                  40                  45

Arg Ala Gly Ser Val Gly Ala Glu Ala Cys Leu Met Leu Lys Gly Val
    50                  55                  60

Lys Glu Asp Gln Thr Lys Phe Leu Lys Ile Lys Thr Val Ser Ser Glu
65                  70                  75                  80

Leu Ser Cys Arg Glu Gly Gln Ser Tyr Trp Thr Gly Ser Phe Ser Pro
                85                  90                  95

Lys Cys Leu Ser Ser Arg Arg Cys His Leu Val Gly Glu Cys His Val
            100                 105                 110

Asn Arg Cys Leu Ser Trp Arg Asp Asn Glu Thr Ser Ala Glu Phe Ser
        115                 120                 125

Phe Val Gly Glu Ser Thr Thr Met Arg Glu Asn Lys Cys Phe Glu Gln
    130                 135                 140

Cys Gly Gly Trp Gly Cys Gly Cys Phe Asn Val Asn Pro Ser Cys Leu
145                 150                 155                 160

Phe Val His Thr Tyr Leu Gln Ser Val Arg Lys Glu Ala Leu Arg Val
                165                 170                 175

Phe Asn Cys Ile Asp Trp Val His Lys Leu Thr Leu Glu Ile Thr Asp
            180                 185                 190

Phe Asp Gly Ser Val Ser Thr Ile Asp Leu Gly Ala Ser Ser Arg
        195                 200                 205

Phe Thr Asn Trp Gly Ser Val Ser Leu Ser Leu Asp Ala Glu Gly Ile
    210                 215                 220

Ser Gly Ser Asn Ser Phe Ser Phe Ile Glu Ser Pro Gly Lys Gly Tyr
225                 230                 235                 240

Ala Ile Val Asp Glu Pro Phe Ser Glu Ile Pro Arg Gln Gly Phe Leu
                245                 250                 255

Gly Glu Ile Arg Cys Asn Ser Glu Ser Ser Val Leu Ser Ala His Glu
            260                 265                 270
```

Ser Cys Leu Arg Ala Pro Asn Leu Ile Ser Tyr Lys Pro Met Ile Asp
            275                 280                 285

Gln Leu Glu Cys Thr Thr Asn Leu Ile Asp Pro Phe Val Val Phe Glu
        290                 295                 300

Arg Gly Ser Leu Pro Gln Thr Arg Asn Asp Lys Thr Phe Ala Ala Ser
305                 310                 315                 320

Lys Gly Asn Arg Gly Val Gln Ala Phe Ser Lys Gly Ser Val Gln Ala
                325                 330                 335

Asp Leu Thr Leu Met Phe Asp Asn Phe Glu Val Asp Phe Val Gly Ala
            340                 345                 350

Ala Val Ser Cys Asp Ala Ala Phe Leu Asn Leu Thr Gly Cys Tyr Ser
        355                 360                 365

Cys Asn Ala Gly Ala Arg Val Cys Leu Ser Ile Thr Ser Thr Gly Thr
    370                 375                 380

Gly Thr Leu Ser Ala His Asn Lys Asp Gly Ser Leu His Ile Val Leu
385                 390                 395                 400

Pro Ser Glu Asn Gly Thr Lys Asp Gln Cys Gln Ile Leu His Phe Thr
                405                 410                 415

Val Pro Glu Val Glu Glu Phe Met Tyr Ser Cys Asp Gly Asp Glu
            420                 425                 430

Arg Pro Leu Leu Val Lys Gly Thr Leu Ile Ala Ile Asp Pro Phe Asp
        435                 440                 445

Asp Arg Arg Glu Ala Gly Gly Glu Ser Thr Val Val Asn Pro Lys Ser
    450                 455                 460

Gly Ser Trp Asn Phe Phe Asp Trp Phe Ser Gly Leu Met Ser Trp Phe
465                 470                 475                 480

Gly Gly Pro Leu Lys Thr Ile Leu Leu Ile Cys Leu Tyr Val Ala Leu
                485                 490                 495

Ser Ile Gly Leu Phe Phe Leu Leu Ile Tyr Leu Gly Arg Thr Gly Leu
            500                 505                 510

Ser Lys Met Trp Leu Ala Ala Thr Lys Lys Ala Ser
        515                 520

<210> SEQ ID NO 20
<211> LENGTH: 2357
<212> TYPE: DNA
<213> ORGANISM: Artificial Sequence
<220> FEATURE:
<223> OTHER INFORMATION: pUC57-S-CCHFV-N
<220> FEATURE:
<221> NAME/KEY: CDS
<222> LOCATION: (39)..(788)

<400> SEQUENCE: 20
acacaaagct ccctagagat acaaacacta ttacaata atg gac aac tat caa gag        56
                                          Met Asp Asn Tyr Gln Glu
                                            1               5 ctt gcg atc cag ttt gct gct caa gca gtg gac cgc aat gag att gaa      104
Leu Ala Ile Gln Phe Ala Ala Gln Ala Val Asp Arg Asn Glu Ile Glu
         10                  15                  20 cag tgg gtc cga gag ttt gct tat caa gga ttt gat gcc cgt agg gtt      152
Gln Trp Val Arg Glu Phe Ala Tyr Gln Gly Phe Asp Ala Arg Arg Val
     25                  30                  35 atc gaa ctc tta aag cag tat ggt ggg gct gac tgg gag aag gat gcc      200
Ile Glu Leu Leu Lys Gln Tyr Gly Gly Ala Asp Trp Glu Lys Asp Ala
 40                  45                  50 aag aaa atg att gtt ctg gct ctg act cgt ggc aac aag ccc cgg agg      248
Lys Lys Met Ile Val Leu Ala Leu Thr Arg Gly Asn Lys Pro Arg Arg

|  |  |  |  |  |  |  |  |  |  |  |  |  |  |  |
|---|---|---|---|---|---|---|---|---|---|---|---|---|---|---|
| 55 |  |  |  |  | 60 |  |  |  | 65 |  |  |  | 70 |  |

```
atg atg atg aaa atg tcg aaa gaa ggc aaa gca act gtg gag gct ctc        296
Met Met Met Lys Met Ser Lys Glu Gly Lys Ala Thr Val Glu Ala Leu
             75                  80                  85 atc aac aag tat aag cta aag gag ggg aat cct tcc cgg gat gag ttg        344
Ile Asn Lys Tyr Lys Leu Lys Glu Gly Asn Pro Ser Arg Asp Glu Leu
             90                  95                 100 act cta tca cga gtt gct gct gcc ctg gct ggc tgg act tgc cag gct        392
Thr Leu Ser Arg Val Ala Ala Ala Leu Ala Gly Trp Thr Cys Gln Ala
            105                 110                 115 ttg gtc gtc ttg agt gag tgg ctt cct gtc act ggg acc act atg gat        440
Leu Val Val Leu Ser Glu Trp Leu Pro Val Thr Gly Thr Thr Met Asp
            120                 125                 130 ggc cta tcc cct gca tac cca agg cat atg atg cac ccc agc ttt gct        488
Gly Leu Ser Pro Ala Tyr Pro Arg His Met Met His Pro Ser Phe Ala
135                 140                 145                 150 ggc atg gtg gac cct tct cta cca gaa gac tat cta agg gca ata ttg        536
Gly Met Val Asp Pro Ser Leu Pro Glu Asp Tyr Leu Arg Ala Ile Leu
                155                 160                 165 gat gct cac tct ctg tat ctg ctg cag ttc tcc cgg gtc atc aac cca        584
Asp Ala His Ser Leu Tyr Leu Leu Gln Phe Ser Arg Val Ile Asn Pro
            170                 175                 180 aac ctc cga ggt aga aca aag gag gag gtt gcc gca acg ttc acg cag        632
Asn Leu Arg Gly Arg Thr Lys Glu Glu Val Ala Ala Thr Phe Thr Gln
            185                 190                 195 cca atg aat gca gca gtg aat agc aac ttt ata agc cat gag aag agg        680
Pro Met Asn Ala Ala Val Asn Ser Asn Phe Ile Ser His Glu Lys Arg
200                 205                 210 aga gaa ttc ttg aaa gct ttt ggg ctt gtg gat tcc aat ggg aag ccg        728
Arg Glu Phe Leu Lys Ala Phe Gly Leu Val Asp Ser Asn Gly Lys Pro
215                 220                 225                 230 tca gca gct gtc atg gca gct gct cag gcg tac aag aca gca gcc taa        776
Ser Ala Ala Val Met Ala Ala Ala Gln Ala Tyr Lys Thr Ala Ala
                235                 240                 245 gtg gct gcc cag gggtttgggg aaaaggggt ggttggggtt acggtcggga             828
Val Ala Ala Gln ttggggggtgg ggggtggggc agccttaatc ttctagatta gatgatgttg gcactggtgg     888
cgttgccctt cacgttgtag gcgttctgga atggggactg cttcccacc agggactgat      948 gcagcaggtg ctcgctggcc acaatgtcca tatcctggat gttaaagccc gtcttctgca    1008
cctcgaacag cttcacgatg gtcttggcgc acggattgtt tgtctccgta ttggtgcgca    1068
ggttcagaat ggacttggta tgtccgcttc cctgggcggc gtcatctgga ttggccactg    1128
gaatggttcc gaagcacacg cccatctcgc tgatgcgtcc ggctgtcagc acggctgggt    1188
gcatatagat gcggttctgc tgaaaggagt catcggcgaa cagctcgtac agcttcttgc    1248
cccacttcat gggtgtgctc agcagggcct tcttcatctt cttcgttccg cgtggctgct    1308
tgcccagctc aaacaggaac tggctcactg ttgggaaggt ctctgggtc actccggcct     1368 tatacagcca atagtaggag ctgaaggcgg tatcaatctg gccgactgg gcgcgcaggg     1428 cactgctgtt cttgtacagc tcctgggcct tggcaatatg cttcagcagg ttcgtgatca    1488
tactgtcggc cgaggcgcgg tccacctcat ccttgtgctt atccagatat ccattcaggg    1548
cctccacggt cttcttggcc tcgtcgaaga ttcccttgcc ctccgtctcg gccagcttgg    1608
ccaggccggt ggccaccagg gcaattccgc tgcggccgga cttattgata tctccccacg    1668 ggggggttaaa ggccataatg tacttgccct tcacgaactc gcggcaccag tccacatgct    1728
```

```
cgtgcgacac gggtccgcgt ggattctcat ctcctccgcg attcagaatc aggttgcggc    1788
gacggatcat gtcactcagc atctccttca ccgacatcac gatctcgccc ggcaccttgt    1848
actcggccag caccttgttg gacagggcgg ccgtattggc gttcacgcgg aatccgatat    1908
ccttgcgcca cttcagggcg gcctgctgat agccggtcag ctgctcaatc ttgggcacgt    1968
ccaccttcag ctcggtgtaa ctctcatccc acgacttgat tgtgccggcg ttcttctcaa    2028
accactccag tcccttcttc acaatgcctg tggagctcac ccaggcgcac tcatagattg    2088
gggcgcagaa cttcgtggcc tccaccaggg cggaggcgta gatgctgtcc ttctgggcgt    2148
catccgtggc actggccatc tgaaacacga agcgatccag attcggcacc gactcgcaaa    2208
aactgtacga gtttgtgaac gtatccacca gtccatttcc cttcttaaac tcctcaaacc    2268
agcggttcat ctcatccttg ttgttcacct caatcttgtt ctccatggta ctagtgatat    2328
acttgataag cactaggggg tctttgtgt                                      2357
```

<210> SEQ ID NO 21
<211> LENGTH: 245
<212> TYPE: PRT
<213> ORGANISM: Artificial Sequence
<220> FEATURE:
<223> OTHER INFORMATION: Synthetic Construct

<400> SEQUENCE: 21

```
Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
            20                  25                  30

Phe Asp Ala Arg Arg Val Ile Glu Leu Leu Lys Gln Tyr Gly Gly Ala
        35                  40                  45

Asp Trp Glu Lys Asp Ala Lys Lys Met Ile Val Leu Ala Leu Thr Arg
    50                  55                  60

Gly Asn Lys Pro Arg Arg Met Met Met Lys Met Ser Lys Glu Gly Lys
65                  70                  75                  80

Ala Thr Val Glu Ala Leu Ile Asn Lys Tyr Lys Leu Lys Glu Gly Asn
                85                  90                  95

Pro Ser Arg Asp Glu Leu Thr Leu Ser Arg Val Ala Ala Ala Leu Ala
            100                 105                 110

Gly Trp Thr Cys Gln Ala Leu Val Val Leu Ser Glu Trp Leu Pro Val
        115                 120                 125

Thr Gly Thr Thr Met Asp Gly Leu Ser Pro Ala Tyr Pro Arg His Met
    130                 135                 140

Met His Pro Ser Phe Ala Gly Met Val Asp Pro Ser Leu Pro Glu Asp
145                 150                 155                 160

Tyr Leu Arg Ala Ile Leu Asp Ala His Ser Leu Tyr Leu Leu Gln Phe
                165                 170                 175

Ser Arg Val Ile Asn Pro Asn Leu Arg Gly Arg Thr Lys Glu Glu Val
            180                 185                 190

Ala Ala Thr Phe Thr Gln Pro Met Asn Ala Ala Val Asn Ser Asn Phe
        195                 200                 205

Ile Ser His Glu Lys Arg Arg Glu Phe Leu Lys Ala Phe Gly Leu Val
    210                 215                 220

Asp Ser Asn Gly Lys Pro Ser Ala Ala Val Met Ala Ala Gln Ala
225                 230                 235                 240

Tyr Lys Thr Ala Ala
            245
```

<210> SEQ ID NO 22
<211> LENGTH: 4
<212> TYPE: PRT
<213> ORGANISM: Artificial Sequence
<220> FEATURE:
<223> OTHER INFORMATION: Synthetic Construct

<400> SEQUENCE: 22

Val Ala Ala Gln
1

<210> SEQ ID NO 23
<211> LENGTH: 482
<212> TYPE: PRT
<213> ORGANISM: Artificial Sequence
<220> FEATURE:
<223> OTHER INFORMATION: protein encoded by contemplementary strand of
      pUC57-S-CCHFV-N

<400> SEQUENCE: 23

Met Glu Asn Lys Ile Glu Val Asn Asn Lys Asp Glu Met Asn Arg Trp
1               5                   10                  15

Phe Glu Glu Phe Lys Lys Gly Asn Gly Leu Val Asp Thr Phe Thr Asn
            20                  25                  30

Ser Tyr Ser Phe Cys Glu Ser Val Pro Asn Leu Asp Arg Phe Val Phe
        35                  40                  45

Gln Met Ala Ser Ala Thr Asp Asp Ala Gln Lys Asp Ser Ile Tyr Ala
    50                  55                  60

Ser Ala Leu Val Glu Ala Thr Lys Phe Cys Ala Pro Ile Tyr Glu Cys
65                  70                  75                  80

Ala Trp Val Ser Ser Thr Gly Ile Val Lys Lys Gly Leu Glu Trp Phe
                85                  90                  95

Glu Lys Asn Ala Gly Thr Ile Lys Ser Trp Asp Glu Ser Tyr Thr Glu
            100                 105                 110

Leu Lys Val Asp Val Pro Lys Ile Glu Gln Leu Thr Gly Tyr Gln Gln
        115                 120                 125

Ala Ala Leu Lys Trp Arg Lys Asp Ile Gly Phe Arg Val Asn Ala Asn
    130                 135                 140

Thr Ala Ala Leu Ser Asn Lys Val Leu Ala Glu Tyr Lys Val Pro Gly
145                 150                 155                 160

Glu Ile Val Met Ser Val Lys Glu Met Leu Ser Asp Met Ile Arg Arg
                165                 170                 175

Arg Asn Leu Ile Leu Asn Arg Gly Gly Asp Glu Asn Pro Arg Gly Pro
            180                 185                 190

Val Ser His Glu His Val Asp Trp Cys Arg Glu Phe Val Lys Gly Lys
        195                 200                 205

Tyr Ile Met Ala Phe Asn Pro Pro Trp Gly Asp Ile Asn Lys Ser Gly
    210                 215                 220

Arg Ser Gly Ile Ala Leu Val Ala Thr Gly Leu Ala Lys Leu Ala Glu
225                 230                 235                 240

Thr Glu Gly Lys Gly Ile Phe Asp Glu Ala Lys Lys Thr Val Glu Ala
                245                 250                 255

Leu Asn Gly Tyr Leu Asp Lys His Lys Asp Glu Val Asp Arg Ala Ser
            260                 265                 270

Ala Asp Ser Met Ile Thr Asn Leu Leu Lys His Ile Ala Lys Ala Gln
        275                 280                 285

```
Glu Leu Tyr Lys Asn Ser Ser Ala Leu Arg Ala Gln Ser Ala Gln Ile
    290                 295                 300

Asp Thr Ala Phe Ser Ser Tyr Tyr Trp Leu Tyr Lys Ala Gly Val Thr
305                 310                 315                 320

Pro Glu Thr Phe Pro Thr Val Ser Gln Phe Leu Phe Glu Leu Gly Lys
                325                 330                 335

Gln Pro Arg Gly Thr Lys Lys Met Lys Lys Ala Leu Leu Ser Thr Pro
            340                 345                 350

Met Lys Trp Gly Lys Lys Leu Tyr Glu Leu Phe Ala Asp Asp Ser Phe
        355                 360                 365

Gln Gln Asn Arg Ile Tyr Met His Pro Ala Val Leu Thr Ala Gly Arg
    370                 375                 380

Ile Ser Glu Met Gly Val Cys Phe Gly Thr Ile Pro Val Ala Asn Pro
385                 390                 395                 400

Asp Asp Ala Ala Gln Gly Ser Gly His Thr Lys Ser Ile Leu Asn Leu
                405                 410                 415

Arg Thr Asn Thr Glu Thr Asn Asn Pro Cys Ala Lys Thr Ile Val Lys
            420                 425                 430

Leu Phe Glu Val Gln Lys Thr Gly Phe Asn Ile Gln Asp Met Asp Ile
        435                 440                 445

Val Ala Ser Glu His Leu Leu His Gln Ser Leu Val Gly Lys Gln Ser
    450                 455                 460

Pro Phe Gln Asn Ala Tyr Asn Val Lys Gly Asn Ala Thr Ser Ala Asn
465                 470                 475                 480

Ile Ile

<210> SEQ ID NO 24
<211> LENGTH: 2936
<212> TYPE: DNA
<213> ORGANISM: Artificial Sequence
<220> FEATURE:
<223> OTHER INFORMATION: . pUC57-S-NSmGn (non-optimized NSmGn sequence)
<220> FEATURE:
<221> NAME/KEY: CDS
<222> LOCATION: (39)..(773)

<400> SEQUENCE: 24
acacaaagct ccctagagat acaaacacta ttacaata atg gac aac tat caa gag      56
                                          Met Asp Asn Tyr Gln Glu
                                          1               5 ctt gcg atc cag ttt gct gct caa gca gtg gac cgc aat gag att gaa       104
Leu Ala Ile Gln Phe Ala Ala Gln Ala Val Asp Arg Asn Glu Ile Glu
            10                  15                  20 cag tgg gtc cga gag ttt gct tat caa gga ttt gat gcc cgt agg gtt       152
Gln Trp Val Arg Glu Phe Ala Tyr Gln Gly Phe Asp Ala Arg Arg Val
        25                  30                  35 atc gaa ctc tta aag cag tat ggt ggg gct gac tgg gag aag gat gcc       200
Ile Glu Leu Leu Lys Gln Tyr Gly Gly Ala Asp Trp Glu Lys Asp Ala
    40                  45                  50 aag aaa atg att gtt ctg gct ctg act cgt ggc aac aag ccc cgg agg       248
Lys Lys Met Ile Val Leu Ala Leu Thr Arg Gly Asn Lys Pro Arg Arg
55                  60                  65                  70 atg atg atg aaa atg tcg aaa gaa ggc aaa gca act gtg gag gct ctc       296
Met Met Met Lys Met Ser Lys Glu Gly Lys Ala Thr Val Glu Ala Leu
                75                  80                  85 atc aac aag tat aag cta aag gag ggg aat cct tcc cgg gat gag ttg       344
Ile Asn Lys Tyr Lys Leu Lys Glu Gly Asn Pro Ser Arg Asp Glu Leu
            90                  95                  100
```

| | | |
|---|---|---|
| act cta tca cga gtt gct gct gcc ctg gct ggc tgg act tgc cag gct<br>Thr Leu Ser Arg Val Ala Ala Ala Leu Ala Gly Trp Thr Cys Gln Ala<br>105                    110                   115 | | 392 |
| ttg gtc gtc ttg agt gag tgg ctt cct gtc act ggg acc act atg gat<br>Leu Val Val Leu Ser Glu Trp Leu Pro Val Thr Gly Thr Thr Met Asp<br>120                    125                   130 | | 440 |
| ggc cta tcc cct gca tac cca agg cat atg atg cac ccc agc ttt gct<br>Gly Leu Ser Pro Ala Tyr Pro Arg His Met Met His Pro Ser Phe Ala<br>135                    140                   145                 150 | | 488 |
| ggc atg gtg gac cct tct cta cca gaa gac tat cta agg gca ata ttg<br>Gly Met Val Asp Pro Ser Leu Pro Glu Asp Tyr Leu Arg Ala Ile Leu<br>                 155                   160                   165 | | 536 |
| gat gct cac tct ctg tat ctg ctg cag ttc tcc cgg gtc atc aac cca<br>Asp Ala His Ser Leu Tyr Leu Leu Gln Phe Ser Arg Val Ile Asn Pro<br>170                    175                   180 | | 584 |
| aac ctc cga ggt aga aca aag gag gag gtt gcc gca acg ttc acg cag<br>Asn Leu Arg Gly Arg Thr Lys Glu Glu Val Ala Ala Thr Phe Thr Gln<br>                 185                   190                   195 | | 632 |
| cca atg aat gca gca gtg aat agc aac ttt ata agc cat gag aag agg<br>Pro Met Asn Ala Ala Val Asn Ser Asn Phe Ile Ser His Glu Lys Arg<br>200                    205                   210 | | 680 |
| aga gaa ttc ttg aaa gct ttt ggg ctt gtg gat tcc aat ggg aag ccg<br>Arg Glu Phe Leu Lys Ala Phe Gly Leu Val Asp Ser Asn Gly Lys Pro<br>215                    220                   225                   230 | | 728 |
| tca gca gct gtc atg gca gct gct cag gcg tac aag aca gca gcc<br>Ser Ala Ala Val Met Ala Ala Ala Gln Ala Tyr Lys Thr Ala Ala<br>                     235                   240                   245 | | 773 |
| taagtggctg cccaggggtt tggggaaaag ggggtggttg gggttacggt cgggattggg | | 833 |
| ggtgggggt ggggcagcct taatcttcta gactactaac gtggaattgg agcatgacga | | 893 |
| ggaataggg cagggttccc tagagccagc tggcctcctt ccatccatcc tatttccctg | | 953 |
| ttcacctgat tgatattgtc tgctactctg caaccatct tcttatacac ccatctgatg | | 1013 |
| aaaacagtaa tccacattag tggatccaga actttccttg gggcaatctt taggcacttg | | 1073 |
| agaactttat aaagaatggc caaacaaatt attgcgacag agctaaatac gaacacaaca | | 1133 |
| acaaaggcac tgagagcagt gtgacactgg taatttatca ggccatgagc acacactatg | | 1193 |
| cagccatgca ctaggcatgg atcctgggga gggcagtgag ctactatttt ggagctaact | | 1253 |
| gactgatcat catgtgccat gtgaacccct atgtccccc cagaggactg ggatatccct | | 1313 |
| ggatacttga gtgtaatctc ggtagaaggg ctctgcgatc ctgtaacgca aactccgcta | | 1373 |
| gcacaagcaa ctgcagatga tatcttgaaa cctgttgatc ggacaaccaa tccgtgaggc | | 1433 |
| tcacatttgg ttatacaagt tgtgcaaggc tcaactctct ggatgggctt agcagagagt | | 1493 |
| tctctcttca caaccaccct ctcatacccg acacacaaag gcttcttcca gaccccggat | | 1553 |
| acttgtatct gtacaactcc tgacccatta gcatgtgaac aataagcatt ggcgtattga | | 1613 |
| gcagtgcact cataagcaga gcaaaaagct gcgtccccag tgcacttctt gctaccatgt | | 1673 |
| cctccaatct tggggcactg agagatatca aagcttttga gctccctctt ggtctgacca | | 1733 |
| gagtccattg ttcctttata ctgtccctta tgctcgaagc agacaaatga gtctggcaac | | 1793 |
| agattttcct cagtcttgag gtcaagctta tcaagataaa ccttctttga gttcttaaat | | 1853 |
| actgcaaagg gcacaacctc atgtgcagtg ctgagttggc catcacactt tttgagtgct | | 1913 |
| tgaaccccca cttcgcagac ccctttcatt tttgttttta attttgatcc atcatcctca | | 1973 |
| cttgactgac aaaataagtc ctgaagagga taagacccct tcttcaagct agcacctgtc | | 2033 |
| atctgcctgc aaaaattgca gtcctcagtg agctcatatt taggagggca cttgactgaa | | 2093 |

-continued

```
gccattttcc cgtcattgtt gaggtaatga gctgactggt agtcatttgg acagtgtgtc    2153
ttcatcacga gtttctcctt catgcaggga ttcccatgag cactctgaag gtcacagcta    2213
ggtggatcag cctttgcaat gatggtgtcg tgaactgctt ctagtagggt tctgtgatgg    2273
gcatacgact ggaagagggg gaattttccc ttttcgagca agacatcaaa actgctacaa    2333
gccccagcat atgtcacagg tttgcatgtg gcgtcctcct gagtcatccc gtcaatgtag    2393
ttgtgcccct tccctggtct gtttctgaga tgagggtctt cagcaaaaac aacaggtgcc    2453
aaagcaaaaa ctgctaaggc tggaaggact gtcattgcaa tccctgccat ggtttctctt    2513
cctatttgct tagcgtctct tcgtctctca caccgaacta tccccacccg cttttttgtga   2573 ggaggaccct ttacgagaga atcttatcc tcaggatcct taccatggca ggtgatgttg     2633
ttcaagccat cagcagcaat gatggctttt aatgccctat acaattcctg gcttgaggtt    2693
ttgacctccc ttatgcctga tatggaacag gagagctcct ctggcatctc ctcctctctg    2753
agtgaatccc aagctccttc aatcatctct gggttggtgt agtcaccaaa gcaggtctct    2813
tctcttgtgg aacttagaga cactctaata accgcctcac acaccagaac cgtgatcaga    2873
attgttagta aacatacat ggtactagtg atatacttga taagcactag ggggtctttg     2933
tgt                                                                  2936
```

<210> SEQ ID NO 25
<211> LENGTH: 245
<212> TYPE: PRT
<213> ORGANISM: Artificial Sequence
<220> FEATURE:
<223> OTHER INFORMATION: Synthetic Construct

<400> SEQUENCE: 25

```
Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
            20                  25                  30

Phe Asp Ala Arg Arg Val Ile Glu Leu Leu Lys Gln Tyr Gly Gly Ala
        35                  40                  45

Asp Trp Glu Lys Asp Ala Lys Lys Met Ile Val Leu Ala Leu Thr Arg
    50                  55                  60

Gly Asn Lys Pro Arg Arg Met Met Met Lys Met Ser Lys Glu Gly Lys
65                  70                  75                  80

Ala Thr Val Glu Ala Leu Ile Asn Lys Tyr Lys Leu Lys Glu Gly Asn
                85                  90                  95

Pro Ser Arg Asp Glu Leu Thr Leu Ser Arg Val Ala Ala Leu Ala
            100                 105                 110

Gly Trp Thr Cys Gln Ala Leu Val Val Leu Ser Glu Trp Leu Pro Val
        115                 120                 125

Thr Gly Thr Thr Met Asp Gly Leu Ser Pro Ala Tyr Pro Arg His Met
    130                 135                 140

Met His Pro Ser Phe Ala Gly Met Val Asp Pro Ser Leu Pro Glu Asp
145                 150                 155                 160

Tyr Leu Arg Ala Ile Leu Asp Ala His Ser Leu Tyr Leu Leu Gln Phe
                165                 170                 175

Ser Arg Val Ile Asn Pro Asn Leu Arg Gly Arg Thr Lys Glu Glu Val
            180                 185                 190

Ala Ala Thr Phe Thr Gln Pro Met Asn Ala Ala Val Asn Ser Asn Phe
        195                 200                 205
```

Ile Ser His Glu Lys Arg Arg Glu Phe Leu Lys Ala Phe Gly Leu Val
        210                 215                 220

Asp Ser Asn Gly Lys Pro Ser Ala Ala Val Met Ala Ala Ala Gln Ala
225                 230                 235                 240

Tyr Lys Thr Ala Ala
            245

<210> SEQ ID NO 26
<211> LENGTH: 674
<212> TYPE: PRT
<213> ORGANISM: Artificial Sequence
<220> FEATURE:
<223> OTHER INFORMATION: protein encoded by reverse strand of
      pUC57-S-NSmGn

<400> SEQUENCE: 26

Met Tyr Val Leu Leu Thr Ile Leu Ile Thr Val Leu Val Cys Glu Ala
1               5                   10                  15

Val Ile Arg Val Ser Leu Ser Ser Thr Arg Glu Glu Cys Phe Gly
            20                  25                  30

Asp Tyr Thr Asn Pro Glu Met Ile Glu Gly Ala Trp Asp Ser Leu Arg
            35                  40                  45

Glu Glu Glu Met Pro Glu Leu Ser Cys Ser Ile Ser Gly Ile Arg
50                  55                  60

Glu Val Lys Thr Ser Ser Gln Glu Leu Tyr Arg Ala Leu Lys Ala Ile
65                  70                  75                  80

Ile Ala Ala Asp Gly Leu Asn Asn Ile Thr Cys His Gly Lys Asp Pro
                85                  90                  95

Glu Asp Lys Ile Ser Leu Val Lys Gly Pro Pro His Lys Lys Arg Val
                100                 105                 110

Gly Ile Val Arg Cys Glu Arg Arg Asp Ala Lys Gln Ile Gly Arg
            115                 120                 125

Glu Thr Met Ala Gly Ile Ala Met Thr Val Leu Pro Ala Leu Ala Val
            130                 135                 140

Phe Ala Leu Ala Pro Val Val Phe Ala Glu Asp Pro His Leu Arg Asn
145                 150                 155                 160

Arg Pro Gly Lys Gly His Asn Tyr Ile Asp Gly Met Thr Gln Glu Asp
                165                 170                 175

Ala Thr Cys Lys Pro Val Thr Tyr Ala Gly Ala Cys Ser Ser Phe Asp
                180                 185                 190

Val Leu Leu Glu Lys Gly Lys Phe Pro Leu Phe Gln Ser Tyr Ala His
            195                 200                 205

His Arg Thr Leu Leu Glu Ala Val His Asp Thr Ile Ile Ala Lys Ala
            210                 215                 220

Asp Pro Pro Ser Cys Asp Leu Gln Ser Ala His Gly Asn Pro Cys Met
225                 230                 235                 240

Lys Glu Lys Leu Val Met Lys Thr His Cys Pro Asn Asp Tyr Gln Ser
                245                 250                 255

Ala His Tyr Leu Asn Asn Asp Gly Lys Met Ala Ser Val Lys Cys Pro
                260                 265                 270

Pro Lys Tyr Glu Leu Thr Glu Asp Cys Asn Phe Cys Arg Gln Met Thr
            275                 280                 285

Gly Ala Ser Leu Lys Lys Gly Ser Tyr Pro Leu Gln Asp Leu Phe Cys
            290                 295                 300

Gln Ser Ser Glu Asp Asp Gly Ser Lys Leu Lys Thr Lys Met Lys Gly

```
            305                 310                 315                 320
        Val Cys Glu Val Gly Val Gln Ala Leu Lys Lys Cys Asp Gly Gln Leu
                        325                 330                 335

Ser Thr Ala His Glu Val Val Pro Phe Ala Val Phe Lys Asn Ser Lys
                        340                 345                 350

Lys Val Tyr Leu Asp Lys Leu Asp Leu Lys Thr Glu Glu Asn Leu Leu
                        355                 360                 365

Pro Asp Ser Phe Val Cys Phe Glu His Lys Gly Gln Tyr Lys Gly Thr
                        370                 375                 380

Met Asp Ser Gly Gln Thr Lys Arg Glu Leu Lys Ser Phe Asp Ile Ser
        385                 390                 395                 400

Gln Cys Pro Lys Ile Gly Gly His Gly Ser Lys Lys Cys Thr Gly Asp
                        405                 410                 415

Ala Ala Phe Cys Ser Ala Tyr Glu Cys Thr Ala Gln Tyr Ala Asn Ala
                        420                 425                 430

Tyr Cys Ser His Ala Asn Gly Ser Gly Val Val Gln Ile Gln Val Ser
                        435                 440                 445

Gly Val Trp Lys Lys Pro Leu Cys Val Gly Tyr Glu Arg Val Val Val
                        450                 455                 460

Lys Arg Glu Leu Ser Ala Lys Pro Ile Gln Arg Val Glu Pro Cys Thr
        465                 470                 475                 480

Thr Cys Ile Thr Lys Cys Glu Pro His Gly Leu Val Val Arg Ser Thr
                        485                 490                 495

Gly Phe Lys Ile Ser Ser Ala Val Ala Cys Ala Ser Gly Val Cys Val
                        500                 505                 510

Thr Gly Ser Gln Ser Pro Ser Thr Glu Ile Thr Leu Lys Tyr Pro Gly
                        515                 520                 525

Ile Ser Gln Ser Ser Gly Gly Asp Ile Gly Val His Met Ala His Asp
                        530                 535                 540

Asp Gln Ser Val Ser Ser Lys Ile Val Ala His Cys Pro Pro Gln Asp
        545                 550                 555                 560

Pro Cys Leu Val His Gly Cys Ile Val Cys Ala His Gly Leu Ile Asn
                        565                 570                 575

Tyr Gln Cys His Thr Ala Leu Ser Ala Phe Val Val Phe Val Phe
                        580                 585                 590

Ser Ser Val Ala Ile Ile Cys Leu Ala Ile Leu Tyr Lys Val Leu Lys
                        595                 600                 605

Cys Leu Lys Ile Ala Pro Arg Lys Val Leu Asp Pro Leu Met Trp Ile
                        610                 615                 620

Thr Val Phe Ile Arg Trp Val Tyr Lys Lys Met Val Ala Arg Val Ala
        625                 630                 635                 640

Asp Asn Ile Asn Gln Val Asn Arg Glu Ile Gly Trp Met Glu Gly Gly
                        645                 650                 655

Gln Leu Ala Leu Gly Asn Pro Ala Pro Ile Pro Arg His Ala Pro Ile
                        660                 665                 670

Pro Arg

<210> SEQ ID NO 27
<211> LENGTH: 2486
<212> TYPE: DNA
<213> ORGANISM: Artificial Sequence
<220> FEATURE:
<223> OTHER INFORMATION: pUC57-S-Gc (non-optimized Gc sequence)
<220> FEATURE:
<221> NAME/KEY: CDS
```

<222> LOCATION: (39)..(773)

<400> SEQUENCE: 27

```
acacaaagct ccctagagat acaaacacta ttacaata atg gac aac tat caa gag        56
                                            Met Asp Asn Tyr Gln Glu
                                            1               5 ctt gcg atc cag ttt gct gct caa gca gtg gac cgc aat gag att gaa         104
Leu Ala Ile Gln Phe Ala Ala Gln Ala Val Asp Arg Asn Glu Ile Glu
             10                  15                  20 cag tgg gtc cga gag ttt gct tat caa gga ttt gat gcc cgt agg gtt         152
Gln Trp Val Arg Glu Phe Ala Tyr Gln Gly Phe Asp Ala Arg Arg Val
 25                  30                  35 atc gaa ctc tta aag cag tat ggt ggg gct gac tgg gag aag gat gcc         200
Ile Glu Leu Leu Lys Gln Tyr Gly Gly Ala Asp Trp Glu Lys Asp Ala
 40                  45                  50 aag aaa atg att gtt ctg gct ctg act cgt ggc aac aag ccc cgg agg         248
Lys Lys Met Ile Val Leu Ala Leu Thr Arg Gly Asn Lys Pro Arg Arg
 55                  60                  65                  70 atg atg atg aaa atg tcg aaa gaa ggc aaa gca act gtg gag gct ctc         296
Met Met Met Lys Met Ser Lys Glu Gly Lys Ala Thr Val Glu Ala Leu
                 75                  80                  85 atc aac aag tat aag cta aag gag ggg aat cct tcc cgg gat gag ttg         344
Ile Asn Lys Tyr Lys Leu Lys Glu Gly Asn Pro Ser Arg Asp Glu Leu
             90                  95                 100 act cta tca cga gtt gct gct gcc ctg gct ggc tgg act tgc cag gct         392
Thr Leu Ser Arg Val Ala Ala Ala Leu Ala Gly Trp Thr Cys Gln Ala
        105                 110                 115 ttg gtc gtc ttg agt gag tgg ctt cct gtc act ggg acc act atg gat         440
Leu Val Val Leu Ser Glu Trp Leu Pro Val Thr Gly Thr Thr Met Asp
120                 125                 130 ggc cta tcc cct gca tac cca agg cat atg atg cac ccc agc ttt gct         488
Gly Leu Ser Pro Ala Tyr Pro Arg His Met Met His Pro Ser Phe Ala
135                 140                 145                 150 ggc atg gtg gac cct tct cta cca gaa gac tat cta agg gca ata ttg         536
Gly Met Val Asp Pro Ser Leu Pro Glu Asp Tyr Leu Arg Ala Ile Leu
                155                 160                 165 gat gct cac tct ctg tat ctg ctg cag ttc tcc cgg gtc atc aac cca         584
Asp Ala His Ser Leu Tyr Leu Leu Gln Phe Ser Arg Val Ile Asn Pro
            170                 175                 180 aac ctc cga ggt aga aca aag gag gag gtt gcc gca acg ttc acg cag         632
Asn Leu Arg Gly Arg Thr Lys Glu Glu Val Ala Ala Thr Phe Thr Gln
        185                 190                 195 cca atg aat gca gca gtg aat agc aac ttt ata agc cat gag aag agg         680
Pro Met Asn Ala Ala Val Asn Ser Asn Phe Ile Ser His Glu Lys Arg
200                 205                 210 aga gaa ttc ttg aaa gct ttt ggg ctt gtg gat tcc aat ggg aag ccg         728
Arg Glu Phe Leu Lys Ala Phe Gly Leu Val Asp Ser Asn Gly Lys Pro
215                 220                 225                 230 tca gca gct gtc atg gca gct gct cag gcg tac aag aca gca gcc             773
Ser Ala Ala Val Met Ala Ala Ala Gln Ala Tyr Lys Thr Ala Ala
                235                 240                 245 taagtggctg cccagggggtt tggggaaaag ggggtggttg gggttacggt cgggattggg       833 ggtgggggt gggcagcct taatcttcta gcgatctatg aggctttctt ggtggcagca         893
agccacattt tagagaggcc tgttcttcca agatatataa gaaggaaaaa gagcccaatt       953
gataatgcta catacaggca aatgaggagt atagtcttaa gaggccctcc aaaccaactc      1013
atgagtccag aaaccagtc aaagaaattc caagatccag attttggatt cacaactgtt      1073 gattccccc ctgcttctcg cctatcatca aatggatcaa tagctatcag ggttcccttc      1133
```

```
accaacagag gccgctcatc tccatcacaa gagtacataa actcctcctc tacctcaggt      1193
acagtgaagt gtagtatctg acactgatct tttgttccat tctctgatgg aagaactata      1253
tgcagagatc catctttatt gtgggcagag agagttccag ttcctgtgga tgtgatagac      1313
aggcagactc tggcccctgc attgcaggaa tagcaacctg tcaaatttaa gaaggcggca      1373
tcacaagaca cggctgctcc cacaaagtcc acctcaaaat tgtcaaacat cagtgttaga      1433
tcagcctgta cagagccctt agagaaagct gaacacccc tatttccttt tgaagctgca       1493
aaggttttgt cattccttgt ctgtggcaga gagcccctct caaagacaac aaagggatca      1553
atcagatttg ttgtgcactc caactgatct atcatgggct tgtatgaaat aagatttggt      1613
gccctaaggc atgattcatg agcactcagg actgaagatt ctgaattgca cctgatctcc      1673
cccaagaacc cttgccgagg aatttctgag aatggctcat caacaattgc atacccttg       1733 cctgggctct caatgaagga aaagctgttt gagcctgaaa tgccctctgc gtccagtgag      1793
aggctaactg aacccagtt tgtgaaacgg ctagatgatg ctcccaggtc tattgttgaa       1853
acagagccat caaagtcagt aatctctaga gtgagtttat gcacccaatc gatacagttg      1913
aaaactctaa gggcctcttt tctgactgac tgcagatacg tgtgcacaaa taagcaagat      1973
gggttcacat tgaaacaccc catcccat cctccacact gctcaaaaca cttgttctcc        2033
cgcatggtcg tgctttcccc aacaaatgaa aattctgctg aggtttcatt gtctctccaa      2093
gacagacacc tattcacatg acattccccg acaagatggc atctccttga gctcagacat      2153
ttagggctaa aggacccagt ccaatagctc tggccctccc tgcacgatag ctcacttgag      2213
acagttttta tcttcaaaaa cttggtttgg tcttccttga ccccctttaa catcaaacaa      2273
gcctctgccc caactgaccc tgccctgatt aatgctgtgc cagacagcct acacttggtg      2333
ttgacacctt ctgtggagca gtggtgatt ctggagcttg cctgaatcag ttctgaacat       2393
gctgatgcat atgagacaat caatagtagc attaggtatg tgctatacat ggtactagtg      2453
atatacttga taagcactag ggggtctttg tgt                                  2486
```

<210> SEQ ID NO 28
<211> LENGTH: 245
<212> TYPE: PRT
<213> ORGANISM: Artificial Sequence
<220> FEATURE:
<223> OTHER INFORMATION: Synthetic Construct

<400> SEQUENCE: 28

```
Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
            20                  25                  30

Phe Asp Ala Arg Arg Val Ile Glu Leu Leu Lys Gln Tyr Gly Gly Ala
        35                  40                  45

Asp Trp Glu Lys Asp Ala Lys Lys Met Ile Val Leu Ala Leu Thr Arg
    50                  55                  60

Gly Asn Lys Pro Arg Arg Met Met Lys Met Ser Lys Glu Gly Lys
65                  70                  75                  80

Ala Thr Val Glu Ala Leu Ile Asn Lys Tyr Lys Leu Lys Glu Gly Asn
                85                  90                  95

Pro Ser Arg Asp Glu Leu Thr Leu Ser Arg Val Ala Ala Ala Leu Ala
            100                 105                 110

Gly Trp Thr Cys Gln Ala Leu Val Val Leu Ser Glu Trp Leu Pro Val
```

```
                    115                 120                 125
Thr Gly Thr Thr Met Asp Gly Leu Ser Pro Ala Tyr Pro Arg His Met
            130                 135                 140

Met His Pro Ser Phe Ala Gly Met Val Asp Pro Ser Leu Pro Glu Asp
145                 150                 155                 160

Tyr Leu Arg Ala Ile Leu Asp Ala His Ser Leu Tyr Leu Leu Gln Phe
                    165                 170                 175

Ser Arg Val Ile Asn Pro Asn Leu Arg Gly Arg Thr Lys Glu Glu Val
                180                 185                 190

Ala Ala Thr Phe Thr Gln Pro Met Asn Ala Ala Val Asn Ser Asn Phe
            195                 200                 205

Ile Ser His Glu Lys Arg Arg Glu Phe Leu Lys Ala Phe Gly Leu Val
        210                 215                 220

Asp Ser Asn Gly Lys Pro Ser Ala Ala Val Met Ala Ala Ala Gln Ala
225                 230                 235                 240

Tyr Lys Thr Ala Ala
                245

<210> SEQ ID NO 29
<211> LENGTH: 524
<212> TYPE: PRT
<213> ORGANISM: Artificial Sequence
<220> FEATURE:
<223> OTHER INFORMATION: protein encoded by reverse strand of pUC57-S-Gc

<400> SEQUENCE: 29

Met Tyr Ser Thr Tyr Leu Met Leu Leu Ile Val Ser Tyr Ala Ser
1               5                   10                  15

Ala Cys Ser Glu Leu Ile Gln Ala Ser Ser Arg Ile Thr Thr Cys Ser
                20                  25                  30

Thr Glu Gly Val Asn Thr Lys Cys Arg Leu Ser Gly Thr Ala Leu Ile
            35                  40                  45

Arg Ala Gly Ser Val Gly Ala Glu Ala Cys Leu Met Leu Lys Gly Val
        50                  55                  60

Lys Glu Asp Gln Thr Lys Phe Leu Lys Ile Lys Thr Val Ser Ser Glu
65                  70                  75                  80

Leu Ser Cys Arg Glu Gly Gln Ser Tyr Trp Thr Gly Ser Phe Ser Pro
                85                  90                  95

Lys Cys Leu Ser Ser Arg Arg Cys His Leu Val Gly Glu Cys His Val
                100                 105                 110

Asn Arg Cys Leu Ser Trp Arg Asp Asn Glu Thr Ser Ala Glu Phe Ser
            115                 120                 125

Phe Val Gly Glu Ser Thr Thr Met Arg Glu Asn Lys Cys Phe Glu Gln
        130                 135                 140

Cys Gly Gly Trp Gly Cys Gly Cys Phe Asn Val Asn Pro Ser Cys Leu
145                 150                 155                 160

Phe Val His Thr Tyr Leu Gln Ser Val Arg Lys Glu Ala Leu Arg Val
                165                 170                 175

Phe Asn Cys Ile Asp Trp Val His Lys Leu Thr Leu Glu Ile Thr Asp
                180                 185                 190

Phe Asp Gly Ser Val Ser Thr Ile Asp Leu Gly Ala Ser Ser Ser Arg
            195                 200                 205

Phe Thr Asn Trp Gly Ser Val Ser Leu Ser Leu Asp Ala Glu Gly Ile
        210                 215                 220

Ser Gly Ser Asn Ser Phe Ser Phe Ile Glu Ser Pro Gly Lys Gly Tyr
```

```
                    225                 230                 235                 240

Ala Ile Val Asp Glu Pro Phe Ser Glu Ile Pro Arg Gln Gly Phe Leu
                        245                 250                 255

Gly Glu Ile Arg Cys Asn Ser Glu Ser Ser Val Leu Ser Ala His Glu
                        260                 265                 270

Ser Cys Leu Arg Ala Pro Asn Leu Ile Ser Tyr Lys Pro Met Ile Asp
                        275                 280                 285

Gln Leu Glu Cys Thr Thr Asn Leu Ile Asp Pro Phe Val Val Phe Glu
                        290                 295                 300

Arg Gly Ser Leu Pro Gln Thr Arg Asn Asp Lys Thr Phe Ala Ala Ser
        305                 310                 315                 320

Lys Gly Asn Arg Gly Val Gln Ala Phe Ser Lys Gly Ser Val Gln Ala
                        325                 330                 335

Asp Leu Thr Leu Met Phe Asp Asn Phe Glu Val Asp Phe Val Gly Ala
                        340                 345                 350

Ala Val Ser Cys Asp Ala Ala Phe Leu Asn Leu Thr Gly Cys Tyr Ser
                        355                 360                 365

Cys Asn Ala Gly Ala Arg Val Cys Leu Ser Ile Thr Ser Thr Gly Thr
                        370                 375                 380

Gly Thr Leu Ser Ala His Asn Lys Asp Gly Ser Leu His Ile Val Leu
        385                 390                 395                 400

Pro Ser Glu Asn Gly Thr Lys Asp Gln Cys Gln Ile Leu His Phe Thr
                        405                 410                 415

Val Pro Glu Val Glu Glu Phe Met Tyr Ser Cys Asp Gly Asp Glu
                        420                 425                 430

Arg Pro Leu Leu Val Lys Gly Thr Leu Ile Ala Ile Asp Pro Phe Asp
                        435                 440                 445

Asp Arg Arg Glu Ala Gly Gly Glu Ser Thr Val Val Asn Pro Lys Ser
                        450                 455                 460

Gly Ser Trp Asn Phe Phe Asp Trp Phe Ser Gly Leu Met Ser Trp Phe
        465                 470                 475                 480

Gly Gly Pro Leu Lys Thr Ile Leu Leu Ile Cys Leu Tyr Val Ala Leu
                        485                 490                 495

Ser Ile Gly Leu Phe Phe Leu Leu Ile Tyr Leu Gly Arg Thr Gly Leu
                        500                 505                 510

Ser Lys Met Trp Leu Ala Ala Thr Lys Lys Ala Ser
                        515                 520

<210> SEQ ID NO 30
<211> LENGTH: 47
<212> TYPE: DNA
<213> ORGANISM: Artificial Sequence
<220> FEATURE:
<223> OTHER INFORMATION: PRIMER

<400> SEQUENCE: 30
taatacgact cactataggg tcagtgtttc ctacttgaag gaggctt                    47

<210> SEQ ID NO 31
<211> LENGTH: 24
<212> TYPE: DNA
<213> ORGANISM: Artificial Sequence
<220> FEATURE:
<223> OTHER INFORMATION: PRIMER

<400> SEQUENCE: 31
aagtccacac aggcccctta catt                                             24
```

<210> SEQ ID NO 32
<211> LENGTH: 43
<212> TYPE: DNA
<213> ORGANISM: Artificial Sequence
<220> FEATURE:
<223> OTHER INFORMATION: PRIMER

<400> SEQUENCE: 32
taatacgact cactataggg ggtctgcgaa gtggggttc aag        43

<210> SEQ ID NO 33
<211> LENGTH: 22
<212> TYPE: DNA
<213> ORGANISM: Artificial Sequence
<220> FEATURE:
<223> OTHER INFORMATION: PRIMER

<400> SEQUENCE: 33
gacaaccaat ccgtgaggct ca        22

<210> SEQ ID NO 34
<211> LENGTH: 45
<212> TYPE: DNA
<213> ORGANISM: Artificial Sequence
<220> FEATURE:
<223> OTHER INFORMATION: PRIMER

<400> SEQUENCE: 34
taatacgact cactataggg cggacaacca atccgtgagg ctcac        45

<210> SEQ ID NO 35
<211> LENGTH: 25
<212> TYPE: DNA
<213> ORGANISM: Artificial Sequence
<220> FEATURE:
<223> OTHER INFORMATION: PRIMER

<400> SEQUENCE: 35
cgaagtgggg gttcaagcac tcaaa        25

<210> SEQ ID NO 36
<211> LENGTH: 45
<212> TYPE: DNA
<213> ORGANISM: Artificial Sequence
<220> FEATURE:
<223> OTHER INFORMATION: PRIMER

<400> SEQUENCE: 36
taatacgact cactataggg gtctcaagtg agctatcgtg caggg        45

<210> SEQ ID NO 37
<211> LENGTH: 23
<212> TYPE: DNA
<213> ORGANISM: Artificial Sequence
<220> FEATURE:
<223> OTHER INFORMATION: PRIMER

<400> SEQUENCE: 37
attgcatacc ctttgcctgg gct        23

<210> SEQ ID NO 38
<211> LENGTH: 44
<212> TYPE: DNA
<213> ORGANISM: Artificial Sequence
<220> FEATURE:

<223> OTHER INFORMATION: PRIMER

<400> SEQUENCE: 38
taatacgact cactataggg agacacggct gctcccacaa agtc                    44

<210> SEQ ID NO 39
<211> LENGTH: 26
<212> TYPE: DNA
<213> ORGANISM: Artificial Sequence
<220> FEATURE:
<223> OTHER INFORMATION: PRIMER

<400> SEQUENCE: 39
cagtcagtca gaaagaggc ccttag                                         26

<210> SEQ ID NO 40
<211> LENGTH: 46
<212> TYPE: DNA
<213> ORGANISM: Artificial Sequence
<220> FEATURE:
<223> OTHER INFORMATION: PRIMER

<400> SEQUENCE: 40
taatacgact cactataggg tcaagcagtg gaccgcaatg agattg                  46

<210> SEQ ID NO 41
<211> LENGTH: 25
<212> TYPE: DNA
<213> ORGANISM: Artificial Sequence
<220> FEATURE:
<223> OTHER INFORMATION: PRIMER

<400> SEQUENCE: 41
attcactgct gcattcattg gctgc                                         25

<210> SEQ ID NO 42
<211> LENGTH: 49
<212> TYPE: DNA
<213> ORGANISM: Artificial Sequence
<220> FEATURE:
<223> OTHER INFORMATION: PRIMER

<400> SEQUENCE: 42
taatacgact cactataggg attctatctc aacatctggg attggagga              49

<210> SEQ ID NO 43
<211> LENGTH: 25
<212> TYPE: DNA
<213> ORGANISM: Artificial Sequence
<220> FEATURE:
<223> OTHER INFORMATION: PRIMER

<400> SEQUENCE: 43
cacctccacc agcaaagcct tttca                                         25

<210> SEQ ID NO 44
<211> LENGTH: 16
<212> TYPE: PRT
<213> ORGANISM: Artificial Sequence
<220> FEATURE:

```
<223> OTHER INFORMATION: protein encoding M-segment
<220> FEATURE:
<221> NAME/KEY: MISC_FEATURE
<222> LOCATION: (8)..(9)
<223> OTHER INFORMATION: Splicing site

<400> SEQUENCE: 44

Pro Arg His Ala Pro Ile Pro Arg Tyr Ser Thr Tyr Leu Met Leu Leu
1               5                   10                  15
```

BUNYAVIRUSES WITH SEGMENTED GLYCOPROTEIN PRECURSOR GENES AND METHODS FOR GENERATING THESE VIRUSES

RELATED APPLICATIONS

This application is the U.S. National Stage of International Application No. PCT/NL2014/050321, filed May 21, 2014, published in English, and claims the benefit of European Application Number 13168608.1, filed on May 21, 2013 and European Application Number 14150826.7, filed on Jan. 10, 2014, the entire teachings of the above applications are incorporated herein by reference.

SEQUENCE LISTING

The instant application contains a Sequence Listing which has been submitted electronically in ASCII format and is hereby incorporated by reference in its entirety. Said ASCII copy, created on Jan. 11, 2017, is named P101141US00 seqlist_ST25.txt and is 142,777 bytes in size.

FIELD

The invention relates to the field of viruses, more specifically, to the field of molecular virology of bunyaviruses. The invention relates to methods for the generation of an avirulent bunyavirus, and to a virus that is produced by these methods. The resulting virus can be used as a vaccine against an infectious disease mediated by bunyaviruses.

INTRODUCTION

Bunyaviruses are negative-strand RNA viruses with three-segmented genomes (Elliott, R. M. 1996. The Bunyaviridae. Plenum Press, New York, N.Y.). The Bunyaviridae family comprises five genera: Phlebovirus, Orthobunyavirus, Nairovirus, Hantavirus and Tospovirus. With the exception of the plant-infecting Tospovirus genus, bunyaviruses are pathogens of animals and humans. The small (S) bunyavirus genome segment encodes a nucleocapsid (N) protein and, with the possible exception of the Nairovirus genus, a nonstructural protein named NSs. The NSs protein of animal-infecting bunyaviruses functions as an antagonist of host innate immune responses and is considered the major virulence factor. The medium-size (M) genome segment encodes the viral structural glycoproteins Gn and Gc and, depending on the genus, one or more nonstructural proteins referred to as NSm. The M segment of Rift Valley fever virus (RVFV, genus Phlebovirus) additionally encodes a 78-kDa protein believed to be a minor structural protein. The large (L) genome segment encodes the viral RNA-dependent RNA polymerase (RdRp). Bunyaviruses that cause serious disease in animals and/or humans are classified as biosafety level 3 (BSL-3) or 4 pathogens, complicating the development of vaccines.

RVFV is an example of a Phlebovirus that is classified as a BSL-3 pathogen. RVFV is endemic to the African continent, Madagascar, the Comoros Islands, Mayotte and the Arabian Peninsula, where it is transmitted among livestock by mosquito vectors. RVFV epizootics are characterized by near simultaneous abortions, particularly among sheep, and high mortality among young animals below the age of two weeks. Humans can be infected via mosquito bite, but more commonly by inhalation of aerosols released during slaughtering of viremic animals. Infection of humans generally results in transient febrile illness. However, a small percentage of individuals develop complications such as retinal lesions, hepatic disease with hemorrhagic fever or delayed-onset encephalitis.

No vaccine exists for the prevention of RVF in humans. Two classical vaccines are used for the prevention of RVF in domesticated ruminants. Both vaccines are produced by Onderstepoort Biologicals Products (OBP), South Africa. The first is based on inactivated-whole virus. Although this vaccine can safely be applied in animals during all physiological stages, optimal efficacy depends on a booster vaccination and yearly re-vaccinations. The alternative "Smithburn" vaccine is a live virus that was attenuated by passage of the virus in suckling mouse brain (Smithburn 1949. Br J Exp Pathol 30:1-16). A single injection of this vaccine can provide solid protection, but due to residual virulence, this vaccine is not safe for young or gestating animals. More recently, a RVFV with a large deletion in the NSs gene, named the Clone 13 virus, was marketed as a livestock vaccine in South Africa by OBP. Relevant publications regarding the Clone 13 vaccine virus include Muller et al., 1995. Am J Trop Med Hyg 53:405-411; Vialat et al., 2000. J Virol. 74:1538-1543; Bouloy et al., 2001. J Virol 75:1371-1377; Dungu et al., 2010. Vaccine 28:4581-4587; Von Teichman et al., 2011 Vaccine 29:5771-5777. Although the aforementioned studies suggest that the Clone 13 virus can safely be applied in animals during all physiological stages, the virus was described to cause low-level viremia in hamsters (Muller et al., 1995. Am J Trop Med Hyg 53:405-411) and was shown to be capable of causing lethal delayed-onset encephalitis in mice (Vialat et al., 2000. J Virol. 74:1538-1543). Furthermore, the Clone 13 vaccine virus was shown to replicate extremely well in insect cell cultures and in mosquito vectors (Moutailler et al., 2010. Vector Borne Zoonotic Dis 10:681-688). Feeding of a mosquito on a Clone 13-vaccinated animal could result in amplification of the Clone 13 virus in the mosquito vector and, potentially, reassortment of genome segments with field viruses that are already present in the mosquito vector.

The work that resulted in the present invention was aimed to develop a RVFV vaccine for application in livestock and humans that optimally combines the efficacy of live vaccines with the safety of inactivated vaccines by being avirulent and non-transmissible by arthropod vectors.

The present invention provides a bunyavirus, in which separated (NSm)Gn and Gc coding regions are functionally present on two separate genome segments. Said two separate genome segments, preferably minigenome segments, are either L-L segments, L-M segments, L-S segments, M-S segments, M-M segments or S-S segments. It was found that the separation of Gn and Gc coding regions on two different genome segments, for example two M genome segments, results in a virus that has reduced replication capabilities in mammalian cell culture and is unable to replicate in insect cell culture. A preferred bunyavirus of the invention comprises a total of at least 3 genome segments, such as 3 genome segments or 4 genome segments. A bunyavirus comprising 3 genome segments preferably comprises S-S-L or S-L-L genome segments. A most preferred bunyavirus of the invention comprises a total of 4 genome segments, whereby each of the four genome segments comprises an essential gene selected from RdRp, NSm, Gn, and Gc. A preferred bunyavirus of the invention additionally comprises a functional deletion of the NSs gene.

A preferred bunyavirus of the invention comprising 3 genome segments (LMS) in which either (NSm)Gn or Gc is functionally present only on the S-segment. A most preferred bunyavirus of the invention comprising 4 genome segments comprises separate M-segments (LMMS), in which (NSm)Gn and Gc are functionally present on the separate M-segments. Said most preferred bunyavirus preferably also comprises a functional deletion of the NSs gene. It is further preferred that the coding sequence of the (NSm)Gn and/or Gc is codon optimized for efficient expression in mammalian cells, for example to remove rare codons. Methods for codon optimization are known in the art and are publicly available, for example from www.entelechon.com and from www.genscript.com.

A bunyavirus according to the invention comprises, as sole genomic segments, a bunyavirus L genome segment; and a bunyavirus M genome segment from which the (NSm)Gn and/or Gc coding region has been functionally inactivated, whereby the (NSm)Gn and/or Gc coding region that is deleted from the M genome segment is functionally present on a second L genome segment, a second M genome segment, or a S genome segment; or a second and a third L genome segment, a second L genome segment and a S genome segment, or a S genome segment and a second S genome segment, whereby separated (NSm)Gn and Gc coding regions are functionally present either on said second and a third L genome segment, on said second L genome segment and said S genome segment, or on said S genome segment and said second S genome segment. Said bunyavirus optionally further comprises a S genome segment, a S genome segment comprising at least the N gene and the 3' and 5' untranslated regions (UTRs); or a S-minigenome segment. A marker gene, for example encoding green fluorescent protein (GFP) may be present on one of the genome segments, for example on said S (mini)genome segment. It will be clear to a skilled person that variants of the above indicated bunyavirus, such as a bunyavirus without a (substantially complete) L genome segment and in which the coding region of the RdRp gene, which normally resides on the L genome segment, is functionally present on a (second) M or (second) S genome segment, and in which separated Gn and Gc coding regions are functionally present on two different genome segments, are also covered by this invention.

The work that resulted in the present invention started with the hypothesis that bunyaviruses are either not capable of efficiently packaging more than three genome segments and/or not capable of efficiently packaging two of the same type of genome segments (S, M or L) in a single particle in cells, for example mammalian and/or insect cells. To test this hypothesis, a virus was produced by combining four genome segments, namely the S genome segment, the L genome segment and two M-type minigenome segments, one encoding the NSmGn sequence and one encoding the Gc sequence. In a mammalian cell system, this combination resulted in infectious particles able to spread autonomously. Growth of a four-segmented bunyavirus can be explained by packaging of all four genome segments into a single virus particle or, alternatively, by co-infection of a single cell with two or more complementing particles. The resulting virus replicates considerably slower in mammalian cell culture compared to a virus that contains the authentic M segment (FIG. 6), which can be attributed to one or more of the following features: 1. Impaired glycoprotein and/or particle assembly; 2. Impaired genome packaging; 3. Impaired genome replication due to the presence of a fourth genome segment in infected cells. These properties will attenuate the virus in vivo. Remarkably, low moi infection of insect cells did not result in virus growth (FIG. 6). This suggests that the aforementioned mechanism(s) is (are) particularly inefficient in insect cells.

The term (NSm)Gn sequence indicates that the coding sequence of NSm may be present or absent.

The term "L-genome segment" refers to a substantially complete L-genome segment. The term "substantially complete" is used to indicate that the L genome segment comprises cis-acting elements that mediate replication of the L genome segment and that mediate functional expression of the RdRp gene. The term "substantially complete" indicates that sequences that are not involved in replication of the L genome segment or in functional expression of the RdRp gene may be deleted or substituted. The term "functional expression" refers to expression of an RdRp protein, a viral RNA-dependent RNA polymerase, which is able to mediate replication and transcription of a bunyavirus genome segment or bunyavirus minigenome.

The term "S genome segment comprising the N gene" refers to an S genome segment, comprising the UTRs of both the 3' and the 5' end of the S genome segment and at least the nucleotide sequences for expression of the N protein, such as nucleotide sequences for transcription of the N-gene and translation of the N-gene-transcript. The term "S genome segment from which the NSs and N coding regions have been functionally inactivated" refers to an S genome segment, comprising the 3' and 5' UTRs and the untranslated intergenic region of the S genome segment.

The term "M genome segment", as used in the present application, refers to an M genome segment comprising the UTRs of both the 3' and the 5' end of the M genome segment, of which at least one of the glycoproteins Gn and Gc has been functionally inactivated. In one embodiment, said M genome segment is a minigenome segment.

The term "minigenome" refers to an RNA molecule that comprises the 5' and 3' UTRs of a bunyavirus genome segment that functions in replication of the segment, but which lacks at least one bunyavirus coding region that is present on the wildtype genome segment. A minigenome may further comprise a foreign gene such as, but not limited to, a marker gene such as a fluorescent protein, beta-glucuronidase, beta-galactosidase, Gaussia luciferase, Renilla luciferase and secreted alkaline phosphatase.

The term "second L genome segment", as used herein, refers to a second viral genomic segment that contains the 3' and 5' UTRs of the L segment. The UTRs serve as promoters for replication of the segment and for transcription of the encoded reading frame. In addition, each genome segment exhibits a pseudo-circular structure due to the presence of the partially complementary 5' and 3' UTRs, referred to as "panhandle" sequences. The term "second M genome segment", as used herein, refers to a second viral genomic segment that contains the UTRs of the M segment on both the 3' and the 5' ends. The term "second S genome segment", as used herein, refers to a second viral genome segment that contains the UTRs of the S segment on the 3' and the 5' ends.

Similarly, the terms "third L genome segment" and "third S genome segment" as used herein, refer to a third viral genome segment that contains the UTRs of the L segment or the S segment, respectively, on the 3' and the 5' ends. The term "UTR" is known in the art and refers to the untranslated regions at the terminal ends of the viral RNA. The terms "second and third genome segment" include a second and third minigenome segment.

The present invention is directed to bunyaviruses with segmented glycoprotein precursor (GPC) genes. The invention is based on the expression of the coding sequences for the structural glycoproteins (NSm)Gn and Gc from separate genome segments. By this method, viruses can be created that contain four, instead of three genome segments, which retain high replicating efficiencies in vitro but lack the ability to spread efficiently in vivo, especially in arthropods. The limited spread of these viruses in vivo holds promise as veterinary and human vaccines.

In a wildtype bunyavirus, transcription and subsequent translation of the M genome segment results in the synthesis of a precursor protein that is processed into the structural glycoproteins Gn and Gc as well as a 14-kDa nonstructural protein named NSm and a 78-kDa protein, which is believed to be a minor structural protein (De Boer et al., 2012. J Virol 86: 13767-13771). It is relevant to note that the M segment open reading frame (ORF) contains five in-frame start codons. Four of these AUG codons, AUG-1, 2, 4 and 5, were shown to be used as translation initiation sites (Suzich et al., 1990. J Virol 64: 1549-1555). Translation from the first AUG results in the production of a polyprotein that is co-translationally cleaved into the 78-kDa protein (also referred to as "NSm1") and the Gc protein (Gerrard and Nichol, 2007. Virology 357: 124-133) (see FIG. 1). Translation initiation at the second AUG results in the 14-kDa NSm protein as well as the Gn and Gc glycoproteins, whereas translation from AUG-4 or -5 results only in Gn and Gc. The Gn and Gc proteins form heterodimers and subsequently capsomers, presumably already in the endoplasmic reticulum. In the mature virus particle, Gn and Gc are believed to function as the receptor binding protein and viral fusion protein respectively (Dessau et al., 2013. Proc Natl Acad Sci USA 110: 1696-1701; de Boer et al., 2012. J Virol 86: 13642-13652).

Expression of Gn and Gc from the GPC gene results in the assembly of Gn and Gc into particles morphologically resembling the authentic virus, even in the absence of genome segments. These particles are referred to as virus-like particles (VLPs) (De Boer et al., 2010. Vaccine 28: 2330-2339; Habjan et al., 2009. Virology 385: 400-408). We previously demonstrated that transfection of replicon cells containing L and S segments with a GPC expression plasmid results in the assembly and secretion of infectious replicon particles that where shown to resemble phenotypically an authentic virus (Kortekaas et al., 2011. J Virol 85: 12622-12630; de Boer et al., 2012. J Virol 86: 13642-52; De Boer et al., 2012. J Virol 2012 86: 13767-71).

To generate a bunyavirus with a segmented glycoprotein precursor (GPC) gene, the coding sequences for the structural glycoproteins NSmGn and Gc, or for Gn and Gc, are separated and expressed from different genome segments. The coding sequence of glycoprotein Gc is preceded by an artificial AUG start codon, preferably embedded in a Kozak consensus sequence (gccRccAUGG; whereby R indicates a purine). The independent glycoprotein expression cassettes are positioned on separate genomic segments, selected from a genomic L segment and M segment, an L segment and a S segment, an M segment and a S segment, two L segments, two M segments or two S segments. cDNAs of the bunyavirus L, S and M genome segments, including second and third genome segments, when present, are preferably present in a plasmid vector in the genomic-sense orientation or in the antigenomic-sense orientation, and are transfected into relevant cells for generation of a bunyavirus, as has been described (Kortekaas et al., 2011. J Virol 85: 12622-12630). When transcription plasmids encode the genome segments in genomic-sense orientation, a bunyavirus is created by co-transfection of expression plasmids providing the N protein, the L protein and, preferably, the GPC.

A preferred bunyavirus according to the invention comprises four genome segments of which each segment encodes an essential gene. The S segment encodes the N protein and the L segment encodes the RdRp protein. The (NSm)Gn and Gc genes are separately expressed from different L, preferably different S, more preferably different M-type minigenomes, or a combination thereof. The production of progeny virions depends on infection of a cell with a single virus particle containing all four genome segment, or a co-infection of a single cell with two or more replicon particles together delivering all four genome segments. Co-transfection with transcription plasmids encoding the L segment, the S segment (containing or lacking NSs) and two M-type minigenomes, one expressing NSmGn and one expressing Gc, results in infectious particles that can be produced to titers of $10^7$ TCID$_{50}$/ml.

We have found that a four-segmented bunyavirus is incapable of spreading among insect cells, particularly when infection is performed at low moi (FIG. 6). Thus, it is likely that a bunyavirus with a segmented GPC, preferably a four-segmented bunyavirus, is not amplified in arthropod vectors that come into contact with the vaccine virus when feeding on a vaccinated individual. Re assortment of genome segments of the vaccine virus and field virus in arthropod vectors is thereby also prevented.

The term moi refers to the ratio of virus particles, preferably infectious virus particles, to target cells. Using a moi of 5 or less, such as 2, 1, 0.5 and 0.1, a number of cells will receive only one virus particle. For example, at an MOI of 1, 37% of cells receive no virus particle, 37% of cells receive one virus particle, and 26% of cells are multiply infected, while at an moi of 0.1, 90% of cells receive no virus particle, 10% of cells receive one virus particle and almost no cells are multiply infected. The term "low moi" indicates that the ratio of infectious virus particles to target cells is below 1, more preferably below 0.5, more preferably below 0.1, more preferably below 0.01, more preferably below 0.001, more preferably below 0.0001.

By combining a segmented GPC gene with a complete deletion of the major virulence factor, NSs, an optimally safe vaccine virus will be generated. The major inventive step is the successful rescue of a (nonspreading) bunyavirus using a segmented glycoprotein precursor gene, where each of the glycoprotein coding regions is expressed from different (S, M or L) genome segments or minigenomes.

The (NSm)Gn and Gc coding regions may be divided over two S segments. Combining these segments (S-[NSm]Gn and S-Gc) with the L segment resulted in infectious particles. These particles were capable of autonomous spread in vitro, also at low moi, suggesting that in this case, virus is produced that contains two S-type genome segments and one L genome segment. Although the product is an autonomously replicating virus, virus replication was reduced in vitro, suggesting that this three-segment virus will be attenuated in vivo. Deletion of the NSs gene will result in an optimally safe virus with the added advantage that no M segment is present. The resulting virus can therefore not donate an M segment to a field virus by means of reassortment.

The term "functionally inactivated", as used herein, refers to a genetic alteration that abolishes expression of (NSm)Gn and/or Gc from the M genome segment. Said alteration is either an insertion, a point mutation, or, preferably, two or more point mutations, or, more preferably, a deletion. The term "deletion" covers the replacement of nucleotide sequences in the coding part of (NSm)Gn and/or Gc for other nucleotide sequences. A preferred deletion covers more than 10 nucleotides. A preferred deletion is a single, large deletion or a combination of several deletions. Most preferred is a complete deletion of the (NSm)Gn and/or Gc gene.

The term "functional deletion", as used herein, refers to a genetic alteration that abolishes expression of NSs. Said alteration is either an insertion, a point mutation, or, preferably, two or more point mutations, or, more preferably, a deletion. The term "deletion" covers the replacement of nucleotide sequences in the NSs-coding part of the S-segment. A preferred deletion covers more than 10 nucleotides. This helps to ensure that the virus does not revert back to a propagation-competent, pathogenic and/or transmittable phenotype known as 'reverse to virulence' or 'genetic drifting'. A preferred deletion is a single, large deletion or a combination of several deletions. Again, this helps to ensure that the virus does not revert back to a propagation-competent, pathogenic and/or transmittable phenotype. Most preferred is a complete deletion of the NSs gene. Alternatively, the NSs gene can be replaced by the corresponding gene from a heterologous bunyavirus such as Punta Toro virus or Sandfly fever Sicilian virus (Lihoradova et al. 2013. PLoS Negl Trop Dis 7:e2181).

Separated expression of (NSm)Gn and Gc from two different genome segments results in the production of an optimally safe vaccine virus. The impaired growth and/or impaired genome replication in vivo will allow the vaccinated animal to mount an effective immune response, restricting dissemination of the vaccine virus in the vaccinated animal and providing protection from wildtype bunyavirus. A most preferred bunyavirus according to the invention comprises a bunyavirus L genome segment; a bunyavirus S genome segment or part of a S genome segment comprising at least the N gene and the 3' and 5' UTRs; and a bunyavirus M genome segment from which the NSmGn or Gc coding region has been functionally inactivated, whereby the NSmGn or Gc coding region that is deleted from the M genome segment is functionally present on a second M genome segment or on a second S segment.

The bunyavirus L genome segment and/or the S genome segment and/or, when present, the M genome segment, of a preferred bunyavirus according to the invention comprises a foreign gene. Said foreign gene is preferably selected from those encoding N, Gn or Gc, of another bunyavirus of the Phlebovirus, Nairovirus, Orthobunyavirus or Hantavirus genus.

In a preferred method according the invention, one or more of the bunyavirus L genome segment, the S genome segment, and/or, the M genome segment comprises a foreign gene. Said foreign gene is preferably derived from an organism that is a transmitter of an infectious disease. Said organism is preferably selected from adenovirus, African horsesickness virus, African swine fever, Bluetongue virus, Border disease virus, Borna virus, Bovine viral diarrhoe virus, Bovine respiratory syncytial virus, Cache Valley fever virus, Chikungunya virus, Chrysomya bezziana, Classical swine fever, Crimean-Congo hemorrhagic fever virus, Nairobi sheep disease virus, Cochliomyia hominivorax, Coronavirus, Cytomegalovirus, Dengue virus, Eastern equine encephalitis virus, Ebola virus, Equine encephalomyelitis virus, Equine encephalosis virus, Foot and mouth disease virus, Goat pox virus, Hantaanvirus, Sin Nombre virus, Hendra virus, Hepatitis A virus, Hepatitis B virus, Hepatitis C virus, Hepatitis E virus, Herpes simplex virus, Highly pathogenic avian influenza virus, Human immunodeficiency virus, Human parainfluenza virus, Influenza virus, Japanese encephalitis virus, Kaposi's sarcoma-associated herpesvirus, Lassa virus, Lujo virus, Marburg virus, Marsilia virus, Measles virus, Monkeypox virus, Mumps virus, Nipah virus, Papillomavirus, Papova virus, Peste des petits ruminants, Polio virus, Polyomavirus, Rabies virus, Respiratory syncytial virus, Rhinovirus, Rinderpest virus, Rotavirus, Rubella virus, Sandfly fever Naples virus, Sandfly fever Sicilian virus, SARS coronavirus, Sheep pox virus, Simian immunodeficiency virus, Smallpox virus, St. Louis encephalitis virus, Toscana virus, Varicella-zoster virus, West Nile virus, Western equine encephalitis virus, Yellow fever virus, *Bacillus anthracis, Bordetella pertussis, Brucella* spp., *Campylobacter jujuni, Chlamydia trachomatis, Clostridium botulinum, Coxiella burnettii, Francisella tularensis,* Group B *streptococcus, Streptococcus suis, Legionella pneumophila, Leptospira* spp., *Mycobacterium leprae, Mycobacterium tuberculosis, Mycobacterium ulcerans, Neisseria meningitidis, Salmonella, Shigella* spp., *Trypanosoma cruzi, Vibrio cholerae, Yersinia pestis, Mycoplasma mycoides, Plasmodium malariae, Plasmodium ovale, Plasmodium* ssp., *Plasmodium vivax, Taenia solium, Taenia* spp., and *Trypanosoma brucei.*

A bunyavirus according to the invention is preferably selected from the genera Hantavirus, Nairovirus, Orthobunyavirus, and Phlebovirus, which include numerous virus species capable of causing severe disease in both animals and humans. Preferred viruses are Sin Nombre virus (SNV) and Dobrava-Belgrade virus (DOBV) (both of the Hantavirus genus), Crimean-Congo hemorrhagic fever virus (CCHFV) and Dugbe virus (both of the Nairovirus genus), Schmallenberg virus, Bunyamwera virus, Shuni virus and Oropouche virus (Orthobunyavirus), Rift Valley fever virus (RVFV, Phlebovirus genus) and further members of the Phlebovirus genus: Toscana virus, Sandfly fever Naples virus, Sandfly fever Sicilian virus, Punta Toro virus, Uukuniemi virus, Massilia virus and severe fever with thrombocytopenia syndrome (SFTS) virus. Further preferred bunyaviruses include, but are not limited to, viruses of the Dera Ghazi Khan virus Group, the Hughes virus Group, Nairobi sheep disease virus Group, Qalyub virus Group, Sakhalin virus Group, and the Thiafora virus Group.

A most preferred bunyavirus is selected from the group consisting of Crimean-Congo hemorrhagic fever virus, Shuni virus, SFTS virus, Schmallenberg virus, Bunyamwera virus and Rift Valley fever virus.

A bunyavirus according to the invention preferably is a chimeric virus in which the (NSm)Gn and/or the Gc coding region is derived from a bunyavirus that differs from the bunyavirus from which the L and S genome segments are derived. The resultant chimeric virus may then be used as a vaccine that protects against the virus from which the glycoprotein genes are derived and, preferably, as a bivalent vaccine. A preferred virus according to the invention comprises the (NSm)Gn and Gc coding region from SFTS virus, while the L and S genome segments are derived from a different bunyavirus, for example from Rift Valley fever virus or Uukuniemi virus.

A bunyavirus according to the invention preferably is a chimeric virus in which an additional N coding region is introduced, preferably by replacing the NSs gene on the S segment. The resulting S genome segment thus encodes two N proteins. The heterologous N gene is derived from a bunyavirus that differs from the bunyavirus from which the rest of the genetic material is derived. A preferred additional N coding region is from the CCHF virus. The sequence of a S genome segment encoding the RVFV N protein and the CCHFV N protein is depicted in FIG. 2H. The resultant chimeric virus may then be used as a vaccine that protects against the virus from which the heterologous N gene is derived and, preferably, as a bivalent vaccine. A preferred virus according to the invention comprises the N coding region of the CCHF virus, while the rest of the genetic material is derived from Rift Valley fever virus. The resulting vaccine can be used to vaccinate humans or animals against CCHFV and RVFV.

It is preferred that a NSs coding region on the S genome segment is functionally inactivated in a bunyavirus according to the invention. An important advantage of a bunyavirus according to the invention is that the virus is not capable of spreading in a vaccinated animal and/or arthropod vector. The inability to spread systemically, greatly adds to the safety of such virus. The inability to cause viremia in a vaccinated animal also prevents any concerns about possible transmission of this vaccine by insect vectors (see Moutailler et al. 2010. Vector Borne Zoonotic Dis 10:681-688). A vaccine comprising a bunyavirus according to the invention with a functional deletion of the NSs gene, preferably a complete deletion of the NSs coding region, is considered of optimal safety, due to the lack of this major virulence factor.

The invention further provides a method for producing a bunyavirus according to the invention, the method comprising A) providing a eukaryotic cell with growth medium; and B) infecting the eukaryotic cell with the recombinant bunyavirus according the invention, whereafter the bunyavirus is secreted into the growth medium and can be isolated therefrom.

Said eukaryotic cell is preferably a cell that can easily be infected using standard methods known to the skilled person. Said cell is preferably a eukaryotic cell, preferably a mammalian cell. Suitable cells comprise, for example, Baby Hamster Kidney cells such as BHK-21, Human Embryonic Kidney cells such as HEK293, VERO cells, VERO-E6, MDCK cells, CHO cells, Huh-7, Huh7.5 (Sumpter 2005. J Virol 79:2689-2699), HeLa, SW13 and PER.C6 cells (Fallaux, F. J. et al. 1998. Hum Gene Ther 9: 1909-1917). A preferred cell is BHK-21, or a derivative thereof such a BSR subclone (Sato M, et al. 1977. Arch Virol 54: 333-343) or BSR T7/5 (Buchholz et al., 1999 J Virol 73:251-259.

The invention further provides a composition comprising a bunyavirus according to the invention and a suitable excipient, preferably a suitable pharmaceutically and/or veterinary acceptable excipient such as a carrier, adjuvant or vehicle. Said excipient may comprise vitamins; sugars such as sucrose, lactose, D-mannose, D-fructose, and/or dextrose; amino acids such as, for example, glycerin and asparagine; inorganic salts such as, for example, sodium bicarbonate, aluminum hydroxide, benzethonium chloride, ammonium sulfate, magnesium sulfate, potassium phosphate, sodium phosphate, aluminum phosphate and aluminum potassium sulfate; micro crystalline cellulose, magnesium stearate, cellulose acetate phthalate, human serum albumin, fetal bovine serum, citric acid, iron ammonium citrate, peptone, bovine extract and/or gelatin.

A composition according to the invention preferably is an immunogenic composition, more preferably a composition that provides protection against a subsequent infection with a wildtype bunyavirus. Said protection against wildtype virus is characterized as a reduction of clinical disease, and/or a reduction of replication of wildtype virus in the host. Regarding control or eradication of a disease, protection is defined as reduction of onward spread of wildtype virus by any transmission route, via an arthropod vector, horizontally, vertically, and directly or indirectly. The time to onset of protection and long lasting protection are part of the efficacy of a vaccine. Further, broad protection in case of different virus species or serotypes, as will be provided by chimeric bunyaviruses according to the invention, is also part of efficacy.

The invention also provides a bunyavirus according to the invention, or a composition comprising a bunyavirus according to the invention, for use as a medicament. Said medicament is preferably used for amelioration of a bunyavirus infection in an animal, including human. A medicament comprising a recombinant bunyavirus according the invention may additionally comprise a pharmaceutical acceptable adjuvant, diluent or carrier. A medicament according to the invention is preferably combined with other therapeutic options.

The invention additionally provides a vaccine comprising a bunyavirus according to the invention, or a composition according to the invention. Said vaccine preferably comprises an adjuvant. Adjuvant substances are used to stimulate immunogenicity. Examples of commonly used immunological adjuvants are aluminum salts, immunostimulating complexes (ISCOMS), non-ionic block polymers or copolymers, cytokines (like IL-1, IL-2, IL-7, etc.), saponins, monophosphoryl lipid A (MPLA), muramyl dipeptides, vitamin E, polyacrylate resins, and oil emulsions. Preferably, the adjuvant is a sulfolipopolysaccharide, such as the SLP/S/W adjuvant described in Hilgers et al. Vaccine 1994 12:653-660. A further preferred adjuvant is provided by Montanide adjuvants, for example Montanide ISA 720 which contains a natural metabolizable oil and a highly-refined emulsifier from the mannide monooleate family, andby triterpene, such as squalene, and derivatives and modifications thereof.

The invention additionally provides a method for generating a bunyavirus, the method comprising A) providing a cell with a bunyavirus comprising at least one genome segment functionally encoding a RdRp gene and one genome segment encoding a N gene, and B) providing the cell with at least two further (mini)genome segments selected from L, M, and/or S genome segments comprising separated (NSm)Gn and Gc coding regions, meaning that separated (NSm)Gn and Gc coding regions are functionally present on two separate genome segments, whereby each of the two genome segments comprises either the (NSm)Gn coding region or the Gc coding region. A preferred method comprises A1) providing a cell with a bunyavirus L genome segment; A2) providing the cell with at least part of a bunyavirus S genome segment comprising the N-gene and the 3' and 5' UTRs; and B) providing the cell with at least two further (mini) genome segments selected from L, M, and/or S genome segments comprising separated (NSm)Gn and Gc coding regions, optionally providing the cell with a further M genome segment from which the (NSm)Gn and Gc coding region has been functionally inactivated; wherein the sequence of steps A1, A2, and B is random and all or part of these steps may be performed simultaneously.

Step B comprises steps B1, in which either the (NSm)Gn or the Gc coding region is retained on the M genome segment, and B2 in which both the (NSm)Gn and the Gc coding region are functionally deleted from the M genome segment. Step B1) comprises providing the cell with a M genome segment from which the (NSm)Gn or Gc coding region has been functionally inactivated, whereby the cell is further provided with a second L genome segment, a second M genome segment, or a second S genome segment on which the (NSm)Gn or Gc coding region that is deleted from the M genome segment is functionally present. Step B2) comprises providing the cell with a second and a third L genome segment, a second L genome segment and a second S genome, or a second S genome segment and a third S genome segment, whereby separated NSmGn and Gc coding regions are functionally present either on said second and a third L genome segment, on said second L genome segment and said second S genome segment, or said second S genome segment and said third S genome segment, and optionally a further M genome segment from which the (NSm)Gn and Gc coding region has been functionally inactivated; wherein the sequence of steps A1, A2, and B is random and all or part of these steps may be performed simultaneously.

It is preferred that a cell is provided with a genomic segment by providing the cell with a vector that comprises cDNA of said genomic segment which is flanked at the 5' end by a promoter sequence for a DNA-dependent RNA polymerase. Said promoter sequence for a DNA-dependent RNA polymerase is preferably selected from known promoter sequences of DNA-dependent RNA polymerases such as, but not limited to, the promoter sequence of a eukaryotic RNA polymerase I such as, for example, a promoter for murine RNA polymerase I, the previously reported Pol-I/Pol-II-based reverse genetics system (Habjan et al., 2008. J Gen Virol 89: 2157-2166), and the bacteriophage polymerases SP6, T3 and T7. Although the description and the claims refer to T7polymerase, it is to be understood that the invention is not limited to T7 polymerase but includes other DNA-dependent RNA polymerase such as, for example, T3 polymerase and SP6 polymerase. A preferred promoter sequence for a T7 polymerase is TAATACGACTCACTATAG (SEQ ID NO: 1).

Copy DNA of bunyavirus genomic segments or fragments thereof are flanked at the 3' ends by a cDNA encoding a ribozyme sequence that mediates 3' end formation of the RNA by self-cleavage of the nascent RNA. A preferred ribozyme sequence is a hepatitis delta virus (HDV) ribozyme sequence. A termination sequence that mediates termination of the DNA-dependent RNA polymerase may further be present distal to the cDNA encoding the ribozyme sequence. In a preferred embodiment, the DNA-dependent RNA polymerase is T7 polymerase and the termination sequence is a T7 transcription termination sequence. Promoter sequences for DNA-dependent RNA polymerases, such as T7 polymerase, and termination sequences such as a T7 transcription termination sequence, are known to the skilled person.

In a preferred method according to the invention, a cell is provided with a genomic segment by providing the cell with a vector that comprises cDNA of said genomic segment which is flanked by a T7 promoter and cDNA of a ribozyme. Said method additionally comprises providing the cell with a T7 polymerase.

A cell is provided with sufficient T7 polymerase by freshly transfecting or infecting the eukaryotic cell with an expression vector that encodes the T7 polymerase. In one embodiment, the expression vector is a plasmid that encodes the T7 polymerase. Suitable plasmids are, for example, pCAGGS, and pcDNA. In a preferred embodiment, T7-expressing cells are infected with a non-recombinant poxvirus, preferably an avipoxvirus such as pigeonpox virus or fowlpox virus. Infection by the poxvirus will stimulate capping of T7 transcripts, which stimulates protein expression. In another preferred embodiment, the expression vector is a recombinant virus or viral vector that encodes the T7 polymerase. A suitable virus or viral vector is, for example, a replication defective retroviral vector such as a lentiviral vector, for example a HIV-based vector or an EIAV-based vector, or a replication defective MMLV-based vector. A further suitable virus or viral vector is provided by a replication defective adenoviral vector and a baculovirus vector. A preferred virus or viral vector is a replication defective poxvirus such as, for example, a vaccinia-based virus. In a most preferred method, the eukaryotic cell is provided with sufficient T7 polymerase by infecting the eukaryotic cell with a fowlpox virus (FPV)-based expression vector that encodes the T7 polymerase. The FPV may be replication competent or replication defective.

An advantage of a FPV is that it belongs to the genus Avipoxvirus and is capable of spreading in avian cells. In non-avian cells such as, for example, mammalian cells, FPV replication is abortive without any evidence of production of infectious virus. Therefore, when the eukaryotic cell is a non-avian eukaryotic cell, a replication competent FPV-based expression vector or a replication deficient FPV-based expression vector is preferably used for a method of the invention. When the eukaryotic cell is an avian eukaryotic cell, it is preferred that a replication deficient FPV-based expression vector is used for a method of the invention.

Said cell preferably is a eukaryotic cell. Said eukaryotic cell is preferably a cell that can easily be infected using standard methods known to the skilled person. Said cell is preferably a eukaryotic cell, preferably a mammalian cell. Suitable insect cells comprise, for example, Baby Hamster Kidney cells such as BHK-21, Human Embryonic Kidney cells such as HEK293, VERO cells, VERO-E6 cells, MDCK cells, CHO cells, HuH-7, Huh7.5 (Sumpter 2005. J Virol 79:2689-2699), HeLa, SW13 and PER.C6 cells (Fallaux, F. J. et al. 1998. Hum Gene Ther 9: 1909-1917). A preferred cell is BHK-21, or a derivative thereof such a BSR subclone (Sato M, et al. 1977. Arch Virol 54: 333-343) or BSR T7/5 (Buchholz et al., 1999 J Virol 73:251-259).

FIGURE LEGENDS

FIG. 1. Membrane topology and proteolytic processing of the RVFV glycoprotein precursor. Shown are the translation products starting from the in-frame AUG codons 1,2 and ⅘ of the open reading frame. The 'Y' symbols indicate the predicted N-linked glycosylation sites. The red 'Y' symbol is known not to be utilized. The 14-kDa, 78-kDa, Gn and Gc proteins are indicated, as well as the predicted transmembrane spanning regions.

FIG. 2. Schematic representations of relevant plasmid sequences of A) pCAGGSNSmGn, B) pCAGGS-Gn, C) pCAGGS-Gc, D) pUC57-S-NSmGn, E) pUC57-S-Gc, F) pUC57-S-delNSs, G) pUC57-M-NSmGn, H) pUC57-M-Gc, I) pUC57-S-CCHFV-N, J) pUC57-S-NSmGn (non-optimized NSmGn sequence), and K) pUC57-S-Gc (non-optimized Gc sequence). Cartoons were produced using SnapGene® software (from GSL Biotech; available at snapgene.com). Sequences in bold indicate start and stop codons whereas underlined sequences represent restriction enzyme sites. Shaded sequences represent untranslated regions. The RVFV sequences in pUC57 plasmids are flanked by a T7 promoter and a ribozyme sequence.

FIG. 3. Replicon particle production by BHK-Rep2 cells. BHK-Rep2 cells stably maintaining the L and S-eGFP genome segments of RVFV were transfected with either pCAGGS-M, co-transfected with pCAGGS-Gn and pCAGGS-Gc, or co-transfected with pCAGGS-NSmGn and pCAGGS-Gc. One day post transfection supernatants were titrated on BHK-21 cells and titers of replicon particle progeny were determined.

FIG. 4. Visualization of RVFV containing two S genome segments. BHK-21 cells were infected with RVFV-SSL and after 2 days Gn and Gc expression was visualized using IPMA.

FIG. 5. Visualization of RVFV containing four genome segments. BSR T7/5 cells were infected with RVFV-SMML-NSs, RVFV-SMML-delNSs or RVFV-SMML-eGFP and after 2 days Gn and Gc expression was visualized using IPMA.

FIG. 6. Growth curves of RVFV-eGFP and RVFV-SMML-eGFP. BSR T7/5 and C6/36 cells were infected with the listed viruses with an moi of 0.001. Supernatants were collected at the indicated time points and titrated on BSR T7/5 cells.

Figure 7:
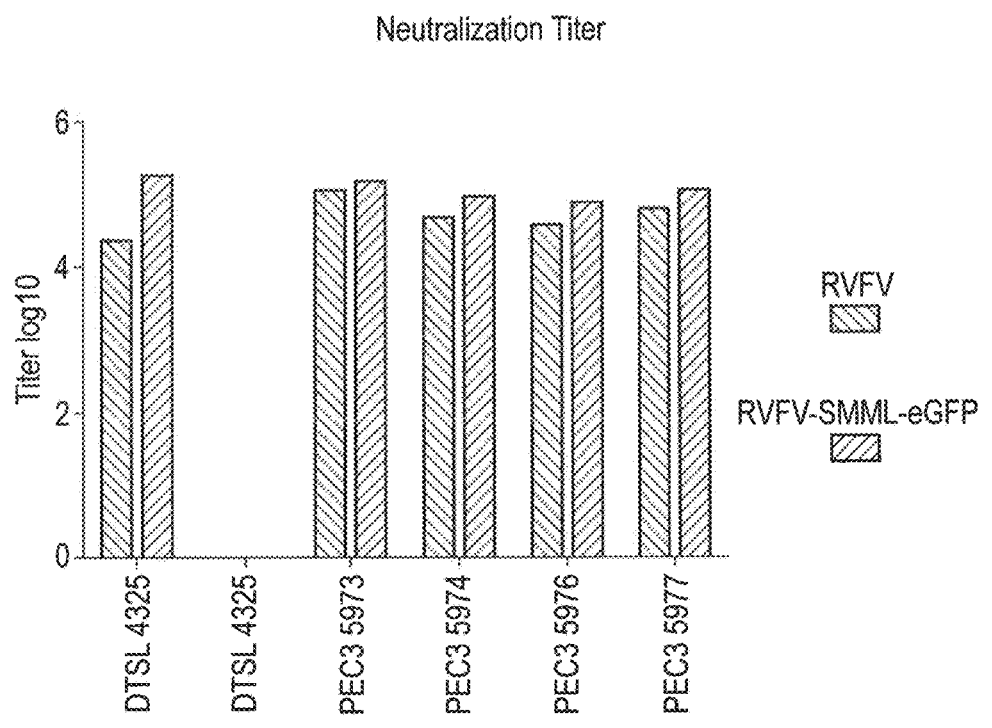

FIG. 7. RVFV-SMML-eGFP-based virus neutralization test. Sera from experimentally infected sheep were analysed for RVFV neutralizing antibodies using a conventional VNT test and a RVFV-SMML-eGFP-based VNT.

FIG. 8. Creation of RVFV replicon particles using a segmented glycoprotein precursor gene. A) Schematic presentation of M-segment encoded proteins and protein processing. The localization of the segmentation site is indicated with an arrow. B) Schematic presentation of the NSR read-out system. BHK-Rep2 cells, stably maintaining replicating RVFV L and SeGFP genome segments were transfected with pCAGGS expression plasmids encoding Gn, (NSm)Gn, Gc or NSmGnGc. C) One day post transfection the titer of NSR progeny was determined in the supernatant. Bars represent means+standard error (SE) of three independent experiments.

FIG. 9. Rescue of RVFV-LMS-split and RVFV-LSS. A) Schematic presentation of the wild-type RVFV genome and the RVFV-LMS-split and RVFV-LSS variants. B) IFA (Gn antigen) of BSR cells infected with RVFV, RVFV-LMS-split or RVFV-LSS 48 h post infection. C) Northern blot analysis of RVFV, RVFV-LMS-split and RVFV-LSS RNA isolated of supernatants of infected cells. Used probes are indicated on the right. D) Growth curve of indicated viruses on BSR cells.

FIG. 10. Rescue of RVFV-4S A) Schematic presentation of the wildtype RVFV genome and of 4 segment variants. B) IFA (Gn antigen) of BSR cells infected with all the variants 48 h post infection. C) Northern blot analysis of RNA isolated from supernatants of RVFV-4S infected cells. Used probes are indicated at the right. D) Growth curve of indicated viruses on BSR cells.

Figure 11:
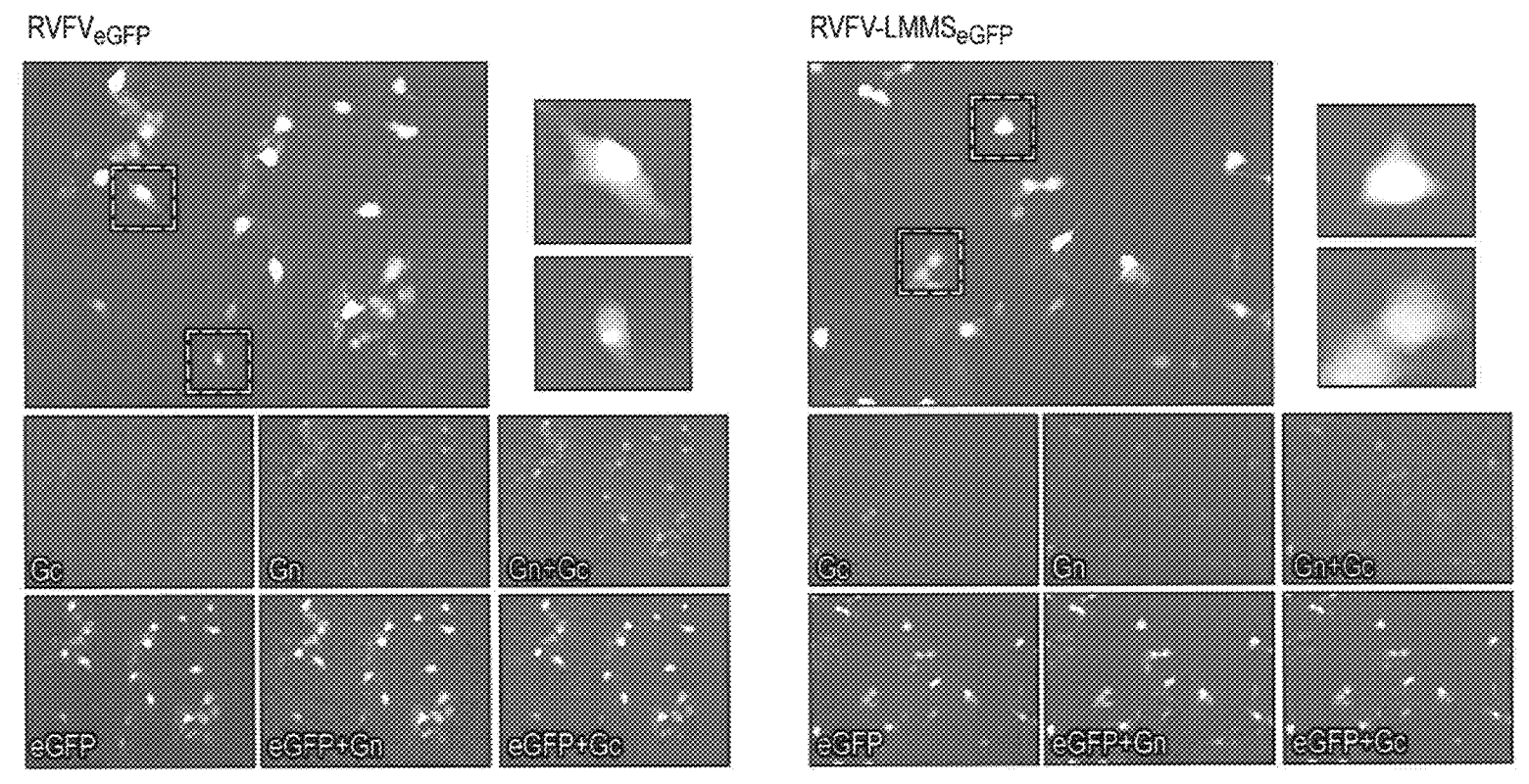

FIG. 11. Localization of Gn and Gc in cells infected with RVFV-4S. BSR cells were infected at MOI 0.1 with $RVFV_{eGFP}$ or $RVFV-LMMS_{eGFP}$. 16 h post infection cells were fixated and Gn and Gc antigen was detected.

Figure 12:
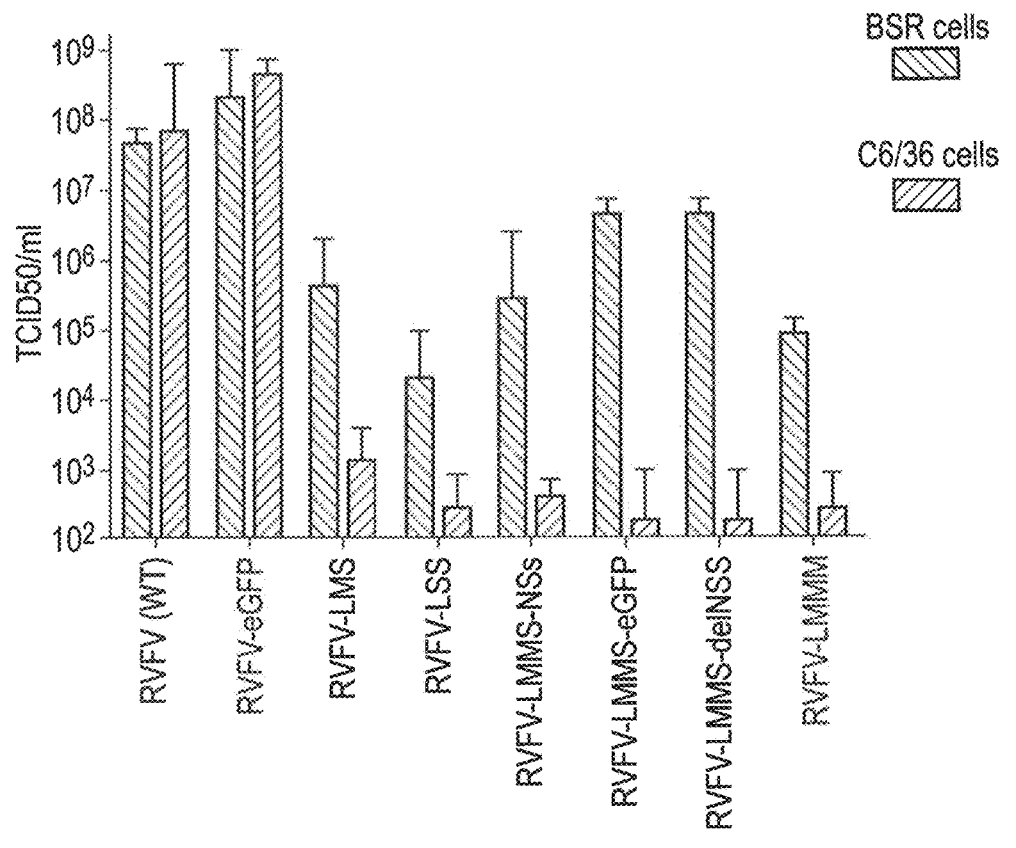

FIG. 12. Growth of RVFV variants in insect cells. C6/36 cells and BSR cells were infected with the RVFV variants as indicated at an MOI of 0.01. Supernatants were collected at 4 days post infection and titrated on BSR cells. Bars represent means+SE of three independent experiments.

FIG. 13. Virulence of RVFV-4S. A) Survival curve of mice inoculated with a high or a low dose of $RVFV-LMMS_{NSs}$ via intraperitoneal route. As a control, mice were challenged with a low dose of authentic RVFV. Virus dissemination in the liver (B) and brain (C) of mice euthanized at different time points was determined by qRT-PCR.

FIG. 14. Vaccination-challenge experiment. A) Survival curve of mice inoculated with culture medium (mock), $NSR_{Gn}$, $RVFV-LMMS_{eGFP}$ or $RVFV-LMMS_{delNSs}$. Three weeks post vaccination mice were challenged with a lethal dose of wild-type RVFV. B) RVFV neutralization titers present in sera the day before challenge. Virus dissemination into the liver (C) and brain (D) was determined by qRT-PCR.

FIG. 15. Rectal temperatures of vaccinated (A) and mock-vaccinated (B) lambs before and after challenge with RVFV on day post vaccination (DPV) 21. Rectal body temperatures (° C.) were determined daily. Fever was defined as a body temperature above 40.5° C. (interrupted line). Rectal body temperatures of vaccinated lambs are depicted as averages (n=7) with SD. Rectal body temperatures of mock-vaccinated lambs determined after DPV 23, 24 and 27 are depicted as averages of 6, 5 and 4 measurements, respectively, since a lamb from this group died on each of these days.

FIG. 16. Monitoring of viremia in vaccinated (A) and mock-vaccinated (B) lambs by qRT-PCR. Viral RNA was detected by qRT-PCR in plasma samples obtained at different days post challenge with RVFV.

Figure 17A:
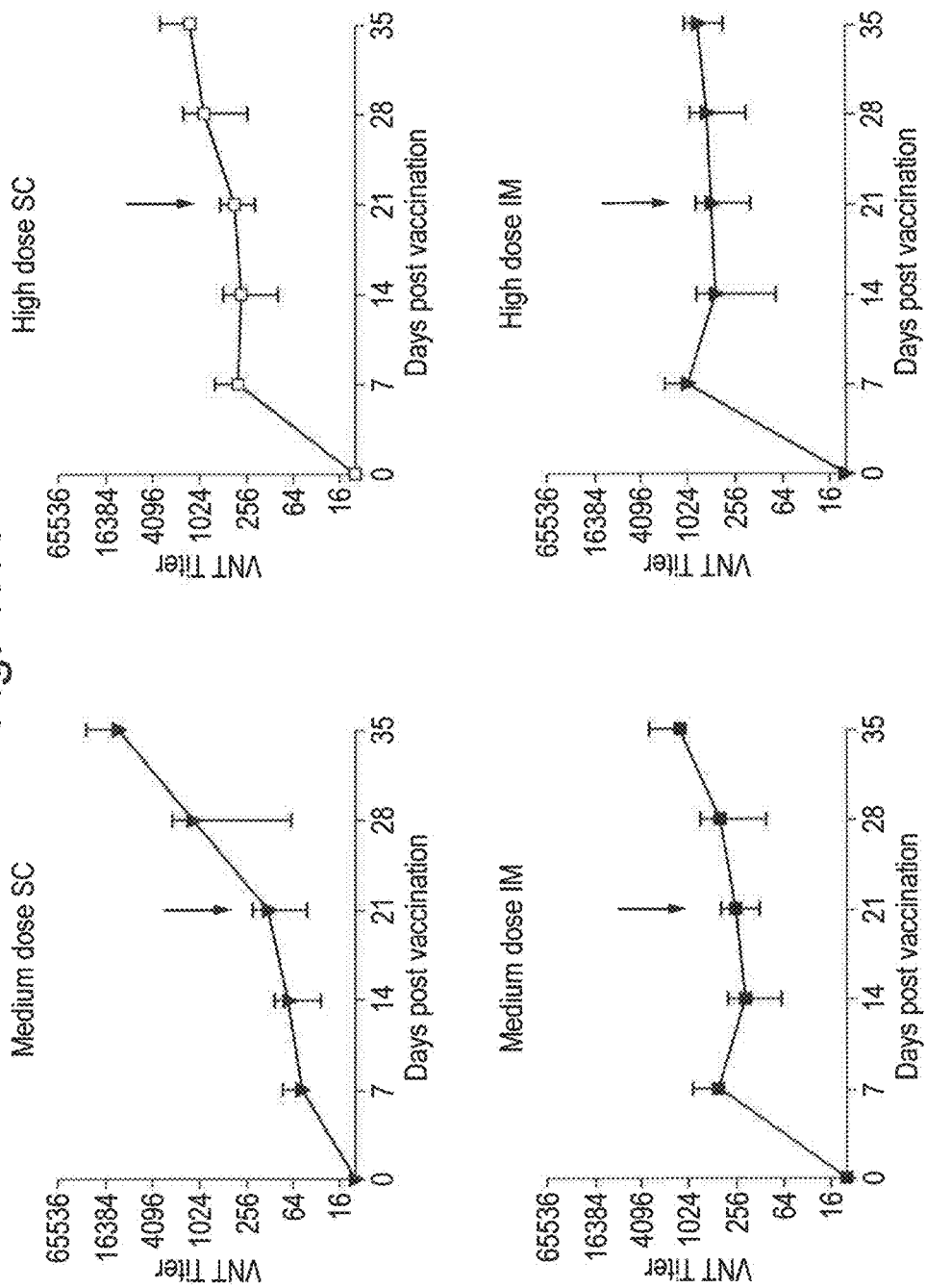
Figure 17B:
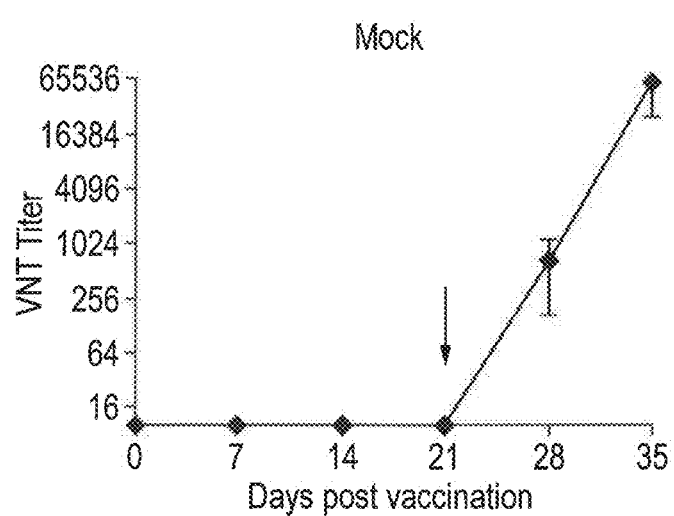

FIG. 17. Results from virus neutralization tests performed with sera obtained from vaccinated- or mock-vaccinated lambs at different time points after vaccination and challenge infection. Errors bars represent standard deviations. The detection limit of the assay is a VNT titer of 10. The arrow indicates the day of challenge.

EXAMPLES

Example 1

Materials and Methods
Cells and Growth Conditions.

All mammalian cell lines were routinely grown at 37° C. with 5% CO2. BHK cells were grown in Glasgow Minimum Essential Medium (GMEM; Invitrogen, Bleiswijk, The Netherlands) supplemented with 4% tryptose phosphate broth (TPH; Invitrogen), 1% non-essential amino acids (NEAA; Invitrogen), 5-10% fetal bovine serum (FBS; Bodinco, Alkmaar, The Netherlands) and 1% penicillin-streptomycin (Invitrogen). BSR-T7/5 cells, kindly provided by Prof. Dr. K. Conzelmann (Max von Pettenkofer-Institut, Munchen, Germany) and BHK-Rep2 cells (BHK-21 cells constitutively replicating L and S genome segments of RVFV isolate 35/74) were grown in the same medium as used for BHK cells, supplemented with 1 mg/ml geneticin. Cell culture in the BSL-3 laboratory was performed in closed containers and therefore required the use of CO2-independent medium (CIM; Invitrogen). For these experiments, the culture medium was replaced with CIM supplemented with 5% FBS and 1% penicillin-streptomycin. *Aedes albopictus* (C6/36) mosquito cells [9] were grown in L15 medium (Invitrogen) supplemented with 10% FBS, 1% NEAA, 2% TPH and 1% penicillin-streptomycin at 28° C. without CO2. QM5 cells were grown in QT35 medium (Invitrogen) supplemented with 5% FBS and 1% penicillin-streptomycin.

Viruses

RVFV strain 35/74 was isolated from the liver of a sheep that died during a RVFV outbreak in the Free State province of South Africa in 1974 (Barnard 1979. J S Mr Vet Assoc 50: 155) and was kindly provided by the Agricultural Research Council-Onderstepoort Veterinary Institute (Pretoria, South Africa). The virus was passaged four times in suckling mice by intra-cerebral injection and three times on BHK-21 cells. The virus was routinely grown on BHK-21 cells. Sequences of the L, M, and S genome segments can be found in GenBank under accession numbers JF784386, JF784387, and JF784388 respectively.

A fowlpox virus that expresses T7 polymerase, named fpEFLT7pol [11], from hereafter referred to as FP-T7, was kindly provided by the Institute for Animal Health (IAH, Compton, UK; Britton et al., J Gen Virol. 1996; 77:963-967.). The virus was grown and titrated on QM5 cells.

Titration

Virus titers were determined by serial dilution on cells of interest in 96 wells plates (10.000-40.000 cells/well). Two to five days post infection cytopathologic effect (CPE) was scored or virus growth was visualized using immunoperoxidase monolayer assay (IPMA, see below). Titers were determined as TCID50 as described (Kärber., 1931. Arch Exp Path Pharmak 162: 480-483; and Spearman, 19908. Br J Psychol 2: 227-242).

Plasmids

Expression Plasmids pGAGGS expression plasmids, containing a CMV immediate enhancer/chicken β-actin (CAG) promoter (Niwa et al, 1991, Gene 108: 193-199) were used for transient expression of genes of interest (GOI). pCAGGS-M (Kortekaas et al., 2011. J Virol 85: 12622-12630) contains the ORF of the M-segment of RVFV isolate 35/74, starting at the first methionine codon. pCAGGS-NSmGn contains the NSmGn coding region of the M segment of RVFV strain 35/74 without the signal sequence of Gc (FIG. 2A). pCAGGS-Gn contains the Gn coding region of the M-segment of RVFV isolate 35/74 without the signal sequence of Gc (FIG. 2B). pCAGGS-Gc contains the Gc coding region of the M-segment of RVFV isolate 35/74 including its N-terminal signal sequence (FIG. 2C). Plasmids were designed to contain sequences optimized for expression in mammalian cells and Kozak consensus sequences were included to optimize expression.

Transcription Plasmids

Figure 2A:
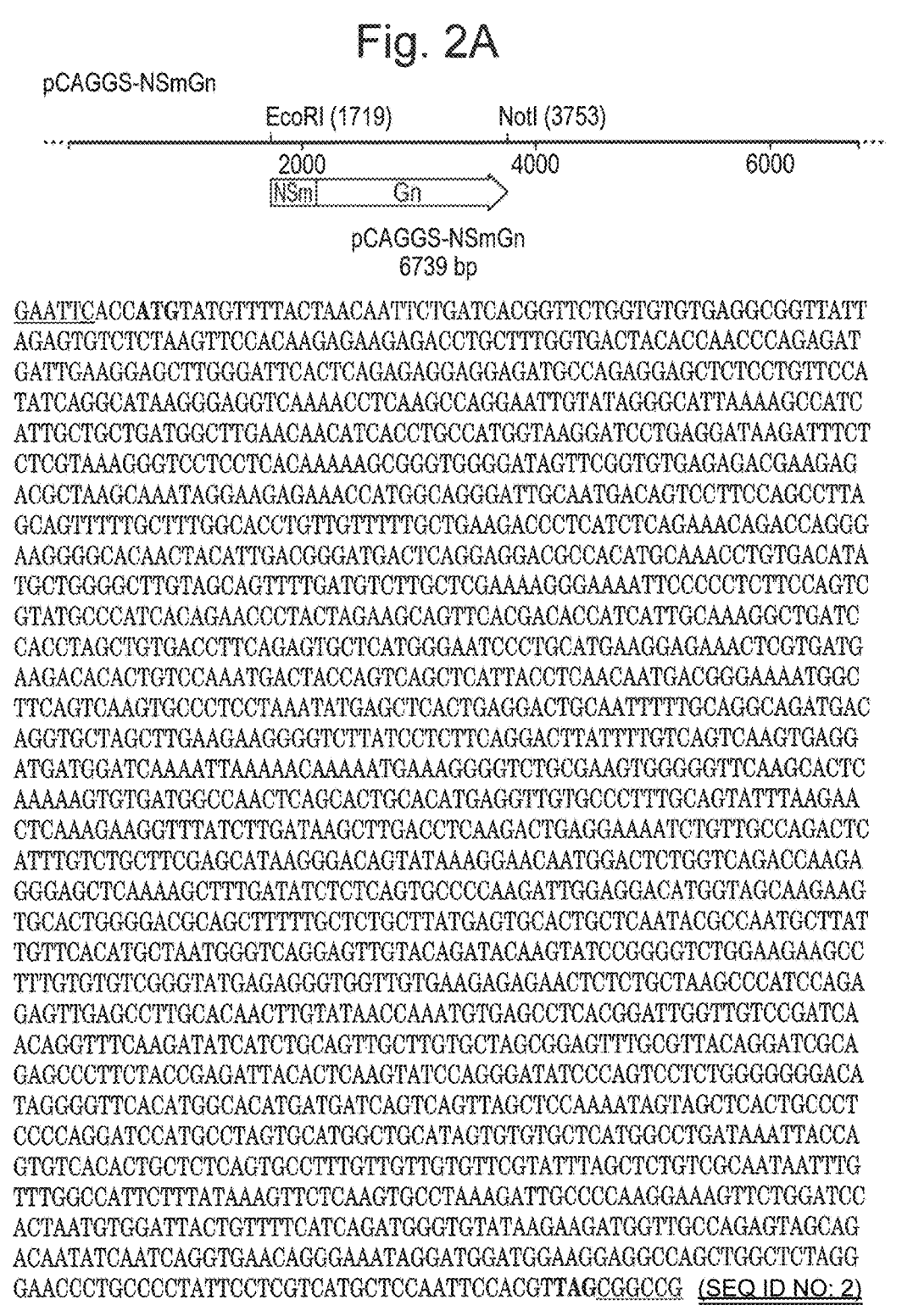
Figure 2G:
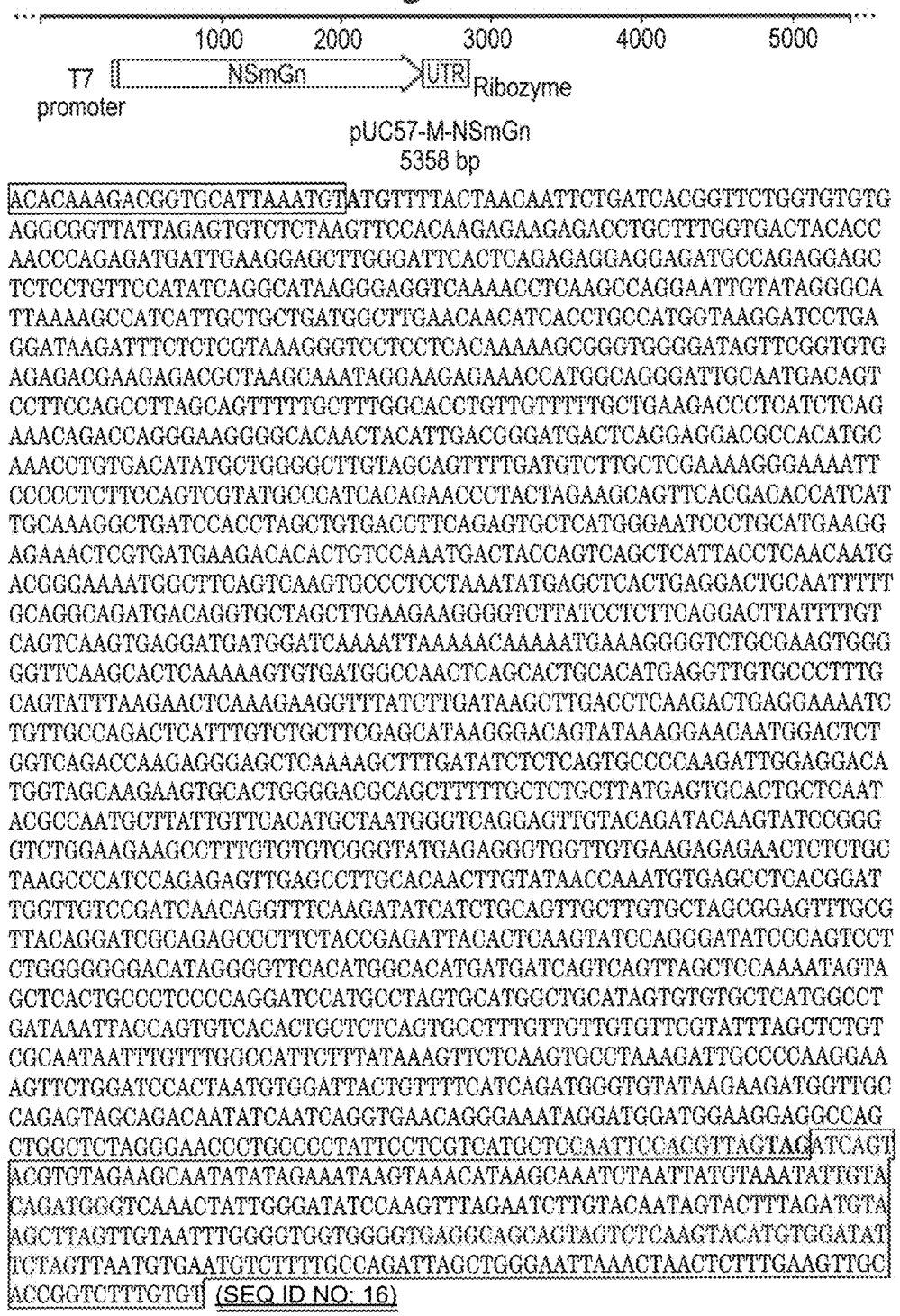

RVFV transcription plasmids, pUC57-S, pUC57-M and pUC57-L (Kortekaas et al., 2011. J Virol 85: 12622-12630) encode the complete S, M or L segment of RVFV isolate 35/74, respectively, including the 3' and 5' UTRs. Transcription of the genome segments is controlled by a minimal T7 promoter. Transcription results in antigenomic-sense RNA genome segments. Plasmid pUC57-S-eGFP plasmid (Kortekaas et al., 2011. J Virol 85: 12622-12630) encodes an S segment RNA in which the NSs gene is replaced in its entirety by the gene encoding enhanced green fluorescent protein (eGFP). pUC57-S-NSmGn and pUC57-S-Gc encode the N protein in antigenomic orientation and the NSmGn protein and Gc protein, respectively, in genomic-sense orientation (FIGS. 2D and 2E). NSmGn and Gc-coding sequences were codon optimized for optimal expression in mammalian cells. The non-optimized pUC57-S-NSmGn and pUC57-S-Gc sequences are depicted in FIGS. 2J and 2K, respectively. The pUC57-S-delNSs plasmid encodes an S segment from which the NSs gene is deleted in its entirety (FIG. 2F). The pUC57-M-NSmGn and pUC57-M-Gc plasmids contain the authentic (non-codon optimized) sequences of NSmGn, respectively Gc, in antigenomic-sense orientation (FIGS. 2G and 2H). Kozak consensus sequences were included for optimal expression.

Immunoperoxidase monolayer assay (IPMA) and immunofluorescence assay (IFA). Monolayers of infected cells were fixed in 4% paraformaldehyde in PBS for 30 minutes and subsequently permeabilized with 100% cold methanol. After blocking the cells with 5% horse serum in PBS for 30 min, cells were incubated with primary antibody in blocking solution. Either a Gn-specific monoclonal antibody (mAb, provided by Dr. Connie Schmaljohn, USAMRIID, Keegan et al., 1986. J Virol 58: 263-270), a Gc rabbit polyclonal antibody (De Boer et al., 2012. J Virol 86: 13642-13652), or an N-specific mAb (F1D11; Kindly provided by Dr. Alejandro Brun, CISA-INIA, Spain; Martin-Folgar et al., MAbs. 2010; 2(3):275-284) was used. As secondary antibodies, HRP-conjugated rabbit anti-mouse IgG, goat anti-rabbit IgG (DAKO, Heverlee, Belgium) or a rabbit anti-mouse Texas Red conjugated antibody (DAKO) was used. All antibody incubations were performed for >1 hour at 37° C. and between antibody incubations cells were washed three times with PBS supplemented with 0.05% Tween 80. Antibody binding was visualized using an EVOS fluorescence microscope (Fisher Scientific) and a 3-amino-9-ethylcarbazole (AEC)-based substrate (DAKO).

Virus Rescue

BSR-T7/5 or BHK-21 cells were seeded on day 0 in 6-well plates (100.000-600.000 cells/well) in GMEM supplemented with 5% FBS. On day 1, cells were infected for one to two hours with FP-T7 (moi≈0.1) in Optimem (Invitrogen) containing 0.2% FBS and were subsequently transfected with 3 µg plasmid DNA (600-1000 ng/plasmid) using jetPEI transfection reagents according the manufactures description (Polyplus, Illkirch, France). Four hours post transfection, medium was replaced by complete CIM or GMEM medium. Three to five days post transfection, supernatants were collected and incubated with freshly seeded BSR-T7/5 or BHK-21 cells. Productive infection was visualized with the EVOS fluorescence microscope by detection of GFP expression or by staining RVFV-specific proteins by IPMA or IFA.

Virus Neutralization Test (VNT)

VNTs were performed with the 4S SLMM-eGFP virus expressing eGFP from the S segment. Sera were obtained from lambs that had previously been experimentally infected with the 35/74 isolate. To confirm the presence of RVFV-specific antibodies, the sera were analyzed with a recombinant N (recN) RVFV enzyme-linked immunosorbent assay (ELISA) (BDSL, Irvine, Ayrshire, Scotland, United Kingdom) prior to analysis by VNT. Serum dilutions were prepared in 96-well plates in 50 µl complete GMEM supplemented with 5% FBS. Culture medium containing ≈200 infectious particles in a 50 µl volume was added to the serum dilutions and the mixture was incubated for 1.5 h at room temperature. Next, 50 µl of CIM growth medium containing 40 000 BHK-21 cells was added to each well. Plates were incubated at 37° C. for 36 to 48 h. Neutralization titers were calculated by the Spearman-Kärber method.

Results

The Glycoprotein Precursor (GPC) is not Essential for Bunyavirus Assembly

The requirement for the (NSm)Gn and Gc glycoproteins of RVFV to be expressed from a polyprotein precursor was evaluated. The ORF encoding the GPC was divided into two non-overlapping ORFs encoding NSmGn and Gc, respectively. Specifically, the GPC gene was segmented at the tyrosine (Y)-675 codon, which is predicted to be the first amino acid of the signal sequence of Gc (Suzich et al., 1990. J Virol 64: 1549-1555; Gerrard and Nichol, 2007. Virology 357(2): 124-133).

To evaluate whether the (NSm)Gn and Gc proteins, expressed from dedicated expression plasmids, are able to package RVFV genome segments into infectious replicon particles, we co-transfected BHK-Rep2 cells (Kortekaas et al., 2011. J Virol 85: 12622-12630) with pCAGGS expression vectors encoding either Gn or NSmGn (pCAGGS-Gn or pCAGGS-NSmGn) and a pCAGGS plasmid encoding Gc (pCAGGS-Gc) and evaluated if replicon particles were produced. As a positive control, BHK-Rep2 cells were transfected with a pCAGGS plasmid encoding the complete GPC (pCAGGS-M) which is known to result in the production of replicon particles (Kortekaas et al., 2011. J Virol 85:

12622-12630). The results show that Gn and Gc, when expressed from two different expression plasmids, are able to package RVFV genome segments into infectious replicon particles (FIG. 3). These experiments resulted in average infectious particle titers of 10E4 TCID50/ml. The presence of the NSm coding region increased the yield of infectious particles to 10E6 TCID50/ml (FIG. 2). Although replicon particle yields when produced with pCAGGS-NSmGn and pCAGGS-Gc were approximately 10 times lower compared to the yields resulting from transfection with pCAGGS-M, the results clearly show that segmentation of the GPC ORF into two dedicated ORFs encoding the (NSm)Gn and Gc glycoproteins, respectively, does not abrogate particle assembly or glycoprotein function. From this, it is concluded that co-translational cleavage of the GPC is not essential for the generation of infectious replicon particles.

Rescue of a RVFV that Expresses NSmGn from the S-Segment

After demonstrating that RVFV L- and S genome segments can efficiently be packaged into infectious replicon particles using the pCAGGS-NSmGn and pCAGGS-Gc expression plasmids, we next investigated if virus can be generated expressing the NSmGn gene and Gc gene from separate genome segments. To this end, a transcription plasmid was created that encodes the Gc gene flanked by the M segment untranslated regions (UTRs, pUC57-M-Gc) and a transcription plasmid was created that encodes an S segment in which the NSs gene is substituted for the NSmGn gene (pUC57-S-NSmGn). BHK cells were infected with FP-T7 and transfected with transcription plasmids pUC57-L, pUC57-M-Gc and pUC57-S-NSmGn. Three days post transfection supernatants were collected and used to inoculated fresh BHK-21 cells. Three days later, CPE was observed, indicating the presence of virus. Titration of the virus showed a yield of 10E6 TCID50/ml. The results of this experiment demonstrate that co-translational cleavage of the GPC is not essential for RVFV particle assembly and glycoprotein function.

The virus based on expression of codon optimized NSmGn from the S-segment is referred to as RVFV-LMS-split-opt Rescue of RVFV Containing Two S-Type Genome Segments Our finding that the GPC is not essential for RVFV provides opportunities to study RVFV genome packaging. We investigated whether RVFV is able to package more than one genome segment of the same type. A plasmid was created that encodes an S segment in which the NSs gene is replaced with the Gc gene (yielding pUC57-S-Gc). FP-T7-infected BHK-21 cells were transfected with pUC57-L, pUC57-S-NSmGn and pUC57-S-Gc. Three days post transfection supernatants were analyzed for the presence of infectious virus by incubation with BHK-21 cells. Three days post incubation CPE was observed and rescue of virus was visualized with IPMA (FIG. 4). Titration of the virus revealed a yield of 10E6 TCID50/ml. The relatively efficient growth of a RVFV containing two S segments suggests that the virus can easily maintain two S-type genome segments.

The two S-segmented virus based on expression of codon optimized NSmGn and Gc from separate S-segments is referred to as RVFV-LSS-opt.

Rescue of Four Segmented RVFV

To further explore RVFV genome packaging, we evaluated if a virus can be rescued that contains 4 genome segments: one L, one S and two additional segments encoding the structural glycoproteins. We selected the M segment for expression of NSmGn and Gc. To this end, two transcription plasmids were created, pUC57-M-NSmGn and pUC57-M-Gc. BSR T7/5 cells were infected with FP-T7 and transfected with transcription plasmids pUC57-L, pUC57-M-NSmGn, pUC57-M-Gc and either pUC57-S, pUC57-S-eGFP or pUC57-S-delNSs. The pUC57-S-eGFP was used to facilitate detection of virus by fluorescence microscopy. The pUC57-delNSs was created by deleting the complete NSs gene from the pUC57-S plasmid. Three days post transfection, supernatants were collected and used to infect BHK cells. First experiments focused on the rescue of eGFP expressing virus, which was monitored using an EVOS fluorescence microscope. The increase in number of fluorescent cells demonstrated that virus was rescued and passage of the supernatant resulted in a virus titer of 10E7 TCID50/ml. Using similar methods, viruses either lacking or containing the NSs gene were rescued, which both yielded titers of 10E7 TCID50/ml. All three viruses were visualized using IPMA (FIG. 5). The successful rescue of a RVFV using four genome segments, named RVFV-SMML (also referred to as RVFV-LMMS), indicates that RVFV is able to maintain more than three genome segments in the virus population. The successful production of virus using this method can be explained by packaging of all four genome segments into a single virus particle or, alternatively, by co-infection of a single cell with two or more particles.

An interesting feature of the RVFV-SMML-eGFP virus is that the virus is not able to spread among insect cells in contrast to RVFV-eGFP (RVFV-eGFP contains the wildtype M genome segment, the wildtype L genome segment and a S genome segment in which the NSs gene is replaced for the gene encoding eGFP) (FIG. 6). RVFV-SMML-eGFP can thus be considered a non-spreading virus in C6/36 cells. In addition, the RVFV-SMML-eGFP virus grows slower in BSR-T7 cells compared to wild type RVFV-eGFP (FIG. 6). We propose that the RVFV-SMML viruses hold great promise as a vaccine that optimally combines the safety of inactivated vaccines with the efficacy of live vaccines. Compared to the previously developed replicon particles, RVFV-SMML viruses offer the advantage of easy production on a variety of mammalian cell types known to be suitable for RVFV production, as no cell line is required that expresses (NSm)Gn and Gc. To obtain optimal safety, the NSs gene in the S segment of RVFV-SMML viruses is either deleted in its entirety or replaced by the eGFP gene. Finally, it is interesting to note that the NSs gene can also be replaced by a gene of interest from another pathogen, offering possibilities to develop multivalent vaccines or vector vaccines.

Use of the RVFV-SMML-eGFP Virus in a Virus Neutralization Test (VNT)

The expression of eGFP by the RVFV-SMML-eGFP virus allows its use in VNTs. To evaluate whether a VNT based on the RVFV-SMML-eGFP virus is of similar specificity and sensitivity as the conventional VNT using the authentic, virulent RVFV virus or the VNT using replicon particles (Kortekaas et al., 2011. J Virol 85: 12622-12630) a panel of sera obtained from sheep experimentally infected with RVFV was tested. Two days post infection with RVFV-SMML-eGFP, reporter gene expression was used as a readout, while CPE was used as a readout in the conventional VNT. The results show that both tests have similar sensitivity (FIG. 7). After further validation, the RVFV-SMML-eGFP-based VNT could be used as an alternative for the conventional VNT. The major advantage of this novel VNT is that the test can be performed outside biosafety containment facilities. A second advantage is that the results of a RVFV-SMML-eGFP VNT are available after 48 hrs, whereas the conventional VNT, which depends on CPE, takes 5-7 days to completion.

Example 2

Materials and Methods
Cells and Viruses

BHK, BHK-Rep2 (Kortekaas et al., 2011. J Virol 85: 12622-12630), BSR-T7/5 (Buchholz et al., 1999. J Virol 73: 251-259) and C6/36 cells were maintained as described previously (Kortekaas et al., 2011. J Virol 85: 12622-12630). All RVFV variants described in this study contain the RVFV strain 35/74 genetic backbone (Kortekaas et al., 2011. J Virol 85: 12622-12630; Barnard 1979. J South African Vet Assoc 50: 155-157). Viral titers were determined as TCID50/ml using the Spearman-Kärber method.

Plasmids

All plasmids are described in Table 1. To transiently express genes of interest, pCAGGS plasmids were used. RVFV genome segments were transcribed from minimal T7 promoters on pUC57 plasmids. All plasmids were constructed using standard cloning techniques and gene synthesis (GenScript, New Jersey, USA). Plasmids containing half of the glycoprotein precursor (GPC) gene, either (NSm)Gn or Gc, were segmented at the tyrosine (Y)-675 codon of NSmGnGc (FIG. 8A), without any nucleotide overlap. (Y)-675 is predicted to be the first amino acid of the signal sequence of Gc (Gerrard and Nichol, 2007. Virology 357: 124-133; Suzich et al., 1990. J Virol 64: 1549-1555).

Production of RVFV Replicon Particles

BHK-Rep2 cells were seeded in 6 wells plates and after overnight incubation transfected with a total of 3 µg pCAGGS expression plasmid using JetPEI reagents (Polyplus-transfection SA, Illkirch, France) according the manufacturers' instructions. At 1 day post transfection supernatants were harvested and titrated on BHK cells.

Rescue Experiments

BSR-T7/5 cells were seeded in 6 wells plates (500.000 cells/well) and after overnight incubation, infected for 2 h with a recombinant Fowlpox virus expressing T7 polymerase (FP-T7) (Britton et al., (1996). J Gen Virol 77: 963-967). As an alternative, BSR-T7/5 cells were infected for 2 h with a wildtype Fowlpox virus for rescue of four segmented RVFV. Subsequently, medium was refreshed and cells were transfected with a total of 3 µg pUC57 transcription plasmids per well using JetPEI transfection reagents according to the instructions from the manufacturer. Three to five days post transfection, supernatants were collected and used to infect freshly seeded BSR-T7/5 cells. Viral rescue was visualized using immunofluorescence assays (IFA).

Immunofluorescence

Immunofluorescence assays (IFA) were performed as previously described with some modifications (Oreshkova et al., 2013. PloS one 8(10):e77461). Briefly, infected cell monolayers were fixed with 4% (w/v) paraformaldehyde (15 min) and permeabilized with cold methanol (5 min). Blocking (30 min) and antibody incubations (1 h at 37° C.) were subsequently performed in PBS supplemented with 5% horse serum. To detect Gn expression, monoclonal antibody 4-39-cc was used (Keegan and Collett, 1986. J Virol 58: 263-270) in combination with a Texas Red-conjugated secondary antibody (Abcam, Cambridge, UK). To detect Gc expression, a polyclonal antibody (rabbit) was used (de Boer et al., 2012. J Virol 86: 13642-13652), in combination with an alexa fluor 350-conjugated secondary antibody (Life Technologies, Bleiswijk, The Netherlands). Between antibody incubations cells were washed 3 times with washing buffer (PBS, 0.05% v/v Tween-20). Antibody binding was visualized using an AMG EVOS-FL fluorescence microscope.

Northern Blotting

Northern blotting was performed using the DIG Northern starter kit (Roche, Woerden, The Netherlands) in combination with the Northern-Max-Gly kit (Ambion, Austin, Tex.) as previously described (Kortekaas et al., 2011. J Virol 85: 12622-12630). Primers used for the generation of the RNA probes are listed in Table 2. Viral RNA was isolated using Trizol LS (Sigma-Aldrich, Missouri, United States) in combination with the Direct-zol™ RNA Miniprep kit (Zymo research, California, United States) according the manufactures instructions.

TABLE 1

Plasmids used in this study

| Plasmid | Type | Encodes | UTRs | Product (nt) | Reference |
|---|---|---|---|---|---|
| pCAGGS-M | expression | NSmGnGc | | | [*] |
| pCAGGS-NSmGn | expression | NSmGn | | | this study |
| pCAGGS-Gn | expression | Gn | | | this study |
| pCAGGS-Gc | expression | Gc | | | this study |
| puC57-S | transcription | $N^{(+)}$ + $NSs^{(-)}$ | S-type | 1691 | [*] |
| puC57-S-delNSs | transcription | $N^{(+)}$ | S-type | 922 | this study |
| pUC57-S-eGFP | transcription | $N^{(+)}$ + $eGFP^{(-)}$ | S-type | 1621 | [*] |
| puC57-S-NSmGn | transcription | $N^{(+)}$ + $NSmGn^{(-)}$ | S-type | 2934 | this study |
| pUC57-S-Gc | transcription | $N^{(+)}$ + $Gc^{(-)}$ | S-type | 2484 | this study |
| pUC57-M | transcription | $NSmGnGc^{(+)}$ | M-type | 3885 | [*] |
| pUC57-M-NSmGn | transcription | $NSmGn^{(+)}$ | M-type | 2319 | this study |
| pUC57-M-Gc | transcription | $Gc^{(+)}$ | M-type | 1869 | this study |
| puC57-M-N | transcription | $N^{(+)}$ | M-type | 1032 | this study |
| pUC57-L | transcription | $polymerase^{(+)}$ | L-type | 6404 | [*] |

(NSm)Gn and Gc are segmented at the tyrosine (Y)-675 codon of NSmGnGc
$^{(+)}$genomic sence orientation;
$^{(-)}$anti-genomic sence orientation
All plasmids contain sequences with RVFV strain 35/74 background
(Accesssion numbers: JF784388.1, JF784387.1 and JF784386.1)
[*] Kortekaas et al., 2011. J Virol 85: 12622-12630

Primers used for Northern blot probes

| Primer | Sequence | | Application |
|---|---|---|---|
| JR597 | <u>TAATACGACTCACTATAGGG</u>TCAGTGTTTCCTACTTGAAGGAGGCTT | (SEQ ID NO: 30) | Polymerase forward |
| JR598 | AAGTCCACACAGGCCCCTTACATT | (SEQ ID NO: 31) | Polymerase reverse |
| JR599 | <u>TAATACGACTCACTATAGGG</u>GGTCTGCGAAGTGGGGGTTCAAG | (SEQ ID NO: 32) | Gn forward (1) |
| JR600 | GACAACCAATCCGTGAGGCTCA | (SEQ ID NO: 33) | Gn reverse (1) |
| JR601 | <u>TAATACGACTCACTATAGGG</u>CGGACAACCAATCCGTGAGGCTCAC | (SEQ ID NO: 34) | Gn forward (2) |
| JR602 | CGAAGTGGGGGTTCAAGCACTCAAA | (SEQ ID NO: 35) | Gn reverse (2) |
| JR603 | <u>TAATACGACTCACTATAGGG</u>GTCTCAAGTGAGCTATCGTGCAGGG | (SEQ ID NO: 36) | Gc forward (1) |
| JR604 | ATTGCATACCCTTTGCCTGGGCT | (SEQ ID NO: 37) | Gc reverse (1) |
| JR605 | <u>TAATACGACTCACTATAGGG</u>AGACACGGCTGCTCCCACAAAGTC | (SEQ ID NO: 38) | Gc forward (2) |
| JR606 | CAGTCAGTCAGAAAAGAGGCCCTTAG | (SEQ ID NO: 39) | Gc reverse (2) |
| JR607 | <u>TAATACGACTCACTATAGGG</u>TCAAGCAGTGGACCGCAATGAGATTG | (SEQ ID NO: 40) | N forward |
| JR608 | ATTCACTGCTGCATTCATTGGCTGC | (SEQ ID NO: 41) | N reverse |
| JR609 | <u>TAATACGACTCACTATAGGG</u>ATTCTATCTCAACATCTGGGATTGGAGGA | (SEQ ID NO: 42) | NSs forward |
| JR610 | CACCTCCACCAGCAAAGCCTTTTCA | (SEQ ID NO: 43) | NSs reverse |

<u>_</u>T7 polymerase recognition sequence
(1) Resulting probe recognizes genomic-sense RNA (in wild-type RVFV virus)
(2) Resulting probe recognizes antigenomic-sense RNA (in wild-type RVFV virus)

Animal Experiments

Viral Dissemination RVFV-LMMS$_{NSs}$

Nine-week-old female BALB/cAnCrl mice (Charles River Laboratories) were divided in two groups of 16 mice and one group of 10 mice, kept in type III filter top cages under BSL-3 conditions, and allowed to acclimatize for 6 days. At day 0 the two groups of 16 mice were inoculated via intraperitoneal route (1 ml) with either a low ($10^E3$ TCID$_{50}$) or high ($5.10^E5$ TCID$_{50}$) dose of RVFV-LMMS$_{NSs}$. As a positive control, the group of 10 mice was infected with a low ($10^E3$ TCID$_{50}$) dose of authentic RVFV strain 35/74. Mice were observed daily and at day 1, 4, 8 and 11 post infection 4 mice were euthanized form the groups infected with RVFV-LMMS$_{NSs}$. Viral dissemination in the liver and brain was evaluated by qRT-PCR as described (Kortekaas et al., 2012. Vaccine 30: 3423-3429).

Vaccination-Challenge Experiment

Six-week-old female BALB/cAnCrl mice (Charles River Laboratories) were divided in 4 groups of 10 mice, kept in type III filter top cages under BSL-3 conditions, and allowed to acclimatize for 6 days. At day 0, mice were vaccinated intramuscularly (thigh muscle) with either medium (Mock), NSR-Gn (Oreshkova et al., (2013). PloS one 8(10):e77461), $10^E6$ TCID$_{50}$), RVFV-LMMS$_{eGFP}$ $10^E6$ TCID$_{50}$ or RVFV-LMMS$_{delNSs}$ in 50 μl. Mice were observed daily and three weeks post vaccination mice were challenged intraperitoneally with $10^E3$ TCID$^{50}$ of RVFV strain 35/74 in 1 ml medium. One day prior challenge, RVFV specific neutralization titers in sera were determined as described (Kortekaas et al., 2011. J Virol 85: 12622-12630) using the 4S virus as antigen. Viral dissemination in the liver and brain was evaluated by qRT-PCR as described (Kortekaas et al., 2012. Vaccine 30: 3423-3429).

Results

Splitting of the RVFV GPC Gene does not Abrogate the Functionality of Gn and Gc

Bunyavirus M segments encode GPCs which are proteolytically cleaved into proteins that function in receptor binding and fusion. To evaluate whether proteolytic processing of the RVFV GPC is a prerequisite for the functionality of Gn and Gc, we constructed expression plasmids encoding either (NSm)Gn or Gc and evaluated their ability to facilitate production of RVFV replicon particles (also referred to as non-spreading RVFV (NSR) (Kortekaas et al., 2011. J Virol 85: 12622-12630). The GPC was split at the tyrosine (Y)-675 codon, because this codon is predicted to be the first amino acid of the signal sequence of Gc (Gerrard and Nichol, 2007. Virology 357: 124-133; Suzich et al., 1990. J Virol 64: 1549-1555) (FIG. 8A). BHK cells, stably maintaining replicating L and S$_{eGFP}$ genome segments (BHK-Rep2) cells were co-transfected with pCAGGS-(NSm)Gn and pCAGGS-Gc (FIG. 8B). One day post transfection the level of progeny replicon particles was determined in the supernatant. As a positive control, BHK-Rep2 cells were transfected with pCAGGS-M, which encodes wild-type NSmGnGc (Kortekaas et al., 2011. J Virol 85: 12622-12630). Co-transfection of pCAGGS-Gn and pCAGGS-Gc resulted in average NSR particles of $10^E4$ TCID$_{50}$/ml, whereas co-transfection of pCAGGS-NSmGn and pCAGGS-Gc resulted in average NSR particle production of $10^E6$ TCID$_{50}$/ml, nearly reaching the production level of $10^E7$ TCID$_{50}$/ml, generally obtained after transfection of BHK-Rep2 cells with pCAGGS-M (FIG. 8C). These results show that splitting of the GPC gene does not abrogate Gn and Gc functionality.

Rescue of RVFV with a Segmented GPC Gene

After demonstrating that RVFV L and S genome segments can efficiently be packaged into infectious replicon particles using the NSmGn and Gc expression plasmids, we investigated whether a virus expressing NSmGn and Gc from separate genome segments is viable. Transcription plasmids pUC57-L, pUC57-M-Gc and pUC57-S-NSmGn were used for the rescue of virus with NSmGn expressed form the NSs location of the S-segment and transcription plasmids pUC57-L, pUC57-M-NSmGn and pUC57-S-Gc were used for the rescue of virus with Gc expressed from the NSs location. Virus based on the expression of Gc from the S-segment and NSmGn from the M segment could be rescued, as evidenced by IFA and Northern blot (FIG. 9A-C). The virus, from hereafter referred to as RVFV-LMS-split, was able to grow up to $10^E6$ TCID$_{50}$/ml in BSR cells (FIG. 9D). The successful rescue of the LMS-split virus indicates that Gn and Gc are fully functional when expressed from separate genome segments.

RVFV is Able to Maintain Two S-Type Genome Segments

The finding that Gn and Gc do not require processing as a GPC protein to produce progeny virus provided new opportunities to study the dynamics of RVFV genome packaging. In a first experiment, we investigated whether RVFV is able to package two S-type genome segments in the absence of an M-type genome segment. Rescue experiments were performed with transcription plasmids pUC57-L, pUC57-S-Gc and pUC57-S-NSmGn. In this situation, both NSmGn and Gc will be expressed from the NSs gene location of an S segment. In several attempts, the presence of infectious double S-segment virus, as evidenced by Northern blot and IFA, could be confirmed (FIG. 9A-C). The virus, from hereon referred to as RVFV-LSS, is able to grow up to titers of $10^E5$ TCID$_{50}$/ml in BSR cells (FIG. 9D), which is about 10 times lower than observed with RVFV-LMS-split. The ability to rescue RVFV-LSS indicates that RVFV is able to package more than one S-segment into a single virion.

To further investigate RVFV genome packaging, we evaluated whether viruses could be constructed that comprise four instead of three genome segments (RVFV-4S); one L, one S and two M-type segments. Rescue experiments were performed with transcription plasmids pUC57-L, pUC57-S-eGFP, pUC57-M-NSmGn and pUC57-M-Gc. In this situation, the virus contains an authentic L segment, an S segment that encodes N and eGFP and two M-type segments that encode either NSmGn or Gc. In several attempts, as evidenced by Northern blot and IFA (FIG. 10A-C), the rescue of infectious four-segment RVFV was successful. The RVFV-4S eGFP variant, from hereon referred to as RVFV-LMMS$_{eGFP}$ is able to grow up to $10^E7$ TCID$_{50}$/ml in BSR cells (FIG. 10D).

In addition to RVFV-LMMS$_{eGFP}$, we tried to rescue RVFV-4S viruses with S-segments expressing the N protein and NSs or solely N. Rescue experiments were performed as described for RVFV-LMMS$_{eGFP}$, but instead of pUC57-S-eGFP, pUC57-S(encoding N and NSs) and pUC57-S-delNSs were used. Both viruses, hereon after referred to as RVFV-LMMS$_{NSs}$ and RVFV-LMMS$_{delNSs}$ were viable and able to grow in BSR cells up to $10^E6$ and $10^E7$ TCID$_{50}$/ml, respectively (FIG. 10A-D).

RVFV is Able to Maintain 4 Genome Segments of which 3 are of the M-Type

The results so far strongly suggest that RVFV genome packaging is relatively flexible. To further study this flexibility, we tried to rescue a four segment virus with three instead of two M-type genome segments. In this situation NSmGn, Gc and also N are all encoded by genome segments with M-type UTRs. Rescue experiments were performed with transcription plasmids pUC57-L, pUC57-M-NSmGn, pUC57-M-Gc and pUC57-M-N. In several attempts, successful rescue of RVFV-LMMM could be confirmed by IFA and Northern blot analysis (FIG. 10A-D) and the virus was able to grow up to $10^E6$ TCID$_{50}$/ml in BSR cells. The ability to rescue RVFV-LMMM virus emphasizes that RVFV genome packaging, at least in mammalian cells, is highly flexible.

Evidence for the Packaging of 4 Genome Segments into a Single Virion

To produce progeny virions, RVFV-4S should deliver all 4 genome segments into a single host cell. Theoretically, this can be achieved by infection with a single virion containing all four segments or, alternatively, by co-infection of complementing replicon particles, lacking at least one of the genome segments. To evaluate which of the two mechanisms is used by the RVFV-4S virus, we infected BSR cells with RVFV-LMMS$_{eGFP}$ and evaluated GFP, Gn and Gc expression 16 h post infection using IFA. RVFV$_{eGFP}$ was used as a reference. As expected, the fast majority (>99%) of RVFV$_{eGFP}$ virions contain at least one L, one M and one S segment as evidenced by the high percentage of infected cells that expressed eGFP, Gn and Gc (FIG. 11). Infrequently, cells were observed that expressed eGFP in the absence of Gn and Gc. Most likely these cells were infected by two segmented replicons lacking the M-segment.

Comparable to RVFV$_{eGFP}$, almost all (>99%) eGFP-expressing cells showed expression of both Gn and Gc after infection with RVFV-LMMS$_{eGFP}$. Once again, only a limited number of eGFP positive cells were observed that did not express Gn and Gc (FIG. 10). As expected, there were also some eGFP-positive cells that expressed Gn in the absence of Gc, or Gc in the absence of Gn, indicative for the presence of replicon particles lacking at least one of the four genome segments. These results, together with the observation that RVFV-4S is able to spread at low MOI (data not shown), indicate that RVFV-4S primarily produces progeny by infection with 4 segment virions rather than by infection with complementing replicon particles.

Growth of RVFV with Segmented Glycoprotein Precursor Genes in Insect Cell Culture In the experiments described thus far, viruses with segmented glycoprotein precursor genes were grown in mammalian cells. Since RVFV is a mosquito-borne pathogen and able to grow efficiently in insect cells, we compared the growth of wildtype and mutant viruses in Aedes albopictus C6/36 insect cell culture. As a positive control, viruses were grown in BSR cells. As expected, authentic RVFV and RVFV$_{eGFP}$ were able to grow efficiently in the C6/36 cells. In sharp contrast, none of the viruses with a segmented glycoprotein precursor gene were able to spread efficiently in C6/36 cell culture (FIG. 12). This result suggests that RVFV GPC processing and/or genome packaging is less flexible in mosquito cells.

RVFV-4S Comprising all RVFV Genes is Innocuous in Mice

Figures 13A, 13B, 13C:
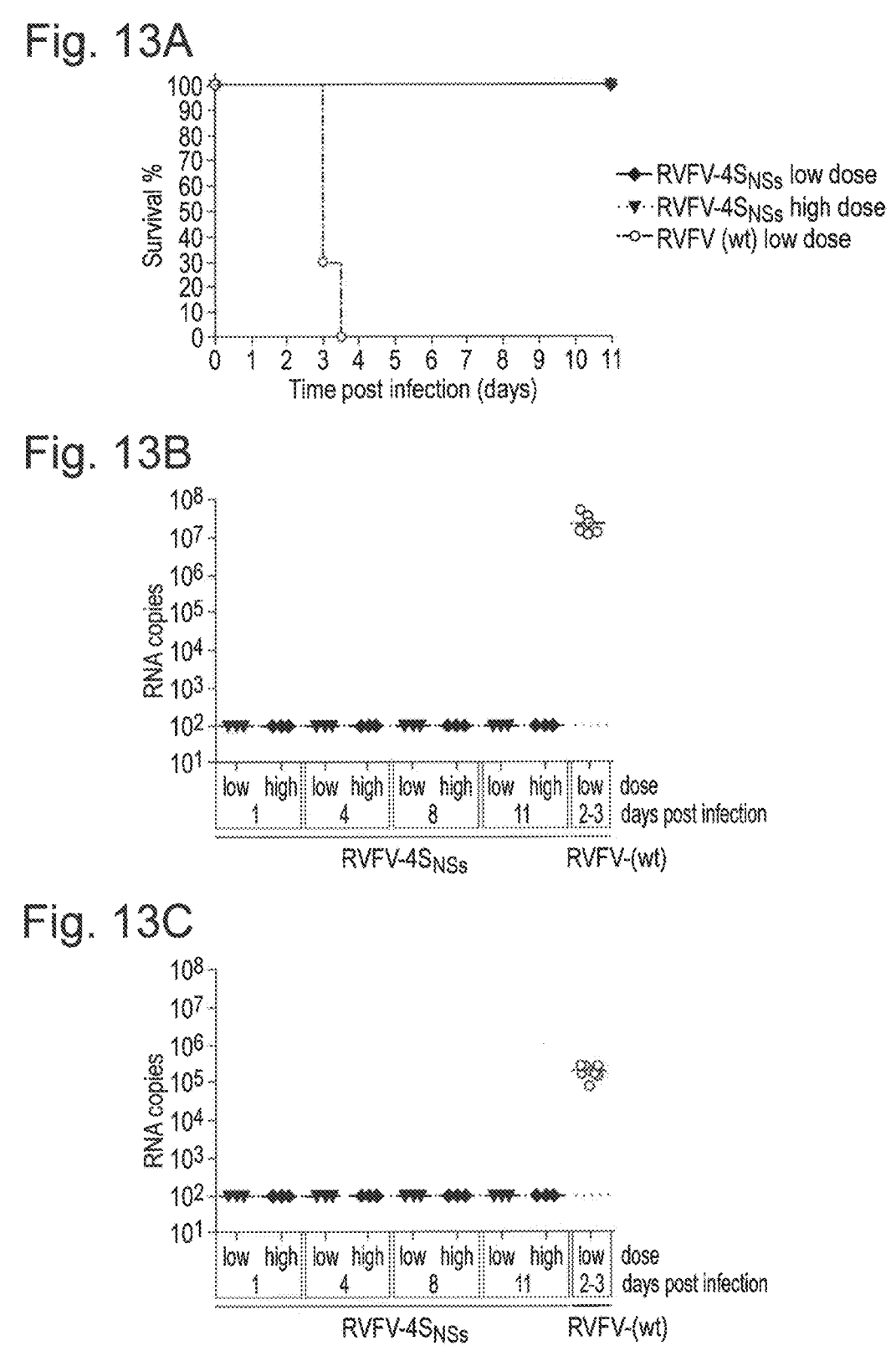

Since the growth of viruses with segmented glycoprotein precursor genes is somewhat impaired in mammalian cells and strongly impaired in insect cells, we hypothesized that these viruses might have reduced virulence. To study the effect of GPC gene segmentation on virulence we evaluated whether a four-segmented containing all RVFV genes, including the major virulence factor NSs (RVFV-LMMS$_{NSs}$), is able to cause disease in a mouse model. Mice were infected with either a low ($10^E3$ TCID$_{50}$) or a high ($5.10^E5$ TCID$_{50}$) dose of RVFV-LMMS$_{NSs}$ and, after different time points, mice were sacrificed for the evaluation of virus dissemination to the organs. As a positive control, one group of mice was infected with a low dose of authentic RVFV. All mice infected with authentic RVFV died within four days post infection, whereas none of the mice infected with RVFV-LMMS$_{NSs}$ died or showed clinical symptoms, not even when inoculated with the 500-fold higher dose (FIG. 13A). Evaluation of virus dissemination to the livers and brains confirmed that RVFV-LMMS$_{NSs}$ was unable to spread systemically (FIG. 13B-C). Altogether, these results indicate that RVFV-4S is innocuous in mice.

RVFV-4S Induces a Protective Immune Response in Mice

Figures 14A, 14B, 14C, 14D:
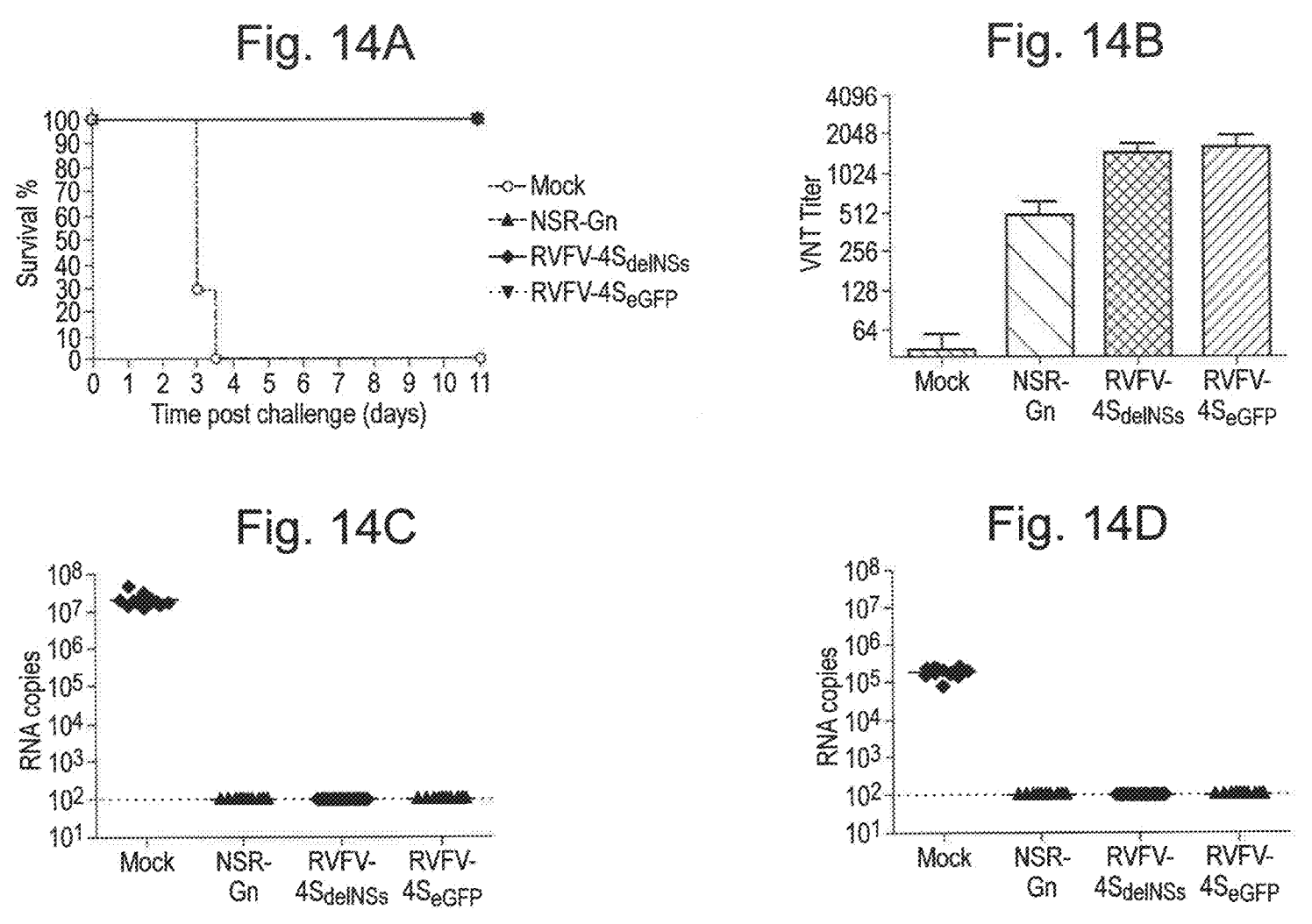

Since RVFV-4S grows well in cell culture and is innocuous in mice, we considered this virus to be a highly promising vaccine candidate. To investigate whether RVFV-4S is able to induce a protective immune response in mice, we performed a vaccination-challenge experiment. Mice were intramuscularly vaccinated with $10^E6$ TCID$_{50}$ of RVFV-LMMS$_{eGFP}$ or RVFV-LMMS$_{delNSs}$. As a positive control mice were vaccinated with $10^E6$ TCID50 NSR-Gn (Oreshkova et al., (2013) PloS one 8(10):e77461). At three weeks post vaccination mice were challenged with a lethal dose of authentic RVFV. Within 4 days post challenge all mock-vaccinated control mice succumbed to the infection (FIG. 14A). In contrast, mice vaccinated with RVFV-LMMS$_{eGFP}$ or RVFV-LMMS$_{delNSs}$ remained healthy during the entire experiment. Analysis of sera and organs of vaccinated animals demonstrated the presence of a neutralizing antibody response (FIG. 14B) and the absence of systemic spread of challenge virus (FIG. 14C-D). Collectively, these results demonstrate that RVFV-4S can be used as a vaccine that optimally combines the safety of an inactivated vaccine with the efficacy of a live vaccine.

Example 3

Materials and Methods
Preparation Vaccine and Challenge Virus

RVFV-LMMS$_{delNSs}$ was used as vaccine virus and was rescued and produced on BSR cells as described in Example 2. The virus was diluted in BSR growth medium consisting of CO2 independent medium (CIM, Invitrogen) supplemented with 5% fetal bovine serum and 1% penicillin-streptomycin, hereafter referred to as complete CIM medium. The recombinant RVFV strain 35/74 (RVFV rec35/74) was used as challenge virus (Kortekaas et al., 2011. J Virol 85: 12622-12630). Titers were determined as 50% tissue culture infective dose (TCID$_{50}$) using the Spearman-Kärber algorithm Vaccination and Challenge of Lambs Conventional 9-11 week-old lambs were divided into five groups of seven animals. After one week of acclimatization, lambs of groups 1-4 were vaccinated via either the subcutaneous or intramuscular (right thigh) route with a medium dose (MD, $10^{5.1}$ TCID$_{50}$) or high-dose (HD, $10^{6.1}$ TCID$_{50}$) of RVFV-LMMS$_{delNSs}$. Lambs of group 5 were mock-vaccinated. Three weeks post vaccination, all lambs were challenged via the intravenous route (jugular vein) with $10^5$ TCID$_{50}$ of RVFV rec35/74. Vaccine and challenge viruses were administered in 1 ml complete CIM medium. Prior to challenge, animals were sedated by intramuscular administration of medetomidine (40 µg/kg medetomidine hydrochloride, Sedator®, Eurovet, The Netherlands). Rectal temperatures were determined daily and serum blood samples were obtained weekly. EDTA blood samples were also obtained weekly. During the first 6 and 11 days post vaccination and challenge, respectively, additional EDTA blood samples were taken daily. At the end of the experiment (three weeks post challenge), or when humane endpoints were reached, animals were euthanized by exsanguination, after being anesthetized with 50 mg/kg sodium pentobarbital (Euthasol®, ASTfarma BV, The Netherlands) applied via the intravenous route. Plasma samples were analyzed for the presence of RVFV RNA with quantitative real-time PCR (qRT-PCR) as described previously (Kortekaas et al., 2012. Vaccine 30: 3423-3429). Virus neutralization titers were determined using a RVFV-LMMSeGFP-based virus neutralization test (VNT) as described in Example 1.

Results

Vaccination with RVFV-4S Protects Lambs from Viremia, Fever and Mortality

Figure 15A:
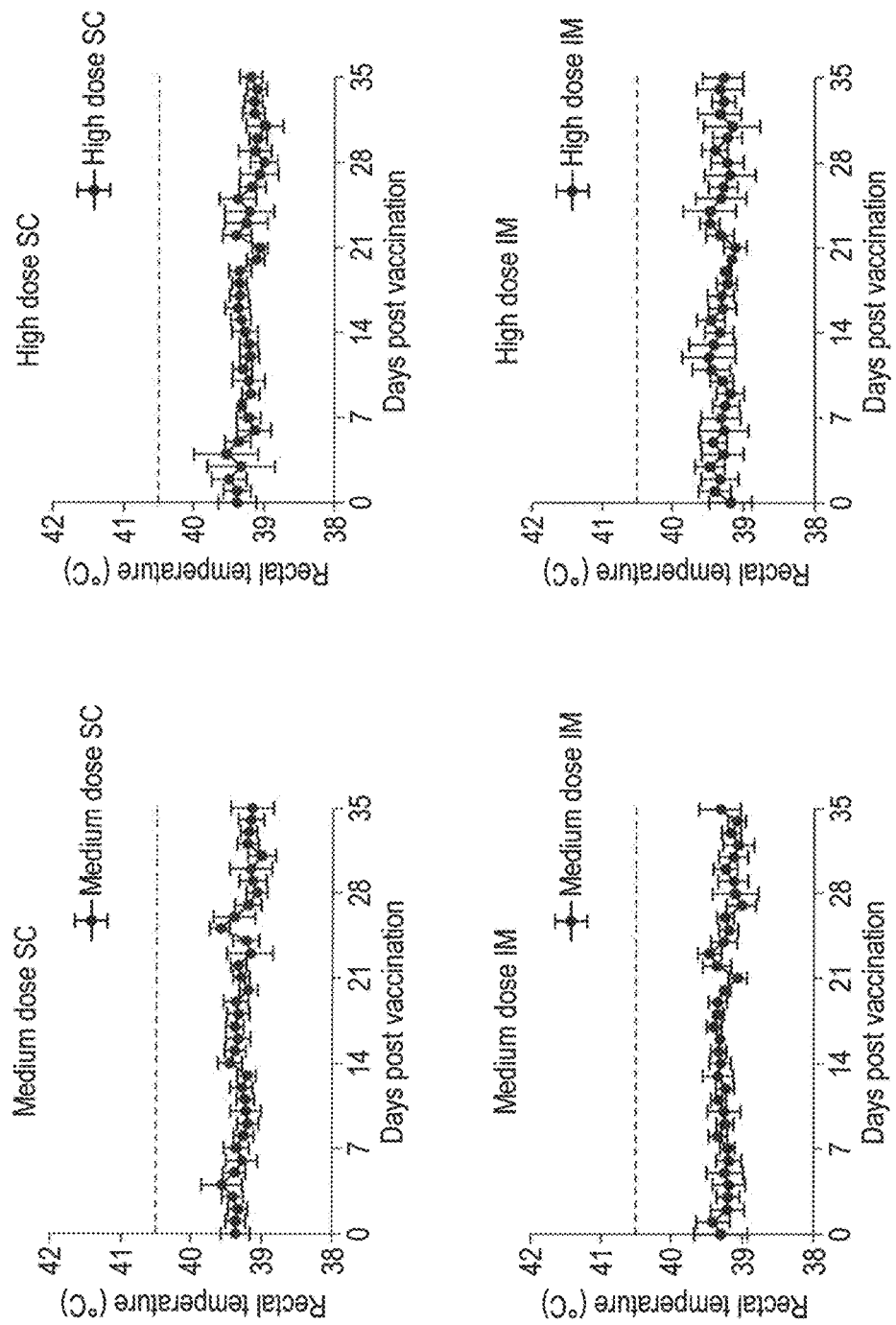
Figure 15B:
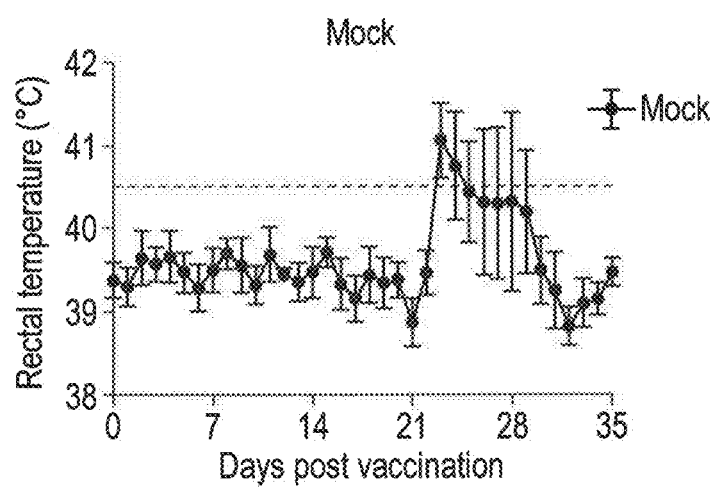
Figure 16A:
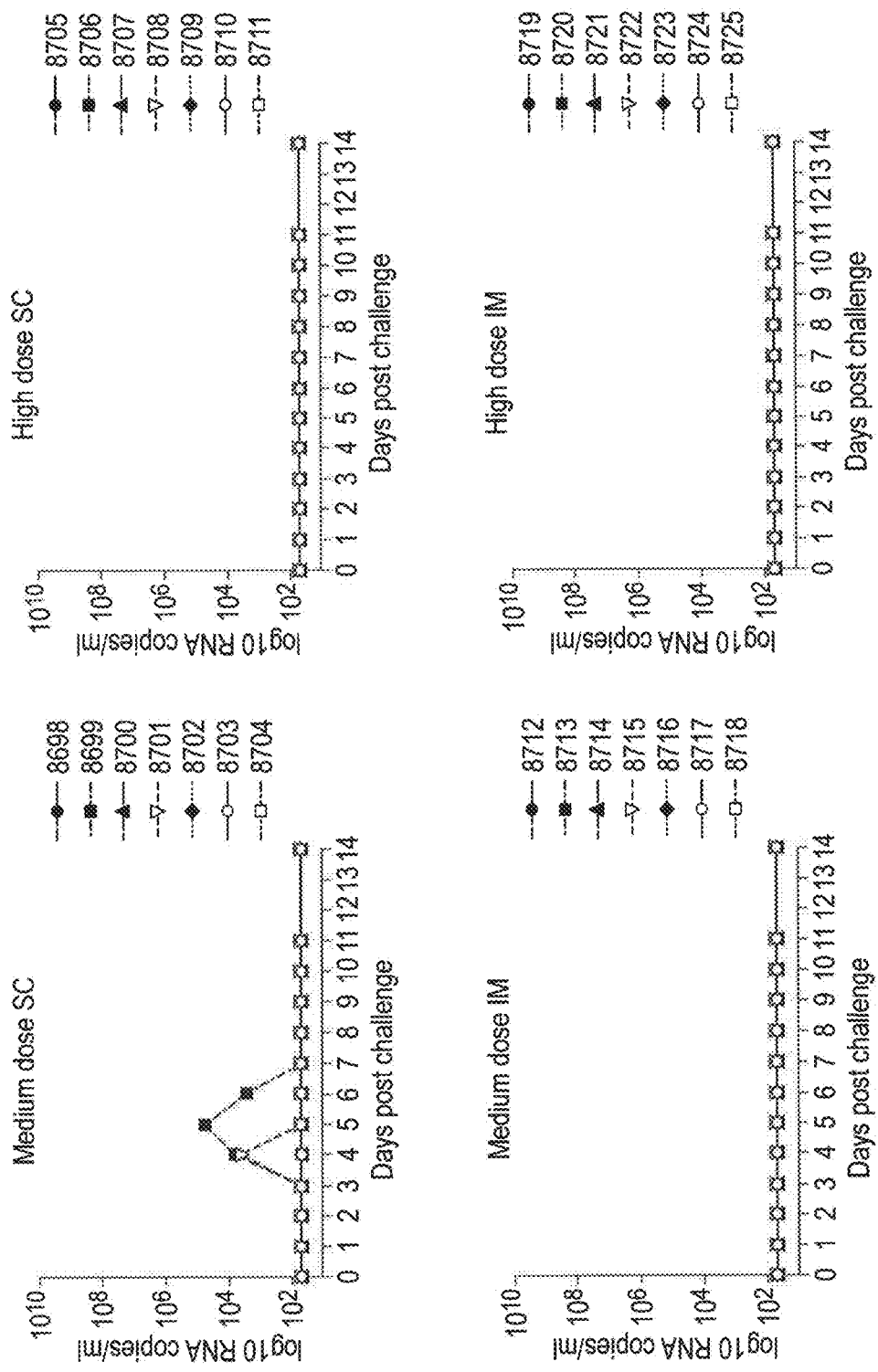

To evaluate the potential of RVFV-4S as a vaccine for sheep, we performed a vaccination-challenge experiment with lambs. These lambs were offspring from Texel-Swifter ewes and a Suffolk ram. Thirty-five lambs were divided into five groups of seven animals at day-7. At day 0, lambs of groups 1 and 2 were vaccinated subcutaneously with $10^{5.1}$ TCID$_{50}$ or $10^{6.1}$ TCID$_{50}$ RVFV-LMMS$_{delNSs}$. Lambs of group 3 and 4 were vaccinated intramuscularly with $10^{5.1}$ TCID50 or $10^{6.1}$ TCID50 RVFV-LMMS$_{delNSs}$. Lambs of group 5 were mock vaccinated and served as a challenge control group. No vaccine virus was detected in plasma samples by qRT-PCR before challenge, indicating that RVFV-LMMS$_{delNSs}$ is unable to induce viremia and strongly suggesting RVFV-LMMS$_{delNSs}$ is unable to spread efficiently in vivo. After challenge, mock-vaccinated lambs developed fever (>40.5° C.), starting within 2 days post challenge and lasting on average for four days (FIG. 15B). In the first week post challenge these animals also displayed a high viremia, as evidenced by qRT-PCR (up to ≈$10^{10}$ RNA copies/ml plasma) (FIG. 16B). Two lambs in this control group succumbed to the RVFV infection 3 days after challenge infection and one lamb died 7 days after challenge infection. No fever was observed in any of the vaccinated lambs and no viral RNA or infectious virus could be detected in the plasma samples of the HD and MD intramuscularly and the HD subcutaneously vaccinated lambs (FIGS. 15A and 16A). Only two sheep vaccinated with the medium-dose and via the subcutaneous route displayed very low levels of systemic viral RNA at 4-7 days post challenge. Altogether these results indicate that sterile protection against RVFV challenge in sheep can be achieved by a single (preferably intramuscular) administration of $10^5$ TCID$_{50}$ RVFV-4S particles.

Intramuscularly Vaccinated Lambs Display Higher Neutralizing Antibody Responses Compared to Subcutaneously Vaccines Lambs Using a previously developed highly sensitive VNT test (Example 1) sera were evaluated for the presence of RVFV-specific neutralizing antibodies. As expected, neutralizing antibodies were not detected in any of the sera collected on the day of vaccination or in sera of mock-vaccinated animals collected before challenge (FIG. 17). In contrast, high levels of neutralizing antibodies were detected in sera obtained one, two and three weeks post RVFV-4S vaccination (FIG. 17A). Remarkably, average titers of MD subcutaneously vaccinated animals were significantly lower at one and two weeks post vaccination compared to the MD intramuscular vaccinated group. In addition, only the MD subcutaneously vaccinated animals displayed a significant increase in VNT titer after challenge. Collectively, these results demonstrate that RVFV-4S is able to induce a substantial and effective systemic neutralizing immune response in sheep, especially when applied via the intramuscular route.

The invention claimed is:

1. A bunyavirus of the genus *Phlebovirus*, in which separated Gn and Gc coding regions, or separated NSmGn and Gc coding regions, are functionally present on two separate genome segments.

2. The bunyavirus of claim 1, comprising a total of 4 genome segments.

3. The bunyavirus according to claim 1, comprising
a bunyavirus L genome segment;
a bunyavirus S genome segment or part of a S genome segment comprising at least the N gene and the 3' and 5' UTRs; and
a bunyavirus M genome segment from which the Gn or Gc coding region, or the NSmGn or Gc coding region, has been functionally inactivated,
whereby the Gn or Gc coding region, or the NSmGn or Gc coding region, that is functionally inactivated on the M genome segment is functionally present on a second M genome segment.

4. The bunyavirus according to claim 1, wherein a bunyavirus L genome segment and/or a S genome segment comprises a foreign gene.

5. A bunyavirus according to claim 1, wherein the Gn and/or the Gc coding region, or the NSmGn and/or Gc coding region, is from a bunyavirus that differs from the bunyavirus from which the L and S genome segments were obtained.

6. A bunyavirus according to claim 1, further comprising a nucleocapsid (N) coding region from a bunyavirus that differs from the bunyavirus from which the genome segments and Gn and/or Gc coding region, or the NSmGn and/or Gc coding region, were obtained.

7. A bunyavirus according to claim 1, wherein an NSs coding region on a S genome segment is functionally inactivated.

8. A method for producing a bunyavirus, the method comprising

A) providing a eukaryotic cell with growth medium; and
B) infecting the eukaryotic cell with the bunyavirus according to claim 1.

9. A composition comprising a bunyavirus according to claim 1, and a suitable excipient.

10. The composition according to claim 9, which is an immunogenic composition.

11. The bunyavirus according to claim 1, for use as a medicament.

12. A vaccine comprising the bunyavirus according to claim 1.

13. A method for generating a bunyavirus of the genus *Phlebovirus*, the method comprising:
A) providing a cell with a bunyavirus of the genus *Phlebovirus* comprising at least one genome segment functionally encoding a RdRp gene and an N gene, and
B) providing the cell with at least two genome segments selected from L, M, and S genome segments in which separated Gn and Gc coding regions, or separated NSmGn and Gc coding regions, are functionally present on two separate genome segments.

14. The method according to claim 13, whereby the cell is provided with a genomic segment by providing the cell with a vector that comprises cDNA of said genomic segment which is flanked by a T7 promoter and cDNA of a ribozyme, further comprising providing the cell with a T7 polymerase.

15. The bunyavirus of claim 1, comprising a total of 3 genome segments.

16. The method according to claim 13, wherein the separated Gn and Gc coding regions are present on two separate minigenome segments, or on a genome segment and a minigenome segment.

17. The composition according to claim 9, for use as a medicament.

18. A vaccine comprising the composition according to claim 9.

* * * * *